United States Patent
Yin et al.

(10) Patent No.: US 10,941,395 B2
(45) Date of Patent: Mar. 9, 2021

(54) METHOD FOR GENE EDITING

(71) Applicant: MASSACHUSETTS INSTITUTE OF TECHNOLOGY, Cambridge, MA (US)

(72) Inventors: Hao Yin, Cambridge, MA (US); Wen Xue, Cambridge, MA (US); Daniel G. Anderson, Framingham, MA (US); Joseph R. Dorkin, Somerville, MA (US); Tyler E. Jacks, Newton, MA (US)

(73) Assignee: MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 0 days.

(21) Appl. No.: 16/029,273

(22) Filed: Jul. 6, 2018

(65) Prior Publication Data

US 2019/0002869 A1   Jan. 3, 2019
US 2019/0144845 A9   May 16, 2019

Related U.S. Application Data

(63) Continuation of application No. 15/374,227, filed on Dec. 9, 2016, now Pat. No. 10,047,355, which is a continuation of application No. PCT/US2015/035077, filed on Jun. 10, 2015.

(60) Provisional application No. 62/010,306, filed on Jun. 10, 2014, provisional application No. 62/113,887, filed on Feb. 9, 2015, provisional application No. 62/156,562, filed on May 4, 2015.

(51) Int. Cl.

| | | |
|---|---|---|
| *C12N 15/88* | (2006.01) | |
| *C12N 15/10* | (2006.01) | |
| *C12N 15/11* | (2006.01) | |
| *A61K 48/00* | (2006.01) | |
| *C12N 7/00* | (2006.01) | |
| *C12N 15/85* | (2006.01) | |
| *C12N 15/86* | (2006.01) | |

(52) U.S. Cl.
CPC .......... *C12N 15/102* (2013.01); *A61K 48/005* (2013.01); *C12N 7/00* (2013.01); *C12N 15/111* (2013.01); *C12N 15/85* (2013.01); *C12N 15/86* (2013.01); *C12N 15/88* (2013.01); *C12N 2310/20* (2017.05); *C12N 2750/14143* (2013.01)

(58) Field of Classification Search
CPC ................................................. C12N 15/102
See application file for complete search history.

(56) References Cited

U.S. PATENT DOCUMENTS

| | | |
|---|---|---|
| 5,543,158 A | 8/1996 | Gref et al. |
| 6,007,845 A | 12/1999 | Domb et al. |
| 6,254,890 B1 | 7/2001 | Hirosue et al. |
| 6,998,115 B2 | 2/2006 | Langer et al. |
| 7,427,394 B2 | 9/2008 | Anderson et al. |
| 7,727,969 B2 | 6/2010 | Farokhzad et al. |
| 8,071,082 B2 | 12/2011 | Zugates et al. |
| 8,105,652 B2 | 1/2012 | Wood et al. |
| 8,193,334 B2 | 6/2012 | Radovic-Moreno et al. |
| 8,323,698 B2 | 12/2012 | Gu et al. |
| 8,450,298 B2 | 5/2013 | Mahon et al. |
| 8,697,359 B1 | 4/2014 | Zhang |
| 10,047,355 B2 | 8/2018 | Yin et al. |
| 2008/0268063 A1 | 10/2008 | Jon et al. |
| 2009/0298710 A1 | 12/2009 | Farokhzad et al. |
| 2010/0303723 A1 | 12/2010 | Farokhzad et al. |
| 2011/0009641 A1 | 1/2011 | Anderson et al. |
| 2011/0027172 A1 | 2/2011 | Wang et al. |
| 2011/0065807 A1 | 3/2011 | Radovic-Moreno et al. |
| 2012/0156135 A1 | 6/2012 | Farokhzad et al. |
| 2012/0251560 A1 | 10/2012 | Dahlman et al. |
| 2013/0017223 A1 | 1/2013 | Hope et al. |
| 2013/0158021 A1 | 6/2013 | Dong et al. |
| 2013/0259924 A1 | 10/2013 | Bancel et al. |
| 2014/0017212 A1 | 1/2014 | Rebar |
| 2014/0068797 A1 | 3/2014 | Doudna et al. |
| 2014/0093575 A1 | 4/2014 | Hammond et al. |
| 2014/0315985 A1* | 10/2014 | May .................. C12Q 1/68 514/44 R |
| 2015/0031132 A1 | 1/2015 | Church et al. |

FOREIGN PATENT DOCUMENTS

| | | |
|---|---|---|
| WO | 2013090861 A1 | 6/2013 |
| WO | 2014065596 A1 | 5/2014 |
| WO | 2015089427 A1 | 6/2015 |
| WO | 2015191693 A2 | 12/2015 |

OTHER PUBLICATIONS

Yin et al. (Nature Biotechnology. Mar. 2016; 14(1): 328-333) (Year: 2016).*
Chen, D. et al., "Rapid Discovery of Potent siRNA-Containing Lipid Nanoparticles Enabled by Controlled Microfluidic Formulation," J. Am. Chem. Soc., vol. 134, pp. 6948-6951 (2012).
Cong, L. et al., "Multiplex Genome Engineering Using CRISPR/Cas Systems," Science, vol. 339, pp. 819-823 (2013).
Corey, D. R., "Chemical modification: the key to clinical application of RNA interference?" The Journal of Clinical Investigation, vol. 117, No. 12, pp. 3615-3622 (2007).
Dong, Y. et al., "Lipopeptide nanoparticles for potent and selective siRNA delivery in rodents and nonhuman primates," Proceedings of the National Academy of Sciences, vol. 111, No. 11, Mar. 18, 2014, pp. 3955-3960.

(Continued)

*Primary Examiner* — Scott Long
(74) *Attorney, Agent, or Firm* — Hamilton, Brook, Smith & Reynolds, P.C.

(57) ABSTRACT

The present disclosure relates to compositions and methods for modifying a gene sequence, and for systems for delivering such compositions. For example, the disclosure relates to modifying a gene sequence using a CRISPR-Cas9 or other nucleic acid editing system, and methods and delivery systems for achieving such gene modification, such as viral or non-viral delivery systems.

28 Claims, 37 Drawing Sheets

Specification includes a Sequence Listing.

(56) References Cited

OTHER PUBLICATIONS

Doudna, J. A. et al., "The new frontier of genome engineering with CRISPR-Cas9," Science, vol. 346, Issue 6213 (2014); http://science.sciencemag.org, 11 pages.
Eltoukhy, A. A., et al., "Nucleic acid-mediated intracellular protein delivery by lipid-like nanoparticles," Biomaterials, vol. 35, No. 24, May 13, 2014, pp. 6454-6491.
Gao et al. (PNAS. Sep. 3, 2002; 99(18):11854-11859). (Year: 2002).
Gao, Y, et al., Self-Processsing of Ribozyme-Flanked RNAs Into Guide RNAs In Vitro and In Vivo for CRISPR-Mediated Genome Editing, Journal of Integrative Plant Biology, Apr. 2014; vol. 54, No. 4; pp. 343-349; abstract, p. 343, col. 2, second paragraph, p. 344, col. 2, third paragraph, figure 3.
Gilbert, L. A. et al., "CRISPR-Mediated Modular RNA-Guided Regulation of Transcription in Eukaryotes," Cell, vol. 154, pp. 442-451 (2013).
Gratz, S. J. et al., "Genome Engineering of *Drosophila* with the CRISPR RNA-Guided Cas9 Nuclease," Genetics, vol. 194, Aug. 2013, pp. 1029-1035.
Hao, Y. et al., "Delivery technologies for genome editing," Nature Reviews, Drug Discovery, vol. 16, No. 6, Mar. 24, 2017, pp. 387-399.
Hao, Y. et al., "Genome editing with Cas9 in adult mice corrects a disease mutation and phenotype," Nature Biotechnology, vol. 32, No. 6, Mar. 30, 2014, pp. 551-553.
Hao, Y. et al., "Therapeutic genome editing by combined viral and non-viral delivery of CRISPR system components in vivo," Nature Biotechnology, vol. 34, No. 3, Feb. 1, 2016, pp. 328-333.
Kanasty, R. et al., "Delivery materials for siRNA therapeutics," Nature Materials, vol. 12, pp. 967-977 (2013).
Kormann, M. S. D. et al., "Expression of therapeutic proteins after delivery of chemically modified mRNA in mice," Nature Biotechnology, vol. 29, No. 2, pp. 154-157 (2011).
Love, K. T. et al., "Lipid-like materials for low-dose, in vivo gene silencing," PNAS, vol. 107, No. 5, pp. 1864-1869 (2010).
Mali, P. et al., "Cas9 as a versatile tool for engineering biology," Nature Methods, vol. 10, No. 10, pp. 957-963 (2013).
Mali, P. et al., "RNA-Guided Human Genome Engineering via Cas9," Science, vol. 339, pp. 823-826 (2013).
Paul, DS, et al., Functional Interpretation of Non-Coding Sequence Variation; Concepts and Challenges, Bioessays, Feb. 2014; vol. 36, No. 2; pp. 191-199, DOI:10.1002/bles.201300126. Epub Dec. 2013 5.36: 191-199; abstract, p. 197, first column, first paragraph.
Pyzocha, N. K. et al., "RNA-Guided Genome Editing of Mammalian Cells," Methods Mol. Biol., vol. 1114, pp. 269-277 (2014).
Ramakrishna, S. et al., "Gene disruption by cell-penetrating peptide-mediated delivery of Cas9 protein land guide RNA," Genome Research, vol. 24, No. 6, Apr. 2, 2014, pp. 1020-1027.
Ran, A. F. et al., "Genome engineering using the CRISPR-Cas9 system," Nature Protocols, vol. 8, No. 11, No. 1, 2013, pp. 2281-2308.
Sander, J. D. et al., "CRISPR-Cas systems for editing, regulating and targeting genomes," Nature Biotechnology, vol. 32, No. 4, pp. 347-355 (2014).
Shen, B. et al., "Efficient genome modification by CRISPR-Cas9 nickase with minimal off-target effects," Nature Methods, vol. 11, No. 4, pp. 399-402 (2014).
Xue, W. et al., "Response and resistance to NF-.kappa.b inhibitors in mouse models of lung adenocarcinoma," Cancer Discov., vol. 1, pp. 236-247 (2011).
Yin, H. et al., "Genome editing with Cas9 in adult mice corrects a disease mutation and phenotype," Nature Biotechnology, vol. 32, No. 6, pp. 551-553 (2014).
Zhang, F., et al., CRISPR/Cas9 for Genome Editing: Progress, Implications and Challenges; Human Molecular Genetics, 2014; vol. 23, Review Issue No. 1, Advance Access published on Mar. 20, 2014; DOI:10.1093/hmg/ddu125; p. R43, col. 1, paragraph 2.
Extended European Search Report dated Nov. 27, 2017 from European Application No. EP 15 805 852.9, 9 pages.
International Preliminary Report on Patentability dated Dec. 22, 2016 for PCT/US2015/035077 filed Jun. 10, 2015, Applicant: Massachusetts Institute of Technology.
International Search Report and Written Opinion dated Dec. 4, 2015 for PCT/US15/35077 filed Jun. 10, 2015, Applicant: Massachusetts Institute of Technology.
Yin et al., "Therapeutic genome editing by combined viral and non-viral delivery of CRISPR system components in vivo," Nature Biotech. 34(3): 328-33 (2016).

* cited by examiner

Figures 2A and 2B
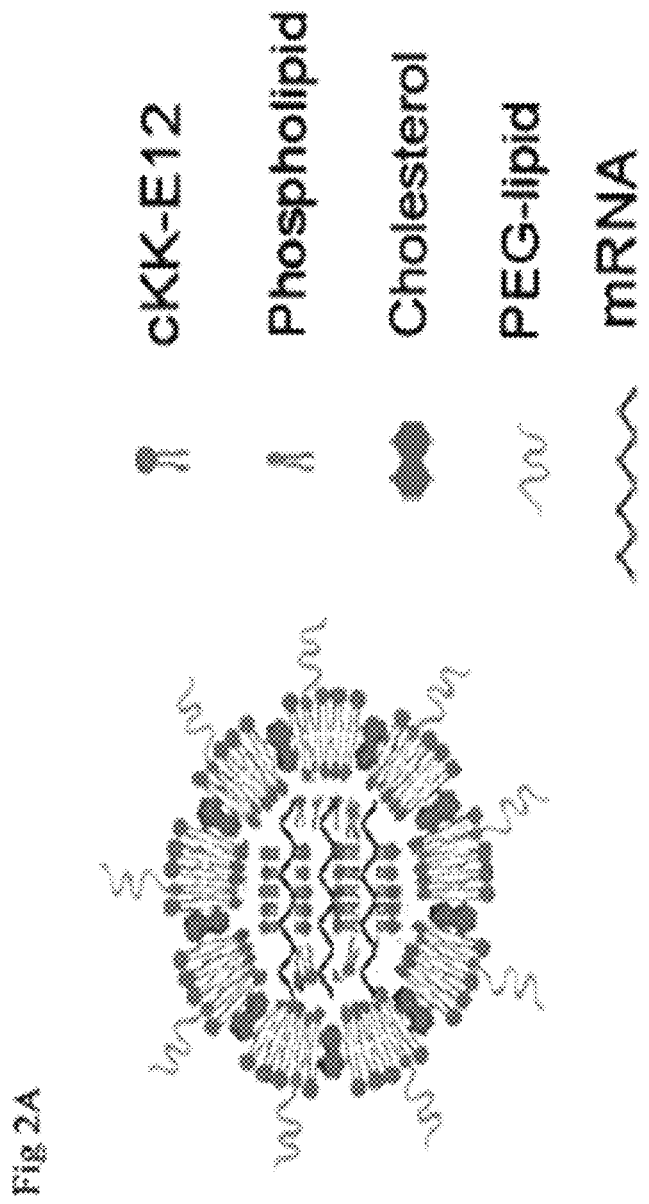
Fig 2A
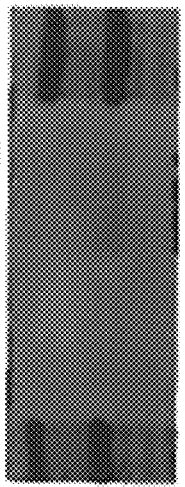
Fig 2B

Figures 3A and 3B
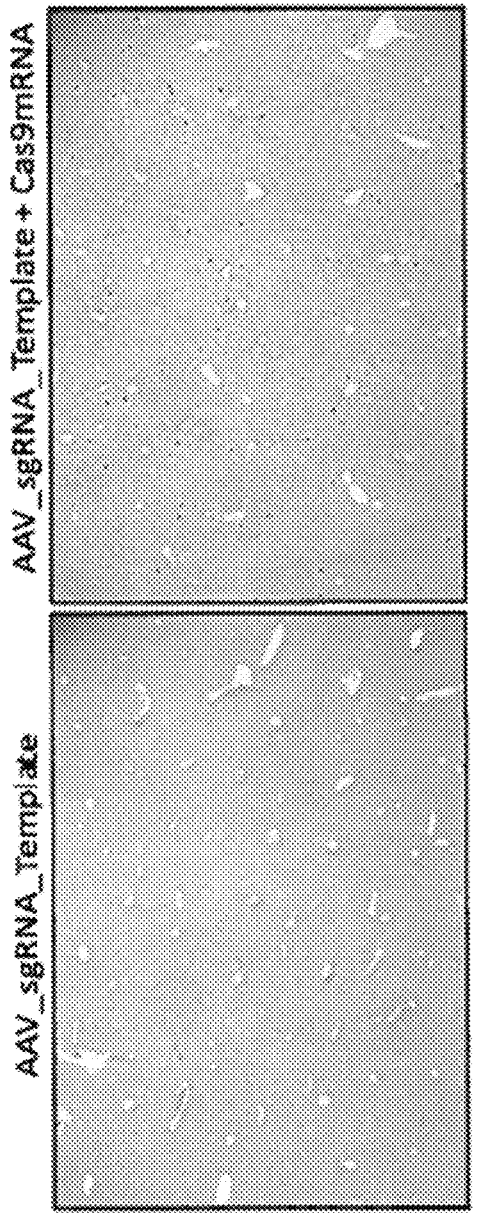
Fig. 3A
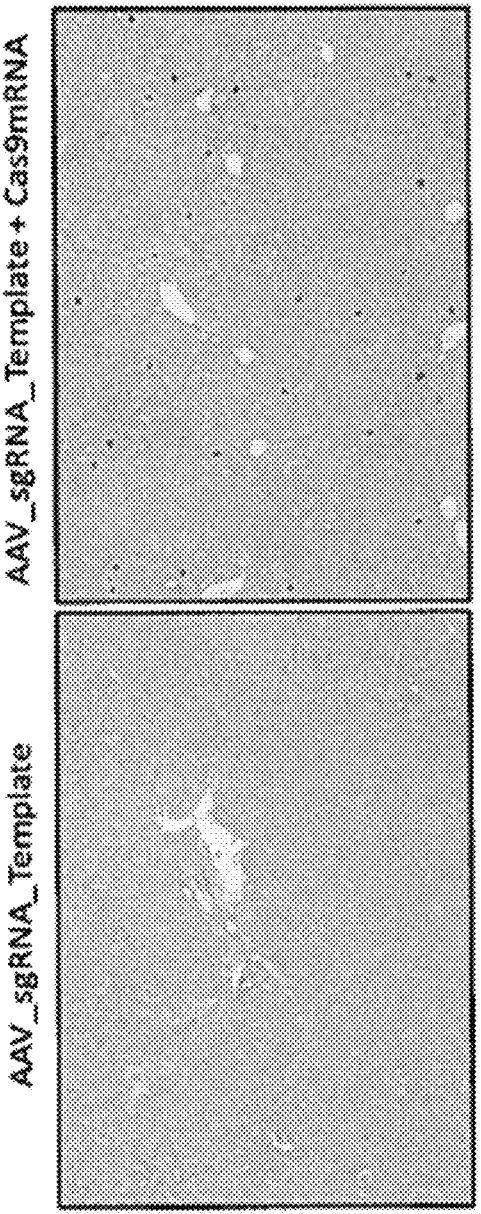
Fig. 3B

```
                    ▼ PAM
GGGCGAGGAGCTGTTCACCGGGG  wt

GGGCGAGGAGCTGTTCA----GG  indels
GGGCGAGGAGCTGTTCA--GGGG
GGGCGAGGAGCTGTTCA-CGGGG
GGGCGAGGAGCTGTTCACCGGGG
                 ↑
                 A
```

Figure 8c

SEQUENCE LISTING

<160> NUMBER OF SEQ ID NOS: 7

<210> SEQ ID NO 1
<211> LENGTH: 23
<212> TYPE: DNA
<213> ORGANISM: Artificial Sequence
<220> FEATURE:
<223> OTHER INFORMATION: GFP locus

<400> SEQUENCE: 1
gggcgaggag ctgttcaccg ggg                                           23

<210> SEQ ID NO 2
<211> LENGTH: 19
<212> TYPE: DNA
<213> ORGANISM: Artificial Sequence
<220> FEATURE:
<223> OTHER INFORMATION: GFP locus indel

<400> SEQUENCE: 2
gggcgaggag ctgttcagg                                                19

<210> SEQ ID NO 3
<211> LENGTH: 21
<212> TYPE: DNA
<213> ORGANISM: Artificial Sequence
<220> FEATURE:
<223> OTHER INFORMATION: GFP locus indel

```
<400> SEQUENCE: 3
gggcgaggag ctgttcaggg g                                              21

<210> SEQ ID NO 4
<211> LENGTH: 22
<212> TYPE: DNA
<213> ORGANISM: Artificial Sequence
<220> FEATURE:
<223> OTHER INFORMATION: GFP locus indel

<400> SEQUENCE: 4
gggcgaggag ctgttcacgg gg                                             22

<210> SEQ ID NO 5
<211> LENGTH: 23
<212> TYPE: DNA
<213> ORGANISM: Artificial Sequence
<220> FEATURE:
<223> OTHER INFORMATION: GFP locus indel

<400> SEQUENCE: 5
gggcgaggag ctgttcaccg ggg                                            23

<210> SEQ ID NO 6
<211> LENGTH: 24
<212> TYPE: DNA
<213> ORGANISM: Artificial Sequence
<220> FEATURE:
<223> OTHER INFORMATION: GFP locus indel

<400> SEQUENCE: 6
gggcgaggag ctgttcaacc gggg                                           24

<210> SEQ ID NO 7
<211> LENGTH: 30
<212> TYPE: DNA
<213> ORGANISM: Artificial Sequence
<220> FEATURE:
<223> OTHER INFORMATION: repaired fah mRNA

<400> SEQUENCE: 7
aacgactgga gcgcacgaga catccagcaa                                     30
```

METHOD FOR GENE EDITING

CROSS-REFERENCE TO RELATED APPLICATIONS

This application is a continuation of U.S. patent application Ser. No. 15/374,227, filed Dec. 9, 2016, now U.S. Pat. No. 10,047,355, which is a continuation of PCT Application No. PCT/US2015/035077, filed Jun. 10, 2015, entitled "METHOD FOR GENE EDITING," which is hereby incorporated by reference in its entirety including drawings.

STATEMENT OF GOVERNMENT SUPPORT

This invention was made with Government support under Grant Nos. P01 CA042063, P30 CA014051, and U54 CA151884 awarded by the National Institutes of Health. The Government has certain rights in the invention.

STATEMENT REGARDING SEQUENCE LISTING

The contents of the text file submitted electronically herewith are incorporated herein by reference in their entirety: A computer readable format copy of the Sequence Listing (filename: MITX_7117_03US_ST25.txt, date recorded: Dec. 9, 2016, file size: 1.75 kb)

BACKGROUND OF THE INVENTION

The delivery of gene editing tools is a key challenge for therapeutic application of such tools. There is a need in the art for safe and effective means of delivering gene editing tools to cells such that gene editing can be safely and effectively conducted in vivo or ex vivo.

SUMMARY OF THE INVENTION

The present disclosure provides delivery systems, compositions, methods, and kits for modifying a target nucleotide sequence in a subject. The disclosure provides for efficient in vivo gene editing and cellular DNA modification using nucleic acid editing systems such as CRISPR-Cas9, among others.

In one aspect, the present disclosure provides delivery systems comprising one or more guide RNA (gRNA) and a nucleic acid editing system. In one embodiment, the one or more gRNA is provided in a first delivery vehicle and the nucleic acid editing system is provided in a second delivery vehicle. In one embodiment, the delivery system further comprises a repair template, wherein the repair template is provided in the first, the second, or a third delivery vehicle.

In another aspect, the present disclosure provides delivery systems comprising (i) one or more gRNA covalently or noncovalently bound to a repair template and (ii) a nucleic acid editing system, wherein (i) and (ii) are present on the same or different delivery vehicles.

In another aspect, the present disclosure provides methods, kits, and compositions for modifying a target nucleotide sequence in a cell, comprising administering to the cell a delivery system comprising one or more gRNA and a nucleic acid editing system. In one embodiment, the delivery system comprises a first and second delivery vehicle as provided herein, wherein the first and second delivery vehicles are administered simultaneously or sequentially to the cell. In another embodiment, the one or more gRNA and/or the nucleic acid editing system is administered to the cell in a plurality of administrations.

In one embodiment, the target sequence is present in a target cell, and the target cell is present in a subject (i.e., in vivo). In another embodiment, the target cell has been isolated from a subject and is present ex vivo. In a further embodiment, the gRNA and nucleic acid editing system are administered to the cell ex vivo, and the ex vivo modified cell or cells may be re-introduced into the subject following ex vivo modification. In other embodiments, the target cell is in vitro.

In one embodiment, the subject is a mammal, such as a human, horse, cow, dog, cat, rodent, or pig. In particular embodiments, the subject is a human.

In one aspect, the present disclosure provides methods for treating a disease or disorder. In one embodiment, the disease or disorder is a genetic disease or disorder, a cancer, an inflammatory disease, or an infection, such as an infection with a virus. In a further embodiment, the methods provided herein achieve a therapeutic effect in a subject suffering from a genetic disease or disorder, an inflammatory disease, or an infection. In one embodiment, the methods provided herein achieve a target cell modification rate of about 0.01% to about 99%, or about 0.1% to about 50%, or about 1% to about 10%.

In one embodiment, the present disclosure provides delivery systems, compositions, methods, and kits for modifying a target nucleotide sequence, comprising at least one delivery vehicle, wherein the at least one delivery vehicle is a non-viral vector. In a further embodiment, the non-viral vector is a lipid-based or polymeric vector. Lipid-based or polymeric vectors may be selected, for example, from lipids, liposomes, lipid encapsulation systems, nanoparticles, small nucleic acid-lipid particle (SNALP) formulations, polymers, and polymersomes. In one embodiment, the polymer is selected from the group consisting of linear polymers, branched polymers, dendrimers, and polysaccharides. In another embodiment, the lipid encapsulation system comprises one or more of a phospholipid, cholesterol, polyethylene glycol (PEG)-lipid, and a lipophilic compound that delivers the particle to the target tissue. In a further embodiment, the lipophilic compound is C12-200 or cKK-E12. In one embodiment, the lipid encapsulation comprises 1,2-dioleoyl-sn-glycero-3-phosphoethanolamine (DOPE), cholesterol C14-PEG2000, and cKK-E12.

In one embodiment, the non-viral vector is biodegradable. In another embodiment, the non-viral vector comprises at least one cell-targeting or tissue-targeting ligand. In one embodiment, the non-viral vector has a size in the range of about 10 nm to about 10 μm, or about 20 nm to about 5 μm, or about 50 nm to about 500 nm, or about 50 nm to about 200 nm.

In one embodiment, the gRNA is delivered as an RNA conjugate. Thus, in one embodiment, the material conjugated to the gRNA acts as a non-viral delivery vehicle. RNA conjugates, in one embodiment, include RNA-GalNAc conjugates and dynamic polyconjugates. In one embodiment, the gRNA of the RNA conjugate is chemically modified.

In one embodiment, at least one delivery vehicle is a viral vector. Viral vectors, in one embodiment, may be selected from adeno-associated virus (AAV), adenovirus, retrovirus, and lentivirus vectors. In one embodiment, the viral vector is AAV 2/8.

In one aspect, the delivery system comprises a repair template. In one embodiment, the repair template is a DNA repair template, an mRNA repair template, an ssRNA repair template, an siRNA repair template, an miRNA repair template, or an antisense oligonucleotide repair template. In one embodiment, the repair template is a DNA repair template. In one embodiment, the length of the repair template is at least 200 bp, or is at least 500 bp, or is at least 800 bp, or is at least 1000 base pairs, or is at least 1500 base pairs. In one embodiment, the repair template is covalently or non-covalently bound to the gRNA or to the nucleic acid editing system. In a further embodiment, the repair template is partially annealed to the gRNA or to the nucleic acid editing system.

In one embodiment, the delivery system comprises a gRNA and a nucleic acid editing system, wherein the target sequence is recognized by the gRNA and modified by the nucleic acid editing system. In a further embodiment, the delivery system further comprises a repair template, and the target sequence is modified by the nucleic acid editing system and repair template. In one embodiment, the delivery system further comprises one or more reporter genes or epitope tags.

In one embodiment, the first delivery vehicle is a viral vector and the second delivery vehicle is a non-viral vector. In another embodiment, the first delivery vehicle is a non-viral vector and the second delivery vehicle is a viral vector. In one embodiment, the first or the second delivery vehicle further comprises a repair template. In one embodiment, the first delivery vehicle is a viral vector comprising a gRNA and a repair template, and the second delivery vehicle is a non-viral vector comprising a nucleic acid editing system. In one embodiment, the gRNA is delivered via an RNA conjugate, and the nucleic acid editing system is delivered via a non-viral vector such as a nanoparticle. In another embodiment, the first and second delivery vehicles are both non-viral vectors, or are both viral vectors.

In one embodiment, the nucleic acid editing system is selected from the group consisting of ZFPs, TALEs, and CRISPR systems. In a further embodiment, the nucleic acid editing system is a CRISPR-Cas system such as, for example, Cas9.

In one embodiment, the gRNA is expressed under the control of an inducible promoter. In another embodiment, the gRNA is expressed under the control of a viral promoter. In another embodiment, the gRNA is expressed under the control of a tissue-specific promoter. For example, in one embodiment, the promoter induces expression in one or more of liver, heart, lung, skeletal muscle, CNS, endothelial cells, stem cell, blood cell or blood cell precursor, and immune cells. Promoters may be selected from the group consisting of U6, CMV, SV40, EF-1α, Ubc, PGK, or small molecule-inducible promoters, or other promoters known in the art.

In one embodiment, the gRNA and/or the RNA encoding the nucleic acid editing system is chemically modified. Chemical modifications of RNA may include modifications of the phosphate backbone (e.g., phosphorothioate linkages or boranophosphate linkages), ribose ring modifications such as 2'-O-methyl and/or 2'-fluoro and/or 4'-thio modifications, and locked or unlocked nucleic acids. Other modifications may include pseudouridine, 2-thiouridine, 4-thiouridine, 5-azauridine, 5-hydroxyuridine, 5-aminouridine, 5-methyluridine, 2-thiopseudouridine, 4-thiopseudouridine, 5-hydroxypseudouridine, 5-methylpseudouridine, 5-aminopseudouridine, pseudoisocytidine, 5-methylcytidine, N4-methylcytidine, 2-thiocytidine, 5-azacytidine, 5-hydroxycytidine, 5-aminocytidine, N4-methylpseudoisocytidine, 2-thiopseudoisocytidine, 5-hydroxypseudoiocytidine, 5-aminopseudoisocytidine, 5-methylpseudoisocytidine, N6-methyladenosine, 7-deazaadenosine, 6-thioguanosine, 7-deazaguanosine, 8-azaguanosine, 6-thio-7-deazaguanosine, 6-thio-8-azaguanosine, 7-deaza-8-azaguanosine, and 6-thio-7-deaza-8-azaguanosine.

In one embodiment, the gRNA is capable of hybridizing to a target sequence in a cell. In a further embodiment, the target sequence is located in the nucleus or cytoplasm of the cell.

In one embodiment, the target sequence is associated with a genetic disease or disorder. Genetic diseases and disorders may be inborn errors of metabolism selected from disorders of amino acid transport and metabolism, lipid or fatty acid transport and metabolism, carbohydrate transport and metabolism, and metal transport and metabolism. In one embodiment, the genetic disease or disorder is associated with a genetic variant selected from a single-nucleotide polymorphism (SNP), substitution, insertion, deletion, transition, transversion, translocation, nonsense, missense, and frameshift mutation. In one embodiment, the genetic disorder is hemophilia, cystic fibrosis, or sickle cell disease. In another embodiment, the target sequence is a virus or a provirus sequence. For example, in one embodiment, the target sequence is a human immunodeficiency virus (HIV) or human T-lymphotrophic virus (HTLV) sequence. In one embodiment, the target sequence is associated with cancer. In a further embodiment, the target sequence is a tumor driver gene. In one embodiment, the target sequence is a gene associated with immune suppression in cancer.

In one aspect, the present disclosure provides kits and compositions, wherein the kits and compositions comprise (i) one or more gRNA in a first delivery vehicle and (ii) a nucleic acid editing system in a second delivery vehicle. In one embodiment, the kits and compositions further comprise a repair template. In a further embodiment, the repair template is covalently or noncovalently bound to the gRNA.

In one aspect, the present disclosure provides methods for modifying a target nucleotide sequence in a cell or a subject, comprising administering to the cell or subject a delivery system, wherein the delivery system provides for temporally controlled expression of a gRNA in a target tissue as well as temporally controlled expression of a nucleic acid editing system in the target tissue, wherein the gRNA directs cleavage of the target nucleic acid sequence in the target tissue by the nucleic acid editing system. In one embodiment, the delivery system provides a gRNA and a nucleic acid editing system, and further provides a DNA repair template, wherein the gRNA directs cleavage of the target nucleic acid sequence in the target tissue and repair of the target sequence by the repair template.

In one embodiment, the gRNA is expressed in the cell prior to the nucleic acid editing system. In another embodiment, the nucleic acid editing system is expressed transiently in the cell. In one embodiment, the gRNA is delivered to the target cell or tissue in an AAV vector and the nucleic acid editing system is delivered to the target cell or tissue in a lipid-based delivery vehicle, wherein the gRNA is delivered to the cell or tissue prior to the nucleic acid editing system. In a further embodiment, the gRNA is delivered to the cell or tissue about 1, 2, 3, 4, 5, 6, 7, 8, 9, 10, 11, 12, 13, 14, or more days prior to the delivery of the nucleic acid editing system. In another embodiment, the gRNA and/or the nucleic acid editing system is administered to the target cell or tissue in a plurality of administrations. For example, in one embodiment, the nucleic acid editing system is delivered to the target cell or tissue in from about 2 to about 20 administrations. In one embodiment, the nucleic acid editing system is administered in a lipid-based delivery vehicle about 7 days and about 14 days after the administration of the one or more gRNA in an AAV vector. In one embodiment, the nucleic acid editing system is delivered to the target cell or tissue over a time period of from about 1 week to about 6 months, such as from about 2 to about 10 doses within about 2 months, or from about 3 to about 5 doses over about 1 month.

In one embodiment, the gRNA is expressed in the target cell or tissue for about 2 weeks, 3 weeks, 4 weeks, 5 weeks, 6 weeks, 7 weeks, 8 weeks, 9 weeks, 10 weeks, 11 weeks, 12 weeks, or more. In another embodiment, the nucleic acid editing system is expressed in the target cell or tissue transiently. In a further embodiment, the nucleic acid editing system is expressed in the target cell or tissue for less than a month, less than 3 weeks, less than 2 weeks, less than 1 week, less than 5 days, or less than 3 days. For example, in one embodiment, the nucleic acid editing system is expressed in the target tissue for about 1 day to about 5 days, or for about 1 day to about 3 days. Thus, the vehicle providing for expression of the gRNA(s) and optional presence of the DNA repair template provides a window of time in which a nucleic acid editing system can be administered (once or a plurality of times) to provide transient expression of the editing system (e.g., nuclease), as well as a level of tissue-specific expression in some embodiments, thereby directing editing of the cellular DNA.

The delivery systems and compositions disclosed herein may be administered by injection, optionally by direct injection to target tissues.

In one embodiment, the delivery systems and compositions disclosed herein may be administered to a subject in more than one dose. In one embodiment, the nucleic acid editing system is administered to the subject in a non-viral delivery vehicle (e.g., a lipid-based delivery vehicle) in more than one dose.

BRIEF DESCRIPTION OF THE DRAWINGS

FIG. 2A is a schematic depiction of the Cas9 mRNA packing into the lipid nanoparticle cKK-E12. FIG. 2B is a Western blot showing expression of Cas9 mRNA (containing a human influenza hemagglutinin (HA) tag) in liver tissue from FVB/N mice injected with the lipid nanoparticle comprising the Cas9 mRNA.

FIGS. 3A (low resolution) and 3B (high resolution) show FAH expression at Day 21 in the liver of FAH mutant mice that had received the AAV 2/8 delivery vehicle on Day 0, and at Day 7 and Day 14 received 1 mg/kg of the lipid nanoparticle encapsulated Cas9 mRNA (or PBS as a control). The left panels of FIGS. 3A and 3B show FAH expression from mice that received the AAV 2/8 delivery vehicle only. The right panels of FIGS. 3A and 3B show FAH expression in mice that received the AAV 2/8 delivery vehicle and the lipid nanoparticle delivery vehicle.

FIGS. 8A-8E show that in vitro delivery data of Cas9 mRNA mediates efficient genome editing in cells. FIG. 8A: C12-200 lipid nanoparticle delivery of Cas9 mRNA into cells. 293T cells stably expressing EF1a promoter-GFP and U6 promoter-GFP targeting sgRNA (sgGFP) were incubated with Cas9 mRNA nanoparticles (nano.Cas9). Cas9-mediated frameshift NHEJ events will result in GFP-negative cells. Red arrowhead indicates the Cas9 cutting site. FIG. 8B: FACS analysis shows that Cas9 mRNA generates GFP-cells. Gate R2 indicates 80% GFP-cells after nano.Cas9 treatment. FIG. 8C: GFP locus was deep sequenced in nano.Cas9 treated cells (n=2). Shown are representative indels. FIG. 8D: Distribution of indels. FIG. 8E: Indel phase shows that most indels cause frameshift. For example, 3N+1 include 1-, 4- and 7-bp indels, 3N+2 include 2-, 5- and 8-base-pair indels and 3-, 6- and 9-base-pair indels are 3N.

FIG. 9A: Design of dual function AAV-sgRNA-HDR template (AAV-HDR). A G→A point mutation at the last nucleotide of exon 8 in Fah$^{mut/mut}$ homozygous mice leads to splicing skipping of exon 8. A dual function AAV vector harbors U6-sgRNA and a HDR template (1.7kb) with the "G" nucleotide to repair the "A" mutation. The "TGG" PAM was modified to "TCC" to preventing self-cleavage. Dashed lines denote homozygous recombination. ITR, inverted terminal repeat. FIG. 9B: Fah$^{mut/mut}$ mice were injected with AAV-HDR and nano.Cas9 at indicated time points. Mice were kept off NTBC water at D0. Body weight normalized to pre-injection was monitored over time. FIG. 9C: AAV-HDR and nano.Cas9 fully rescues weight loss upon NTBC withdrawal. FIG. 9D: Liver damage markers (aspartate aminotransferase (AST), alanine aminotransferase (ALT) and bilirubin) were measured in serum. Error bars, mean±s.e.m. FIG. 9E: FAH+ cells after 30 Days off NTBC. Arrow Bar indicates 100 uM FIGS. 10A-10F provide in vivo delivery of Cas9 mRNA and AAV corrects Fah mutation.

FIG. 11A: nano.Cas9 formulation scheme. Cas9 mRNA was mixed with C12-200, DOPE, Cholesterol and C14PEG2000 in a microfluidic chamber. FIG. 11B: nano.Cas9 structure is characterized by cryo-TEM. Scale bar indicates 100 nm. FIG. 11C: Average diameter of nano.Cas9 was measured by dynamic light scattering. The size of nano.Cas9 FIG. 11D and the polydispersity index (PDI) FIG. 11E were measured 0, 7, 11 or 18 days after formulation and storage at 4° C.

FIG. 12A: C57bl/6 mice were i.v. injected with nanoparticles encapsulated with β-gal (B and C) or Cas9 mRNA (nano.Cas9, D and E), and livers taken. FIG. 12B: The expression of β-gal protein is measured in liver lysate at 14 hours after injection. FIG. 12C: The activity of β-gal in liver sections was determined by salmon-gal assay. Scale bar indicates 200 µm. FIG. 12D: The Cas9 mRNA level in liver lysate was determined by qRT-PCR at 4, 14, and 24 hrs after injection. FIG. 12E: The expression of Cas9 protein was measured in liver lysate 14 hours after injection. 10, 1 or 0.1 ng Cas9 protein mixed into 50 µg negative control samples were served as positive controls.

FIG. 13A: 293T cells were transfected with Cas9 mRNA with Lipo2000 or nano.Cas9, and cellular viability was determined 48 hrs later (B-D). C57/B16 mice were treated with 2 mg/kg nano.Cas9, and histology FIG. 13B, liver damage enzymes FIG. 13C and plasma cytokines FIG. 13D were determined after 24 hrs. Scale bar indicates 50 µm.

DETAILED DESCRIPTION

Figure 1:
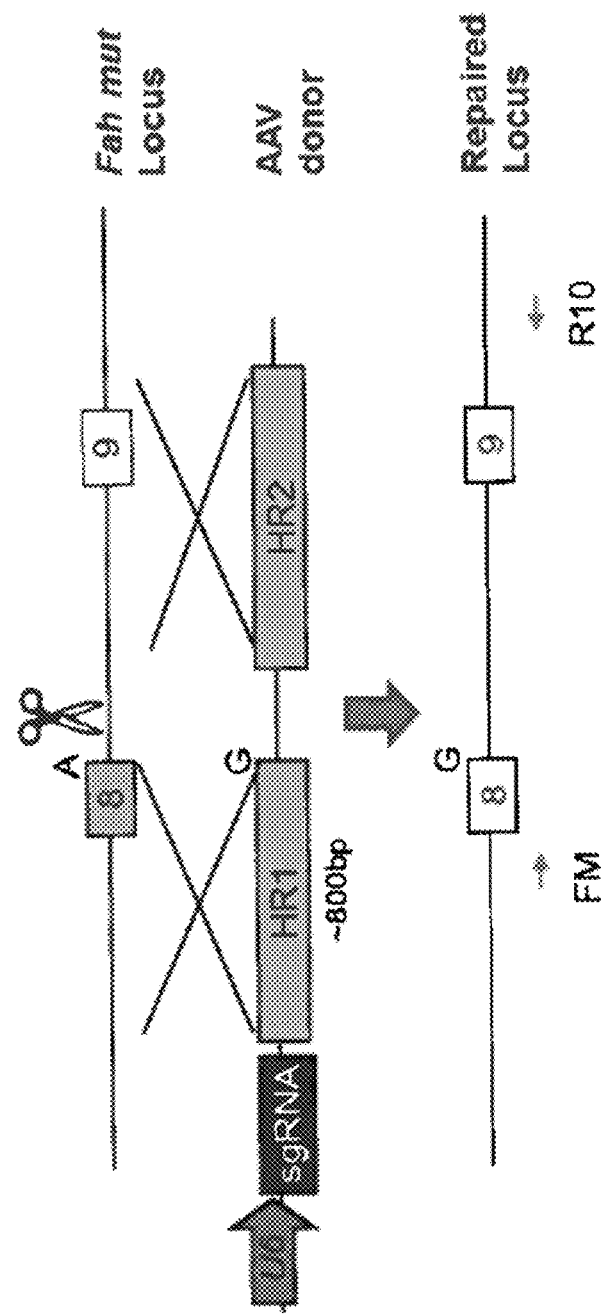
FIG. 1 is a schematic depiction of the repair of a Fumarylacetoacetate hydrolase (FAH) mutation, which is a mouse model for the human disease tyrosinemia I. The sgRNA targeting the region of the FAH mutation is expressed through a U6 promoter in the AAV 2/8 vector. A repair template is also provided in the vector.

The term "about", as used herein, refers to plus or minus ten percent of the object that "about" modifies.

The present disclosure provides delivery systems, compositions, methods, and kits for modifying a target nucleotide sequence in a cell. In some embodiments, the delivery systems comprise one or more guide RNA (gRNA) and a nucleic acid editing system. The gRNA works in tandem with the nucleic acid editing system to localize to and edit the target cellular nucleotide sequence. The delivery systems, compositions, methods, and kits provided herein allow for temporally controlled expression of the gRNA and the nucleic acid editing system. Optionally, a repair template may be included to replace the target nucleotide sequence thus effecting either repair of a gene defect or knock-in of a selected sequence. In particular aspects, the nucleic acid editing system is a CRISPR-Cas9 system. The CRISPR (clustered regularly interspersed short palindromic repeats)/Cas9 system has emerged as a genetic editing tool, as disclosed in, for example Cong et al. *Multiplex genome engineering using CRISPR/Cas systems. Science.* 339:819-823 (2013); Doudna and Charpentier. *Genome editing. The new frontier of genome engineering with CRISPR-Cas9. Science.* 346:1258096 (2014); Mali et al. *RNA-guided human genome engineering via Cas9. Science.* 339:823-826. (2013). CRISPR-Cas9 has been employed to edit genomes of various model organisms such as bacteria, yeast, *C. elegans, Drosophila*, plants, zebrafish, and mouse and human cells, as disclosed in, for example, Mali et al. *Cas9 as a versatile tool for engineering biology,* Nat. Methods. 10:957-963 (2013).

Cas9/sgRNA recognizes the protospacer-adjacent motif (PAM) sequence and the complementary 20 nucleotide genomic sequence. Cas9 cuts approximately 3 nucleotides upstream of the PAM to induce double stranded DNA breaks (DSBs), which are repaired by error-prone non-homologous end-joining (NHEJ) or precise homology-directed repair (HDR), as disclosed in, for example, Doudna and Charpentier (2014); and Sander and Joung. *CRISPR-Cas systems for editing, regulating and targeting genomes. Nat. Biotechnol.* 32:347-355 (2014). Improvements to CRISPR delivery methods and HDR efficiency are needed in the field for therapeutic application of genome editing for disease gene correction.

Nucleic Acid Editing Systems

Cas9 (CRISPR associated protein 9) is an RNA-guided DNA nuclease enzyme associated with *Streptococcus pyogenes* CRISPR immunity system. Cas9 can be used to induce site-directed double strand breaks in DNA, which can lead to gene inactivation or the introduction of heterologous genes through non-homologous end joining and homologous recombination respectively. mRNA systems for expressing Cas9 are commercially available from TriLink Biotechnologies (San Diego, Calif.). The mRNA may be codon optimized for human or other mammalian system. The expressed Cas9 protein may contain a nuclear localization signal at the C-terminus. The RNA encoding Cas9 may be capped and polyadenylated to support expression in mammalian cells, and may contain modifications to reduce immune stimulation. The amino acid sequence and encoding nucleic acid sequence for Cas9 and functional derivatives and homologs (which can be used in accordance with the disclosure) include those described in U.S. Pat. No. 8,697,359, which is hereby incorporated by reference in its entirety.

The Cas9 may be delivered in conjunction with a gRNA, which directs the Cas9 editing system to the nucleotide sequence recognized by the gRNA. The term "gRNA" is used interchangeably herein with "gRNA" "single gRNA," and "sgRNA." In general, a gRNA can be designed to target any nucleotide sequence. The gRNA structure is disclosed in, for example, Ran F A, *Genome editing using the CRISPR-Cas9 System*, PNAS 8(11):2281-308 (2013); and Pyzocha et al., *RNA-guided genome editing of mammalian cells, Methods Mol. Biol.* 1114:269-77 (2014), which are hereby incorporated by reference in their entirety. Generally for Cas9, gRNAs guide the Cas9 endonuclease to the complementary 20 nucleotide (nt) genomic sequences with a downstream NGG protospacer-adjacent motif (PAM). Cas9 generates double-stranded breaks, which can be repaired by non-homologous end-joining (NHEJ) or homologous recombination (HR). See, for example, US 2014/0017212, which is hereby incorporated by reference in its entirety.

The CRISPR-Cas9 system including the construction of guide sequences is further disclosed in U.S. Pat. No. 8,697,359, which is hereby incorporated by reference in its entirety. In some embodiments, a Cas9 nickase version is employed. Cas9 nickase can generate single stranded breaks, and a double nickase can generate double stranded breaks. The nickase can provide for reduced off-target effects. Further, by delivering two gRNAs and a Cas9 nickase, off target effects can be further reduced. See Shen et al., *Efficient genome modification by CRISPR-Cas9 nickase with minimal off-target effects, Nature Methods* 11:399-402 (2014).

In place of a CRISPR-Cas9 system, alternate nucleic acid editing systems may be used. For example, suitable systems include any CRISPR/cas system (e.g., any Cascade-like CRISPR/cas, Type I CRISPR/cas, Type II CRISPR/cas, and type III CRISPR/cas), zinc finger nucleases (ZFNs), transcription activator-like effector nucleases (TALENs), and engineered meganuclease re-engineered homing endonucleases.

RNA encoding the nucleic acid editing system can be modified, and the modification selected from one or more of modifications of the phosphate backbone (e.g., phosphorothioate linkages or boranophosphate linkages), ribose ring modifications such as 2'-O-methyl and/or 2'-fluoro and/or 4'-thio modifications, and locked or unlocked nucleic acids. Other modifications may include pseudouridine, 2-thiouridine, 4-thiouridine, 5-azauridine, 5-hydroxyuridine, 5-aminouridine, 5-methyluridine, 2-thiopseudouridine, 4-thiopseudouridine, 5-hydroxypseudouridine, 5-methylpseudouridine, 5-aminopseudouridine, pseudoisocytidine, 5-methylcytidine, N4-methylcytidine, 2-thiocytidine, 5-azacytidine, 5-hydroxycytidine, 5-aminocytidine, N4-methylp-seudoisocytidine, 2-thiopseudoisocytidine, 5-hydroxypseudoisocytidine, 5-aminopseudoisocytidine, 5-methylpseudoisocytidine, N6-methyladenosine, 7-deazaadenosine, 6-thioguanosine, 7-deazaguanosine, 8-azaguanosine, 6-thio-7-deazaguanosine, 6-thio-8-azaguanosine, 7-deaza-8-azaguanosine, and 6-thio-7-deaza-8-azaguanosine. Generally, modifications are selected to reduce immune stimulation and stabilize the RNA and improve expression of the encoded protein. For example, the RNA may have a combination of 2-thiouridine and 5-methyl-cytidine, which has been shown to reduce immune stimulation through pattern recognition receptors, such as TLR3, TLR7, TLR8 and RIG-I (retinoic-acid-inducible protein I). In some embodiments, the mRNA has one or more pseudouridine (preventing activation of pattern recognition receptors and 2'-5'-oligoadenylate synthetase). These modifications can also stabilize the mRNA against cleavage, and ultimately improve expression rates.

Delivery Systems

The efficient delivery of nucleic acid editing systems, including the CRISPR-Cas9 system, provide for safer and more effective delivery systems, which are especially useful in the clinical setting. The delivery systems herein disclose methods and compositions containing viral and/or non-viral vectors to deliver nucleic acid editing systems, particularly, CRISPR-Cas9 system, and optionally an editing template to edit genes in cells. While gene editing is particularly useful in vivo, in some embodiments, the cell targeted for gene editing may be in vitro, ex vivo, or in vivo.

Delivery Vehicles

The delivery vehicles provided herein may be viral vectors or non-viral vectors, or RNA conjugates. In some embodiments, the gRNA and the nucleic acid editing system are provided in the same type of delivery vehicle, wherein the delivery vehicle is a viral vector or a non-viral vector. In other embodiments, the gRNA is provided in a viral vector, and the nucleic acid editing system is provided in a non-viral vector. In still other embodiments, the one or more gRNA is provided in a non-viral vector and the nucleic acid editing system is provided in a viral vector. In some embodiments, the gRNA is provided in an RNA conjugate.

Viral Vectors

In some embodiments, the viral vector is selected from an adeno-associated virus (AAV), adenovirus, retrovirus, and lentivirus vector. While the viral vector may deliver any component of the system described herein so long as it provides the desired profile for tissue presence or expression, in some embodiments the viral vector provides for expression of the gRNA and optionally delivers a repair template. In some embodiments, the viral delivery system is adeno-associated virus (AAV) 2/8. However, in various embodiments other AAV serotypes are used, such as AAV1, AAV2, AAV4, AAV5, AAV6, and AAV8. In some embodiments, AAV6 is used when targeting airway epithelial cells, AAV7 is used when targeting skeletal muscle cells (similarly for AAV1 and AAV5), and AAV8 is used for hepatocytes. In some embodiments, AAV1 and 5 can be used for delivery to vascular endothelial cells. Further, most AAV serotypes show neuronal tropism, while AAV5 also transduces astrocytes. In some embodiments, hybrid AAV vectors are employed. In some embodiments, each serotype is administered only once to avoid immunogenicity. Thus, subsequent administrations employ different AAV serotypes. Additional viral vectors that can be employed are as described in U.S. Pat. No. 8,697,359, which is hereby incorporated by reference in its entirety.

Non-Viral Vectors

In some embodiments, the delivery system comprises a non-viral delivery vehicle. In some aspects, the non-viral delivery vehicle is lipid-based. In other aspects, the non-viral delivery vehicle is a polymer. In some embodiments, the non-viral delivery vehicle is biodegradable. In embodiments, the non-viral delivery vehicle is a lipid encapsulation system and/or polymeric particle.

Lipid-Based and Polymeric Non-Viral Vectors

In certain embodiments, the delivery system comprises lipid particles as described in Kanasty R, *Delivery materials for siRNA therapeutics Nat Mater.* 12(11):967-77 (2013), which is hereby incorporated by reference. In some embodiments, the lipid-based vector is a lipid nanoparticle, which is a lipid particle between about 1 and about 100 nanometers in size.

In some embodiments, the lipid-based vector is a lipid or liposome. Liposomes are artificial spherical vesicles comprising a lipid bilayer.

In some embodiments, the lipid-based vector is a small nucleic acid-lipid particle (SNALP). SNALPs comprise small (less than 200 nm in diameter) lipid-based nanoparticles that encapsulate a nucleic acid. In some embodiments, the SNALP is useful for delivery of an RNA molecule such as siRNA. In some embodiments, SNALP formulations deliver nucleic acids to a particular tissue in a subject, such as the liver.

In some embodiments, the gRNA and/or nucleic acid editing system (or the RNA encoding the same) is delivered via polymeric vectors. In some embodiments, the polymeric vector is a polymer or polymerosome. Polymers encompass any long repeating chain of monomers and include, for example, linear polymers, branched polymers, dendrimers, and polysaccharides. Linear polymers comprise a single line of monomers, whereas branched polymers include side chains of monomers. Dendrimers are also branched molecules, which are arranged symmetrically around the core of the molecule. Polysaccharides are polymeric carbohydrate molecules, and are made up of long monosaccharide units linked together. Polymersomes are artificial vesicles made up of synthetic amphiphilic copolymers that form a vesicle membrane, and may have a hollow or aqueous core within the vesicle membrane.

Various polymer-based systems can be adapted as a vehicle for administering RNA encoding the nucleic acid editing machinery. Exemplary polymeric materials include poly(D,L-lactic acid-co-glycolic acid) (PLGA), poly(caprolactone) (PCL), ethylene vinyl acetate polymer (EVA), poly(lactic acid) (PLA), poly(L-lactic acid) (PLLA), poly(glycolic acid) (PGA), poly(L-lactic acid-co-glycolic acid) (PLLGA), poly(D,L-lactide) (PDLA), poly(L-lactide) (PLLA), PLGA-b-poly(ethylene glycol)-PLGA (PLGA-bPEG-PLGA), PLLA-bPEG-PLLA, PLGA-PEG-maleimide (PLGA-PEG-mal), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride)

(PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth) acrylate), poly(butyl(meth)acrylate), poly(isobutyl(meth) acrylate), poly(hexyl(meth)acrylate), poly(isodecyl(meth) acrylate), poly(lauryl(meth)acrylate), poly(phenyl(meth) acrylate), poly(methyl acrylate), poly(isopropyl acrylate), poly(isobutyl acrylate), poly(octadecyl acrylate) (polyacrylic acids), and copolymers and mixtures thereof, polydioxanone and its copolymers, polyhydroxyalkanoates, polypropylene fumarate), polyoxymethylene, poloxamers, poly (ortho)esters, poly(butyric acid), poly(valeric acid), poly (lactide-co-caprolactone), trimethylene carbonate, polyvinylpyrrolidone, polyorthoesters, polyphosphazenes, Poly([beta]-amino esters (PBAE), and polyphosphoesters, and blends and/or block copolymers of two or more such polymers. Polymer-based systems may also include Cyclodextrin polymer (CDP)-based nanoparticles such as, for example, CDP-admantane (AD)-PEG conjugates and CDP-AD-PEG-transferrin conjugates.

Exemplary polymeric particle systems for delivery of drugs, including nucleic acids, include those described in U.S. Pat. Nos. 5,543,158, 6,007,845, 6,254,890, 6,998,115, 7,727,969, 7,427,394, 8,323,698, 8,071,082, 8,105,652, US 2008/0268063, US 2009/0298710, US 2010/0303723, US 2011/0027172, US 2011/0065807, US 2012/0156135, US 2014/0093575, WO 2013/090861, each of which are hereby incorporated by reference in its entirety.

In one embodiment, nanoparticles are formulated with Cas9 mRNA chemically modified to reduce TLR responses, as disclosed in Kormann et al. *Expression of therapeutic proteins after delivery of chemically modified mRNA in mice. Nat. Biotechnol.* 29:154-157 (2011). In a further embodiment, the nanoparticles are formulated using controlled microfluidic mixing systems, as disclosed in, for example, Chen et al. *Rapid discovery of potent siRNA-containing lipid nanoparticles enabled by controlled microfluidic formulation. J. Amer. Chem. Soc.* 134:6948-6951 (2012).

In one embodiment, the delivery system is a layer-by-layer particle system comprising two or more layers. In a further embodiment, the guide RNA and the nucleic acid editing system are present in different layers within the layer-by-layer particle. In a yet further embodiment, the guide RNA and nucleic acid editing system may be administered to a subject in a layer-by-layer particle system such that the release of the guide RNA and nucleic acid editing system from the particles can be controlled in a cell-specific and/or temporal fashion. In one embodiment, the layer-by-layer particle system is designed to allow temporally controlled expression of the guide RNA and the nucleic acid editing system as disclosed herein. Layer-by-layer particle systems are disclosed, for example, in 2014/0093575, incorporated herein by reference in its entirety.

Lipid Encapsulation System Vectors

In some embodiments, the lipid-based delivery system comprises a lipid encapsulation system. The lipid encapsulation system can be designed to drive the desired tissue distribution and cellular entry properties, as well as to provide the requisite circulation time and biodegrading character. The lipid encapsulation may involve reverse micelles and/or further comprise polymeric matrices, for example as described in U.S. Pat. No. 8,193,334, which is hereby incorporated by reference. In some embodiments, the particle includes a lipophilic delivery compound to enhance delivery of the particle to tissues, including in a preferential manner. Such compounds are disclosed in US 2013/0158021, which is hereby incorporated by reference in its entirety. Such compounds may generally include lipophilic groups and conjugated amino acids or peptides, including linear or cyclic peptides, and including isomers thereof. An exemplary compound is referred to as cKK-E12, which can affect delivery to liver and kidney cells, for example. The present disclosure can employ compounds of formulas (I), (II), (III), IV), (V), and (VI) of US 2013/0158021. Compounds can be engineered for targeting to various tissues, including pancreas, spleen, liver, fat, kidneys, uterus/ovaries, muscle, heart, lungs, endothelial tissue, and thymus.

In some embodiments, the lipid encapsulation comprises one or more of a phospholipid, cholesterol, polyethylene glycol (PEG)-lipid, and a lipophilic compound. In some embodiments, the lipophilic compound is C12-200, particularly in embodiments that target the liver. (Love et al., *Lipid-like materials for low-dose, in vivo gene silencing PNAS* 107(21) (2010), incorporated herein by reference in its entirety. In other embodiments, the lipophilic compound C12-200 is useful in embodiments that target fat tissue. In still other embodiments, the lipopeptide is cKK-E12. Dong, et al., *PNAS.* 111(11):3955-3960 (2014), incorporated herein by reference in its entirety.

In some embodiments, the lipid encapsulation comprises 1,2-dioleoyl-sn-glycero-3-phosphoethanolamine (DOPE), cholesterol, C14-PEG2000, and cKK-E12, which as disclosed herein provides for efficient in vivo editing in liver tissue. An illustration of such a particle is shown in FIG. 2A-B.

Additional Components and Features of Non-Viral Vectors

The particles, whether lipid or polymeric or both, may include additional components useful for enhancing the properties for in vivo nucleic acid delivery (including compounds disclosed in U.S. Pat. No. 8,450,298 and US 2012/0251560, which are each hereby incorporated by reference).

The delivery vehicle may accumulate preferentially in certain tissues thereby providing a tissue targeting effect, but in some embodiments, the delivery vehicle further comprises at least one cell-targeting or tissue-targeting ligand. Functionalized particles, including exemplary targeting ligands, are disclosed in US 2010/0303723 and 2012/0156135, which are hereby incorporated by reference in their entireties.

A delivery vehicle can be designed to drive the desired tissue distribution and cellular entry properties of the delivery systems disclosed herein, as well as to provide the requisite circulation time and biodegrading character. For example, lipid particles can employ amino lipids as disclosed US 2011/0009641, which is hereby incorporated by reference.

The lipid or polymeric particles may have a size (e.g., an average size) in the range of about 50 nm to about 5 µm. In some embodiments, the particles are in the range of about 10 nm to about 100 µm, or about 20 nm to about 50 µm, or about 50 nm to about 5 µm, or about 70 nm to about 500 nm, or about 70 nm to about 200 nm, or about 50 nm to about 100 nm. Particles may be selected so as to avoid rapid clearance by the immune system. Particles may be spherical, or non-spherical in certain embodiments.

In some embodiments, the non-viral delivery vehicle may be a peptide, such as a cell-penetrating peptides or cellular internalization sequences. Cell penetrating peptides are small peptides that are capable of translocating across plasma membranes. Exemplary cell-penetrating peptides include, but are not limited to, Antennapedia sequences, TAT, HIV-Tat, Penetratin, Antp-3A (Ante mutant), Buforin II, Transportan, MAP (model amphipathic peptide), K-FGF, Ku70, Prion, pVEC, Pep-1, SynB1, Pep-7, I-IN-1, BGSC (Bis-Guanidinium-Spermidine-Cholesterol, and BGTC (Bis-Guanidinium-Tren-Cholesterol).

Chemical Modification of RNA and RNA Conjugates

In some embodiments, the gRNA is chemically modified. In other embodiments, the gRNA is conjugated to a material to aid in delivery of the RNA to the target tissue or cell. Thus, in some embodiments, the material to which the gRNA is conjugated acts as a gRNA delivery vehicle. In further embodiments, the gRNA of the RNA conjugate is chemically modified. Any chemical modification or conjugate material may be used in the delivery systems, methods, and compositions provided herein, including those chemical modifications and conjugate materials disclosed in Kanasty et al., *Nature Materials* 12; 967 (2013).

Chemical modification of the RNA molecule may stabilize the molecule prior to reaching the target cell (e.g., in the bloodstream), reduce immunogenicity of the RNA molecule, and improve delivery to the target cell and/or improve entry into the target cell. Chemical modifications of RNAs are known in the art, for example, in Kanasty et al., *Nature Materials* 12; 967 (2013) and Corey, D R. *Journal of Clinical Investigation* 117; 3615 (2007), each of which is incorporated herein by reference in its entirety. Chemical modifications of RNA may include modifications of the phosphate backbone (e.g., phosphorothioate linkages or boranophosphate linkages), ribose ring modifications such as 2'-O-methyl and/or 2'-fluoro and/or 4'-thio modifications, and locked or unlocked nucleic acids. Other modifications may include pseudouridine, 2-thiouridine, 4-thiouridine, 5-azauridine, 5-hydroxyuridine, 5-aminouridine, 5-methyluridine, 2-thiopseudouridine, 4-thiopseudouridine, 5-hydroxypseudouridine, 5-methylpseudouridine, 5-aminopseudouridine, pseudoisocytidine, 5-methylcytidine, N4-methylcytidine, 2-thiocytidine, 5-azacytidine, 5-hydroxycytidine, 5-aminocytidine, N4-methylpseudoisocytidine, 2-thiopseudoisocytidine, 5-hydroxypseudoisocytidine, 5-aminopseudoi socytidine, 5-methylpseudoi socytidine, N6-methyladenosine, 7-deazaadenosine, 6-thioguanosine, 7-deazaguanosine, 8-azaguanosine, 6-thio-7-deazaguanosine, 6-thio-8-azaguanosine, 7-deaza-8-azaguanosine, and 6-thio-7-deaza-8-azaguanosine.

In some embodiments, the RNA molecule is modified at the 5' end (e.g., the 20-25 nucleotides at the amino terminus, the middle portion of the RNA (e.g., the Cas9 binding portion, which is about 42 nucleic acids long), or the 3' end (e.g., the 30-35 nucleic acids at carboxy terminus of the RNA). In a preferred embodiment, the modification is made at the 3' end of the RNA.

The RNA may be conjugated to cholesterol, other lipophilic molecules, polymers, peptides, antibodies, aptamers, and/or small molecules. In some embodiments, the RNA is conjugated to a N-acetylgalactosamine (GalNAc). GalNAc binds the asialoglycoprotein receptor (ASGPR) on hepatocytes, and therefore can be used to target an RNA to the liver. In some embodiments, the RNA is conjugated to a trivalent targeting ligand, e.g., triantennary GalNAc. Such conjugates comprise an RNA conjugated at the 3' terminus to three GalNAc molecules. Exemplary RNA-GalNAc conjugates are disclosed, for example, in Kanasty et al., *Nature Materials* 12; 967 (2013), incorporated herein by reference in its entirety.

In one embodiment, the conjugate delivery system is a dynamic polyconjugate (DPC) system. In one embodiment, a DPC comprises a membrane-disrupting polymer linked to the RNA molecule via linker such as a hydrolysable disulphide linker. The membrane-disrupting polymer may be poly(butyl amino vinyl ether; PBAVE). In a further embodiment, PEG side chains are linked to the polymer backbone. In one embodiment, the PEG side chains mask the polymer and induce uptake by a target cell (via receptor-mediated endocytosis), after which PEG is shed in the endosome, exposing the membrane-disrupting polymer and triggering release from the endosome. After endosomal release, the linker is cleaved (e.g., disuphide cleavage in the cytosol) and the RNA is released into the cell. In some embodiments, the membrane-disrupting polymer further is attached to a targeting ligand such as, for example, GalNAc. In one embodiment, the RNA molecule in the DPC system is chemically modified according to the chemical modifications disclosed herein.

Duration of Expression

In some aspects, the delivery vehicle for the gRNA is selected such that the gRNA is expressed in the target tissue for at least 1 week. However, longer expression will be desired in some embodiments, such as expression in the target tissue for at least 2 weeks, 3 weeks, or at least 4 weeks, or at least 5 weeks, or at least 6 weeks, or at least 7 weeks, or at least 8 weeks, or for at least 2 months, at least 3 months, at least 4 months, at least 6 months, at least 8 months, at least 10 months, at least 12 months, at least 18 months, at least 24 months, or more. In some embodiments, the length of time of expression of the gRNA provides a window in which an editing system is provided to the cells to effect the nucleic acid modification.

In some embodiments, the delivery systems, compositions, methods, and kits provided herein provide transient expression of the nucleic acid editing system (e.g., Cas9) in the target cell. In some embodiments, such transient expression helps to minimize off-target effects and/or immunogenicity. For example, in one embodiment, the delivery systems, compositions, methods, and kits provided herein provide expression of the nucleic acid editing system such as Cas9 in a cell for about two weeks or less, or for about 1 week or less. In some embodiments, the compositions and delivery systems provided herein provide expression of the nucleic acid editing system such as Cas9 in a cell for about 1 day to about 5 days, or for about 1 day to about 3 days.

The timing and type of expression of the gRNA and/or nucleic acid editing system such as Cas9 can be varied, such as through tissue-specific promoters, constitutive promoters or inducible promoters. As used herein, an inducible promoter is any promoter whose activity is regulated upon the application of an agent, such as a small molecule, to the cell. For example, inducible promoters include tetracycline-regulatable or doxycycline-regulatable promoters, carbohydrate-inducible or galactose-inducible promoters, isopropyl-beta-D-thiogalactopyranoside (IPTG)-regulated promoters, heat-shock promoters, and steroid-regulated promoters. In certain embodiments, the nucleic acid editing system and/or gRNA is expressed from a tissue specific promoter, e.g., a promoter that is active in the target tissue more than some other tissues. For example, depending on the target tissue, the promoter is a tissue specific promoter that is expressed in one or more of liver, heart, lung, skeletal muscle, CNS, endothelial cells, stem cell, blood cell or blood cell precursor, and immune cells. Exemplary promoters include RNA III polymerase promoters, and viral promoters such as U6, CMV, SV40, EF-1α, Ubc, and PGK promoters, or derivatives thereof having comparable promoter strength. Other promoters can be selected and/or designed based on publicly available information (see, for example, the mammalian promoter database at mpromdb.wistar.upenn.edu). These and other promoters, expression control elements (e.g., enhancers), and constructs that can be used are described, for example, in U.S. Pat. No. 8,697,359, which is hereby incorporated by reference in its entirety.

The duration of expression of the nucleic acid editing system and/or gRNA can be determined in a suitable cell line that is indicative of expression in the target tissue, and/or where the promoter of choice is expressed in a manner that is comparable with the target tissue. For example, where the target tissue is liver, the duration of expression of the nucleic acid editing system and/or gRNA may be determined in hepatocyte cell culture such as HuH-7 or transformed primary human hepatocytes. Alternatively, Human Embryonic Kidney 293T cells may be used to quantify duration of expression. Expression can be measured by, for example, immunohistochemistry, RT-PCR, or flow cytometry. In some embodiments, a gRNA or nucleic acid editing system such as Cas9, for example, can be expressed with a suitable tag (e.g., HA tag) to monitor expression with commercially available antibodies. In some embodiments, the expression of the nucleic acid editing system and/or gRNA and/or the efficiency of target nucleotide modification can be detected or monitored using reporter genes, reporter sequences, epitope tags, and/or expression tags. A "reporter gene" or "reporter sequence" or "epitope tag" or "expression tag" refers to any sequence that produces a product that is readily measured. Reporter genes include, for example, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG-tag, His, myc, Tap, HA or any detectable amino acid sequence. "Expression tags" include sequences that encode reporters that may be operably linked to a desired gene sequence in order to monitor expression of the gene of interest.

Other exemplary cell lines for which expression of the gRNA(s) or nucleic acid editing system constructs may be quantified include: C8161, CCRF-CEM, MOLT, mIMCD-3, NHDF, HeLa-S3, Huh1, Huh4, Huh7, HUVEC, HASMC, HEKn, HEKa, MiaPaCell, Panel, PC-3, TF1, CTLL-2, C1R, Rath, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRCS, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr −/−, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepalclc7, HL-60, HMEC, HT-29, Jurkat, JY cells, K562 cells, Ku812, KCL22, KG1, KYO1, LNCap, Ma-MeI 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, and YAR.

Repair Templates

In certain instances, where a nucleotide substitution, insertion, or deletion is desired, for example, the compositions, methods, kits, and delivery systems provided herein further comprise a repair template. Repair templates may comprise any nucleic acid, for example, DNA, messenger RNA (mRNA), small interfering RNA (siRNA), microRNA (miRNA), single stranded RNA (ssRNA), or antisense oligonucleotides. In some embodiments, the repair template is a DNA repair template. The basic components and structure of the DNA repair template to support gene editing is known, and described in Ran F A, *Genome editing using the CRISPR-Cas9 System, PNAS* 8(11):2281-308 (2013); and Pyzocha et al., *RNA-guided genome editing of mammalian cells, Methods Mol. Biol.* 1114:269-77 (2014) which are hereby incorporated by reference.

The length of the repair template can vary, and can be, for example, from 200 base pairs (bp) to about 5000 bp, such as about 200 bp to about 2000 bp, such as about 500 bp to about 1500 bp. In some embodiments, the length of the DNA repair template is about 200 bp, or is about 500 bp, or is about 800 bp, or is about 1000 base pairs, or is about 1500 base pairs. In other embodiments, the length of the repair template is at least 200 bp, or is at least 500 bp, or is at least 800 bp, or is at least 1000 bp, or is at least 1500 bp.

In some embodiments, the repair template is in the same delivery vehicle as the gRNA. In other embodiments, the repair template is in the same delivery vehicle as the nucleic acid editing system. In some embodiments, the repair template can be present on a contiguous polynucleotide with the gRNA gene, and the repair template may be designed for incorporation by homologous recombination.

In some embodiments, the delivery system provides a gRNA and repair template, wherein the repair template is covalently or non-covalently bound to the gRNA. In further embodiments, the repair template is partially annealed to the gRNA. In some embodiments, the repair template is covalently or non-covalently bound to a gRNA delivered via a viral vector and the nucleic acid editing system comprises a nuclear localization signal and is delivered by a non-viral vector, such that it carries the gRNA along with the repair template to the nucleus of the cell. Thus, in some embodiments, the delivery systems, compositions, methods, and kits disclosed herein greatly improve the percent efficiency of nucleotide sequence modification by providing a system by which the repair template is efficiently directed to the nucleus of the cell.

Administration of the Delivery Systems

The delivery vehicles (whether comprising conjugates, viral or non-viral vectors, or a combination thereof) may be administered by any method known in the art, including injection, optionally by direct injection to target tissues. In some embodiments, the gRNA, nucleic acid editing system, and, optionally, repair template are administered simultaneously in the same or in different delivery vehicles. In other embodiments, the gRNA and nucleic acid editing system and, optionally, repair template are administered sequentially via separate delivery vehicles. In some embodiments, the gRNA is administered 1, 3, 5, 7, 10, 14, or 30 days prior to administration of the nucleic acid editing system, such that the gRNA accumulates in the target tissue prior to administration of the nucleic acid editing system. In some embodiments, the gRNA and/or nucleic acid editing system is administered in a plurality of doses, such as 2, 3, 4, 5, 6, 7, 8, 9, 10, 11, 12, 13, 14, 15, 16, 17, 18, 19, 20, or more doses. In various embodiments, the gRNA and/or nucleic acid editing system is administered over a time period of from one week to about six months, such as from about two to about ten doses within about two months, such as from about three to about five doses over about one month.

In one embodiment, the gRNA and, optionally, a repair template, are provided in an AAV vector that is administered to the subject or cell prior to administration of a nanoparticle containing the nucleic acid editing system. In a further embodiment, the AAV vector comprising the gRNA is administered 3, 4, 5, 6, 7, 8, 9, or 10 days prior to the administration of the nanoparticle, to allow expression of the gRNA from the AAV vector. In a yet further embodiment, the nanoparticle containing the nucleic acid editing system is administered multiple times, for example, once every 2, 3, 4, 5, 6, 7, 8, 9, 10, 11, 12, 13, 14, or 15 days. In a still further embodiment, the nanoparticle containing the gRNA is administered for 1 month, 2 months, 3, months, 4 months, 6 months, 8 months, 10 months, 12 months, 18 months, 24 months, or longer. Since AAV expression can occur for 2 years or longer, in one embodiment, the expression of the gRNA and, optionally, repair template, from the AAV vector and the continual administration of nanoparticles containing the nucleic acid editing system provides efficient gene editing of the target sequence with reduced or absent off-target effects due to the transient expression of the nucleic acid editing system.

In another embodiment, the repair template is delivered via an AAV vector, and is injected 3, 4, 5, 6, 7, 8, 9, or 10 days prior to the administration of nanoparticles containing the nucleic acid editing system and/or the gRNA. As described above, the nanoparticles may be administered multiple times, and for several months. In such embodiments, the repair template is expressed from the AAV vector in the cell for 2 years or longer, and the nanoparticles comprising the nucleic acid editing system and/or gRNA are administered in multiple administrations over time in order to provide efficient gene editing of the target sequence with reduced or absent off-target effects.

In particular embodiments, one or more gRNA and, optionally, a repair template, is provided in an AAV vector that is administered first, and a Cas9 nucleic acid editing system in a lipid-based delivery vehicle is subsequently administered in one or more doses. In some embodiments, the Cas9 is administered in a lipid-based delivery vehicle about 7 days and about 14 days after the administration of the one or more gRNA in an AAV vector.

In another embodiment, each of the components of the delivery systems provided herein (e.g., the nucleic acid editing system, gRNA and, optionally, repair template) are each contained in the same or in different nanoparticles. In a further embodiment, the nanoparticles containing the nucleic acid editing system, gRNA, and, optionally, repair template, are administered at multiple time points, for example, every 2, 3, 4, 5, 6, 7, 8, 9, 10, 11, or 12 days. In another embodiment, the administration of the nanoparticles separately comprising the nucleic acid editing system and gRNA are administered at different time points in order to enhance gene editing efficiency in a particular cell or for a particular disease type.

In some embodiments, the administration of the delivery system is controlled so that expression of the nucleic acid editing system is transient. In some embodiments, such transient expression of the nucleic acid editing system minimizes off-target effects, thereby increasing the safety and efficiency of the gene editing system disclosed herein. For example, in expression of the nucleic acid system is controlled via selection of the delivery vehicles and/or promoters disclosed herein.

In some embodiments, the present disclosure provides compositions and methods that allow for increased safety and/or efficacy of the nucleic acid editing systems provided herein. For example, in some embodiments, the non-viral delivery of Cas9 results in a reduced or eliminated immune response against Cas9, relative to the immune response elicited against Cas9 when delivered via a viral vehicle. In some embodiments, non-viral delivery of Cas9 triggers little or no immune response in the subject. For example, the concentration of one or more cytokines (e.g. one or more of IL-1α, IL-1β, IL-2, IL-4, IL-6, IL-10, IL-12, IL-17A, IFNγ, G-CSF, and GM-CSF) may, following administration, be about 90%, about 95%, about 100%, about 105%, about 110%, or about 120% of the cytokine concentration compared to a PBS (phosphate-buffered saline) control. Thus, in particular aspects, the concentration range may be about 90% to about 110%, or about 95% to about 100%, when compared to a PBS control. In some embodiments, the methods provided herein with respect to non-viral delivery of Cas9 result in temporary Cas9 expression in the cell. Temporary expression of Cas9, in some embodiments, reduces or eliminates off-target effects and/or reduces or eliminates the induction of immune responses against Cas9 relative to longer-term expression of Cas9 via viral delivery methods.

Advantageously, the non-viral methods disclosed herein provide for repeated dosing such that the efficiency of gene editing increases with each dose, in the absence of the immune stimulation and off-target effects associated with virally delivered Cas9. For example, in some embodiments, the percent efficiency of gene editing increases by about 1%, about 2%, about 5%, about 10%, or more with each subsequent dose. Doses may be from about 0.1 mg/kg to about 300 mg/kg RNA or protein. For example, in some embodiments, Cas9 protein or RNA is administered at a dose of about 0.1 mg/kg to about 300 mg/kg, or about 0.2 mg/kg to about 250 mg/kg, or about 0.3 mg/kg to about 200 mg/kg, or about 0.4 mg/kg to about 150 mg/kg, or about 0.5 mg/kg to about 100 mg/kg, or about 1 mg/kg to about 50 mg/kg. Doses may be about 1 day apart, about 2 days apart, about 3 days apart, about 4 days apart, about 5 days apart, about 6 days apart, about 1 week apart, about 2 weeks apart, about 3 weeks apart, about a month apart, or more.

In some aspects, gene editing without any repair template may facilitate gene repair. Thus, in some embodiments, the present disclosure provides methods, compositions, and delivery systems for gene editing wherein nonhomologous end-joining (NHEJ) rather than homology-driven repair (HDR) is achieved. For example, in some embodiments, a loss of function of a key protein due to an out-of-frame mutation causes a disease or disorder. For example, in muscular dystrophy, the loss of function of a key protein is due to out of reading frame mutations. Thus, in some embodiments, the present disclosure provides methods, compositions, and delivery systems wherein a non-functional gene may be restored to function via deletion of a fragment of a gene, and wherein the methods, compositions, and delivery systems do not comprise a repair template. In some embodiments, the present disclosure provides methods, compositions, and delivery systems wherein a splicing defect may be repaired. In other embodiments, the present disclosure provides methods, compositions, and delivery systems wherein a gene is deleted, for example, a harmful gene that is associated with or causes a disease or disorder. In some embodiments, NHEJ is achieved at a higher efficiency relative to HDR. For example, in some embodiments, the percent efficiency of NHEJ is from about 10% to about 90%.

In another embodiment, the gRNA, Cas9, and, optionally, repair template, are administered to a subject or a cell at the same time, such as on the same delivery vehicle, and one or more component (i.e., the gRNA, Cas9, and/or repair template) is under the control of an inducible promoter. As an example, in one embodiment, the gRNA, Cas9, and repair template are each present on an AAV viral vector, and the gRNA is under the control of an inducible promoter, for example, a small molecule-induced promoter such as tetracycline-inducible promoter. In a further embodiment, the Cas9 is expressed 5-7 days following administration of the vector, after which the expression of the gRNA is induced by one or more injections of the small molecule such as tetracycline. The gRNA expression can be induced at various time points in order to increase gene editing efficiency; for example gRNA expression may be induced every day, or every 2 days, or every 3 days, or every 5 days, or every 10 days, or every 2 weeks, for at least 1 week or at least 2 weeks, or at least 3 weeks, or at least 4 weeks, or at least 5 weeks, or at least 6 weeks, or at least 7 weeks, or at least 8 weeks, or at least 10 weeks, or at least 11 weeks, or at least 12 weeks, or more. Thus, the Cas9 expression may be expressed from the AAV vector over time, and the gRNA may be inducibly expressed by multiple injections of the inducing molecule over several days, weeks, or months. Similarly, the gRNA can be expressed from the AAV vector over time, and the Cas9 may be inducibly expressed under control of an inducible promoter by multiple injections of the inducing molecule over several days, weeks, or months. In a particular embodiment, the AAV vector comprising gRNA on an inducible promoter, Cas9, and a repair template is administered to the subject or cell on day 1; and a small molecule to induce gRNA expression is administered to the subject or cell beginning on day 5, 6, 7, or 8, and every 3 days for several months.

In another embodiment, one or more gRNA and, optionally, a repair template, is delivered via an RNA conjugate, such as an RNA-GalNAc conjugate, and the nucleic acid editing system is delivered via a viral or non-viral vector, such as a nanoparticle. In another embodiment, the gRNA and repair template are attached to the nanoparticle comprising the nucleic acid editing system, such that the components are delivered to the target cell or tissue together. In such embodiments, the gRNA, repair template, and nucleic acid editing system may be delivered to the target cell or tissue together, and expression of each component may be controlled by way of different promoters, including inducible promoters, as disclosed herein.

In one aspect, the present disclosure provides methods for modifying a target polynucleotide in a cell, which may be in vivo, ex vivo, or in vitro. In some embodiments, the one or more delivery vehicles comprising a nucleic acid editing system and/or gRNA and, optionally, repair template, are administered to a subject. In further embodiments, the nucleic acid editing system and gRNA and, optionally, repair template, are targeted to one or more target tissues in the subject. For example, in one embodiment, the target tissue is liver, endothelial tissue, lung (including lung epithelium), kidney, fat, or muscle. In one embodiment, the one or more delivery vehicles comprise a viral vector (e.g., AAV) or a non-viral vector such as, for example, MD-1, 7C1, PBAE, C12-200, cKK-E12, or a conjugate such as a cholesterol conjugate or an RNA conjugate as disclosed herein. In one embodiment, the target tissue is liver, and one or more delivery vehicle is MD-1. In another embodiment, the target tissue is endothelial tissue, and one or more delivery vehicle is 7C1. In another embodiment, the targeting tissue is lung, and one or more delivery vehicle is PBAE or 7C1. In another embodiment, the target tissue is kidney, one or more delivery vehicle is an RNA conjugate. In another embodiment, the target tissue is fat, and one or more delivery vehicle is C12-200. In another embodiment, the target tissue is muscle (e.g., skeletal muscle) and one or more delivery vehicle is a cholesterol conjugate.

The delivery vehicles (whether viral vector or non-viral vector or RNA conjugate material) may be administered by any method known in the art, including injection, optionally by direct injection to target tissues. Nucleic acid modification can be monitored over time by, for example, periodic biopsy with PCR amplification and/or sequencing of the target region from genomic DNA, or by RT-PCR and/or sequencing of the expressed transcripts. Alternatively, nucleic acid modification can be monitored by detection of a reporter gene or reporter sequence. Alternatively, nucleic acid modification can be monitored by expression or activity of a corrected gene product or a therapeutic effect in the subject.

In some embodiments, the subject is a human in need of therapeutic or prophylactic intervention. Alternatively, the subject is an animal, including livestock, poultry, domesticated animal, or laboratory animal. In various embodiments, the subject is a mammal, such as a human, horse, cow, dog, cat, rodent, or pig.

In some embodiments, the methods provided herein include obtaining a cell or population of cells from a subject and modifying a target polynucleotide in the cell or cells ex vivo, using the delivery systems, compositions, methods, and/or kits disclosed herein. In further embodiments, the ex vivo modified cell or cells may be re-introduced into the subject following ex vivo modification. Thus, the present disclosure provides methods for treating a disease or disorder in a subject, comprising obtaining one or more cells from the subject, modifying one or more target nucleotide sequences in the cell ex vivo, and re-introducing of the cell with the modified target nucleotide sequence back into the subject having the disease or disorder. In some embodiments, cells in which nucleotide sequence modification has occurred are expanded in vitro prior to reintroduction into the subject having the disease or disorder. In one embodiment, the cells are bone marrow cells.

In other embodiments, the nucleic acid editing system and gRNA and, optionally, repair template, are administered to a cell in vitro.

In some embodiments, at least one component of the delivery system (e.g., the gRNA or the nucleic acid editing system) accumulates in the target tissue, which may be, for example, liver, heart, lung (including airway epithelial cells), skeletal muscle, CNS (e.g., nerve cells), endothelial cells, blood cells, bone marrow cells, blood cell precursor cells, stem cells, fat cells, or immune cells. Tissue targeting or distribution can be controlled by selection and design of the viral vector, or in some embodiments is achieved by selection and design of lipid or polymeric particles. In some embodiments, the desired tissue targeting of the activity is provided by the combination of viral and non-viral delivery vehicles.

Diseases and Disorders

While the nucleic acid modification system described herein can be used to make essentially any desired change, in some embodiments the subject has a genetic disorder which is sought to be corrected. In some aspects, the disorder is an inborn error of metabolism. In other embodiments, the nucleic acid modification provides a loss of function for a gene that is deleterious. In some embodiments, the inborn error of metabolism can be selected from disorders of amino acid transport and metabolism, lipid or fatty acid transport and metabolism, carbohydrate transport and metabolism, and metal transport and metabolism. In some embodiments, the disorder is hemophilia, cystic fibrosis, or sickle cell disease. Exemplary diseases and conditions that may be treated, prevented or alleviated with the delivery systems, compositions, kits, and methods provided herein include: cystic fibrosis, hemophilia, Huntington Disease, de Grouchy Syndrome, Lesch-Nyhan Syndrome, galactosemia, Gaucher Disease, CADASIL Disease, Tay-Sachs Disease, Fabry Disease, color blindness, cri du chat, duchenne muscular dystrophy, 22q11.2 deletion syndrome, Angelman syndrome, Canavan disease, Charcot-Marie-Tooth disease, down syndrome, Klinefelter syndrome, neurofibromatosis, Prader-Willi syndrome, Tay-Sachs disease, haemochromatosis, phenylketonuria, polycystic kidney disease, sickle cell disease, alpha 1-antitrypsin deficiency (A1AD), and tyrosinemia, growth hormone deficiency, metachromatic leukodystrophy, mucopolysaccharidosis I, phenylketonuria, short chain acyl-CoA dehydrogenase deficiency, alpha-1 antitrypsin deficiency, diabetes, obesity, myocarditis, glomerulonephritis, organophosphate toxicity, xenotransplantation, hypoxic-ischemia encephalopathy, liver regeneration, and various types of cancer, among others.

"Cancer" herein refers to or describes the physiological condition in mammals that is typically characterized by unregulated cell growth. In some aspects, cancer is a genetic disease or disorder as disclosed herein. Examples of cancer include but are not limited to carcinoma, lymphoma, blastoma, sarcoma (including liposarcoma, osteogenic sarcoma, angiosarcoma, endotheliosarcoma, leiomyosarcoma, chordoma, lymphangiosarcoma, lymphangioendotheliosarcoma, rhabdomyosarcoma, fibrosarcoma, myxosarcoma, chondrosarcoma), neuroendocrine tumors, mesothelioma, synovioma, schwanoma, meningioma, adenocarcinoma, melanoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, small cell lung carcinoma, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, Ewing's tumor, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, testicular tumor, lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenstrom's macroglobulinemia, myelodysplastic disease, heavy chain disease, neuroendocrine tumors, Schwanoma, and other carcinomas, as well as head and neck cancer.

Many cancers are characterized by certain gene mutations that promote or "drive" tumorigenesis ("tumor driver genes"), for example, mutations in tumor suppressor genes or pro-apoptotic genes. In some embodiments, the present disclosure provides methods for treating or preventing cancer comprising use of the compositions, methods, and delivery systems provided herein to target tumor driver genes. Advantageously, the compositions, methods, and delivery systems provided herein allow for repeated dosing such that a therapeutic effect can be achieved. Tumor driver genes, oncogenes, and tumor suppressors are known in the art and include, but are not limited to, APC, beta-catenin, CYLD, HIN-1, KRAS2b, p16, p19, p21, p2'7, p27mt, p53, p5'7, p'73, PTEN, MDA-7, Rb, Uteroglobin, Skp2, BRCA-1, BRCA-2, CHK2, CDKN2A, DCC, DPC4, MADR2/JV18, mda7, MEN1, MEN2, MTS1, NF1, NF2, VHL, WRN, WT1, CFTR, C-CAM, CTS-1, zacl, ras, MMAC1, FCC, MCC, FUS1, Gene 26 (CACNA2D2), Yap gene, PL6, Beta (BLU), Luca-1 (HYAL1), Luca-2 (HYAL2), 123F2 (RASSF1), 101F6, and Gene 21 (NPRL2). Pro-apoptotic genes are known in the art and include, but are not limited to, CD95, caspase-3, Bax, Bag-4, CRADD, TSSC3, bax, hid, Bak, MKP-7, PARD, bad, bcl-2, MST1, bbc3, Sax, BIK, and BID. The present disclosure also provides for the treatment or prevention of cancer by targeting tumor driver genes as well as targeting immune suppressor genes associated with cancer. Immune suppressors associated with cancer are known in the art and include, for example, IDO, FasL, VEGF, IL-10 TGF-β, TRAIL, DAF, iNOS, CTLA-4, and STAT3.

In some embodiments, a tumor suppressor, oncogene and/or immune suppressor gene is targeted, and a paracrine effect is achieved via the methods, compositions, and delivery systems provided herein. For example, in some embodiments, tumor suppressing effects can be increased or optimized even where the gene editing is not 100% efficient, because the targeted tumor cells or cells in the tumor microenvironment will allow further tumor suppressing effect or activate the immune response against the tumor for further tumor suppressing effect.

Exemplary genetic disorders that can be treated or ameliorated in various embodiments, as well as target genes that can be edited for improved or reduced activity, are disclosed in U.S. Pat. No. 8,697,359, which are hereby incorporated by reference.

Therapeutic Effect

"Therapeutic effect" as used herein refers to an effect on a disease or condition that is a measurable improvement in the progression, symptoms, or phenotype of the disease or condition. A "therapeutic treatment" or "therapeutically effective amount" provides a therapeutic effect in a subject. A therapeutic effect may be a partial improvement or may be a complete resolution of the disease or disorder. A therapeutic effect may also be an effect on a disease or condition as measured using a test system recognized in the art for the particular disease or condition. A therapeutic effect may also be a prophylactic effect, such that the disease or condition may be prevented, or such that symptoms of an underlying disease or condition may be prevented before they occur. For example, the delivery systems, methods, compositions, and kits disclosed herein may be used to correct or improve a gene product such that the onset of a disease or condition, or an infection with an infectious agent, is prevented. A "gene product" as used herein refers to a product of gene expression. In various embodiments, the gene product is a protein or enzyme; however, a gene product may also be RNA (e.g., when the gene codes for a non-protein product such as functional RNA).

In one aspect, the delivery systems, compositions, methods, and kits disclosed herein are useful for therapeutic treatment of genetic diseases and disorders, cancers, immune system disorders, or infectious diseases. In some embodiments, the diseases, disorders, and cancers are associated with mutations that cause expression of one or more defective gene products, or cause an aberrant increase or decrease in the production of a gene product. In some embodiments, the therapeutic efficacy of the delivery systems, compositions, methods, and kits disclosed herein may be assessed or measured by expression level or activity level of the product of the targeted nucleotide sequence. In some embodiments, gene loci are sequenced by Sanger or Next Generation Sequencing. In some embodiments, in human subjects or other subjects, a therapeutic effect or the therapeutic efficiency of the compositions and methods for target sequence modification disclosed herein may be measured or monitored using surrogate markers of efficiency. Surrogate markers of efficiency may be, for example, an improvement in a symptom of the disease or condition; a clinical marker such as, for example, liver function; expression of a wild-type gene product or an improved gene product relative to the gene product that was expressed in the cell or subject prior to treatment; expression of a sufficient amount or activity of the gene product to improve or resolve the disease or disorder; or expression of the gene product in a manner that provides any other therapeutic effect. In some embodiments, surrogate markers may include serum markers such as, for example, factor VIII and/or IX. For example, factor VIII and factor IX can be measured as surrogate markers for efficiency of treatment for hemophilia A and hemophilia B, respectively. In some embodiments, any gene product excreted through exosome to the serum can be detected by purification and sequencing.

In some embodiments, the disease or disorder may be therapeutically treated using the methods, compositions, kits, and delivery systems disclosed herein, wherein an efficiency rate of target sequence modification or an efficiency rate of gene product modification is at least 50%, at least 55%, at least 60%, at least 65%, at least 70%, at least 75%, at least 80%, at least 85%, at least 90% at least 95%, or at least 99%. In some embodiments, the disease or disorder may be therapeutically treated using the methods, compositions, kits, and delivery systems disclosed herein, wherein an efficiency rate of target sequence modification or an efficiency rate of gene product modification is less than 100%, or wherein an effect on fewer than 100% of the cells in the relevant tissue, has a therapeutic effect in the subject. For example, a therapeutic effect may be achieved when the percent efficiency of nucleic acid modification may be about 0.01% to about 100%, about 0.01% to about 50%, about 0.05% to about 40%, about 0.1% to about 30%, about 0.5% to about 25%, about 1% to about 20%, about 1% to about 15%, about 1% to about 10%, or about 1% to about 5%. Thus, even if the efficiency of nucleotide sequence modification is relatively low (e.g., less than 50%, or less than 40%, or less than 30%, or less than 20%, or less than 10%, or less than 5%, or less than 1%, or less than 0.5%, or less than 0.1%), modest expression of the introduced or corrected or modified gene product may result in a therapeutic effect in the disease or disorder.

Thus, in some embodiments, a genetic disease or condition may be improved or resolved even if the target nucleotide sequence is only modified in a fraction of the target population of cells in the subject. In some embodiments a percent efficiency of nucleic acid modification of less than 50%, less than 40%, less than 30%, less than 20%, less than 10%, less than 5%, less than 1%, less than 0.5%, or less than 0.1% nevertheless results in high level expression of an introduced or corrected gene and thereby resolves the genetic disorder by providing sufficient expression of the relevant product.

In some genetic disorders, the presence of only a few improved or corrected gene product results in a measurable improvement or even resolution of the disease or disorder. For example, without wishing to be bound by theory, disorders in which disease is caused by a simple deficiency of a particular gene product may be resolved with a limited number of nucleotide sequence modifications. For example, recessively inherited disorders are often simple loss-of-function mutations, and often there is a wide variation in the normal levels of gene expression (e.g., heterozygotes often have about 50% of the normal gene product and are asymptomatic), such that expression of a relatively small percentage of the normal gene product may be sufficient to resolve the disorder. On the other hand, dominantly inherited disorders in which heterozygotes exhibit loss-of-function with 50% of the normal gene product may, in some embodiments, require a higher level of nucleotide sequence modification in order to achieve a therapeutic effect. For example, and without wishing to be bound by theory, disorders such as cystic fibrosis an Muscular dystrophy (MD) may exhibit a therapeutic effect upon an efficiency of about 1% to about 40%; hemophilia A and B, galactosemia, primary hyperoxaluria, hepatoerythropoietic porphyria, and Wilson's disease may each exhibit a therapeutic effect upon achieving an efficiency of about 1% to about 5%; and alpha 1-antitrypsin deficiency, hereditary tyrosinemia type I, Fanconi's anemia, and junctional epidermolysis bullosa may each exhibit a therapeutic effect upon achieving an efficiency of about 0.1% to about 5%. A percent efficiency of nucleic acid modification may be directly measured in animal models or in in vitro assays by measuring the percent of cells in the target population in which the target nucleotide sequence has been modified. Or, a percent efficiency of nucleic acid modification may be indirectly measured, such as by using surrogate markers as described above.

In some embodiments, the method modifies a target sequence that is a genetic variant selected from a single-nucleotide polymorphism (SNP), substitution, insertion, deletion, transition, inversion, translocation, nonsense, missense, and frame shift mutation. In other embodiments, the target sequence is a sequence from an infectious agent, such as a virus or provirus. A provirus is a viral genome that has integrated into the DNA of a host cell. Proviruses may be retroviruses or other types of viruses that are capable of integration into a host genome. For example, adeno-associated viruses (AAV) have been shown to be capable of host chromosome integration. Other proviruses include, without limitation, HIV and HTLV.

In some embodiments, the delivery systems and compositions disclosed herein are formulated such that the ratio of the components is optimized for consistent delivery to the target sequence and/or consistent resolution of the disease or disorder. In one embodiment, the ratio of the gRNA and nucleic acid editing system is optimized for consistent delivery to the target sequence and/or consistent resolution of the disease or disorder. In another embodiment, the ratio of the repair template to the gRNA and/or to the nucleic acid editing system is optimized for consistent delivery to the target sequence and/or consistent resolution of the disease or disorder. For example, in some embodiments, the delivery systems provide expression of an optimal number of gRNAs such that upon delivery to the cell, target tissue, or subject, the modification of target nucleotide sequences by the gRNA and nucleic acid editing system and, optionally, repair sequence, can be maximized. For example, in one embodiment, the ratio of Cas9:sgRNA:template is from about 1:1:1 to about 1:1:100. In a further embodiment, the ratio is from about 1:1:2 to about 1:1:90, from about 1:1:5 to about 1:1:75, or from about 1:1:10 to about 1:1:50. In other embodiments, the ratio is about 1:1:1 or below, such as from about 1:1:0.01 to about 1:1:1, from about 1:1:0.02 to about 1:1:0.75, or about 1:1:0.05 to about 1:1:0.5, or about 1:1:0.1 to about 1:1:0.5. For example, in some embodiments, the ratio of Cas9:sgRNA:template is 1:1:1 or below when NHEJ is inhibited or when Cas9 is fused with one or more proteins that can facilitate HDR. In other embodiments, wherein the delivery systems do not comprise a repair sequence, the ratio of Cas9:sgRNA is from about 1:100 to about 100:1, or about 1:50 to about 50:1, or about 1:25 to about 25:1, or about 1:10 to about 10:1, or about 1:5 to about 5:1, or about 1:2 to about 2:1, or about 1:1.

In one aspect, the present disclosure provides methods for safe and efficient delivery of a nucleic acid editing system via a non-viral vector delivery system, or via a system that includes a viral vector as well as a non-viral vector, such that off-target effects (e.g., off-target effects due to long term expression of a nucleic acid editing system and a gRNA through genome integration of an AAV vector delivery system) are minimized. In some embodiments, the present disclosure provides methods for delivery of a nucleic acid editing system that provide a favorable safety margin. By "favorable safety margin," is meant that the compositions and methods provided herein provide gene editing that is both safe and efficient according to the efficiency determinations provided herein. Safety may be determined by any method known in the art, for example, low off-target effects and/or minimal cytotoxicity and/or intact or normal organ histology (e.g., liver histology), and/or normal serum biochemistry and/or normal levels of serum cytokines. Safety may further be determined by comparing the off-target effects and/or cytoxicity and/or organ histology and/or biochemistry and/or serum cytokines with other methods of gene editing known in the art. In one aspect, the present disclosure provides a safe and efficient method for gene editing comprising administering to a cell or subject a Cas9 nucleic acid editing system in a lipid-based vector, e.g., a vector comprising C12-200, cholesterol, C14-PEG 2000, DSPC and Cas9 mRNA. In some embodiments, the Cas9 mRNA encodes the Cas9 protein with chemical modifications to decrease immune stimulation, as provided herein.

In one aspect, the disclosure provides kits containing any one or more of the components disclosed in the above methods, compositions, and delivery systems. Kit components may be provided individually or in combinations, and may be provided in any suitable container, such as a vial, a bottle, or a tube. In some embodiments, the kits disclosed herein comprise one or more reagents for use in the embodiments disclosed herein. For example, a kit may provide one or more reaction or storage buffers. Reagents may be provided in a form that is usable in a particular assay, or in a form that requires addition of one or more other components before use (e.g. in concentrate or lyophilized form). Suitable buffers include, but are not limited to, phosphate buffered saline, sodium carbonate buffer, sodium bicarbonate buffer, borate buffer, Tris buffer, MOPS buffer, HEPES buffer, and combinations thereof. In some embodiments, the buffer is alkaline. In some embodiments, the buffer has a pH from about 7 to about 10.

For example, a kit may comprise: (1) a gRNA and (2) a nucleic acid editing system. The kit may further comprise a repair template. The kit may provide (1) an expression system providing for expression of a gRNA in a target cell or target tissue for at least 2 weeks, the gRNA directing cleavage of a target nucleic acid sequence in the target tissue by a nucleic acid editing system, and the expression system optionally comprising a repair template, and (2) one or more doses of an RNA delivery system, each dose providing for expression of the nucleic acid editing system in the target tissue for no more than about one month. In various embodiments, the kit may provide from two to ten doses of the RNA delivery system, which may be administered over a time period of from one week to about two months. In some embodiments, the kit contains from about two to about five unit doses.

The kit may be custom made to repair a genetic disorder, such as an inborn error of metabolism, or a cancer. In other embodiments, the nucleic acid modification provides a loss of function for a gene that is deleterious. In some embodiments, the inborn error of metabolism can be selected from disorders of amino acid transport and metabolism, lipid or fatty acid transport and metabolism, carbohydrate transport and metabolism, and metal transport and metabolism. In some embodiments, the disorder is hemophilia, cystic fibrosis, or sickle cell disease.

EXAMPLES

Example 1

Correction of Gene Defect by Two Delivery Vehicles

The type II bacterial clustered, regularly interspaced, palindromic repeats (CRISPR)-associated (Cas) system has been engineered into a powerful genome editing tool consisting of the Cas9 nuclease and a single gRNA (sgRNA). The sgRNA targets Cas-9 to genomic regions that are complementary to the 20-nucleotide target region of the sgRNA and that contain a 5'-NGG-3' protospacer-adjacent motif (PAM). Double-stranded DNA breaks generated by Cas9 at target loci are repaired by non-homologous end-joining or homology-directed repair (HDR). We have demonstrated CRISPR-Cas9-mediated correction of a Fumarylacetoacetate hydrolase (Fah) mutation in hepatocytes in a mouse model of the human disease hereditary tyrosinemia. Delivery of components of the CRISPR-Cas9 system by hydrodynamic injection resulted in initial expression of the wild-type FAH protein in ~1/250 liver cells. Expansion of FAH-positive hepatocytes rescued the body weight loss phenotype. Example 1 demonstrates the use of a viral and non-viral vector delivery vehicles administered sequentially in vivo, along with repair template to correct a FAH gene mutation in the liver. Specifically, using the CRISPR-Cas9 system and combining a lipid nanoparticle for mRNA delivery and a viral vector for DNA delivery, FAH genes were corrected in the liver of adult mice.

Specifically, an AAV-2/8 virus was designed to express a gRNA and to provide a DNA repair template. Cas9 mRNA was encapsulated in lipid nanoparticles using cKK-E12, DOPE, Cholesterol, and C14_PEG2000. This lipid nanoparticle showed significant delivery of Cas9 mRNA to liver. Injecting AAV-2/8 virus to express a gRNA against the mutant FAH gene and a correct FAH repair template, and lipid nanoparticles encapsulated Cas9 mRNA, provided efficient in vivo gene correction.

FIG. 1 shows the design of DNA carried by Adeno-Associated Virus (AVV) 2/8, which can deliver DNA to liver of human and rodents with high efficiency. After packing the designed DNA sequence into the AAV 2/8, the vector can express through a U6 promoter a sgRNA targeting the region of the FAH mutation (Exon 8 of FAH). Meanwhile, a repair template was provided in the same vector. The repair template contains the correct sequence harboring a "G" rather than "A" at the mutated site. The left and right arm is about 800 bp each. Because AAV is a single stand DNA virus, the AAV with such sequence can be used as a repair template. The FM and R10 primer can be used to amplify the region for further analysis.

FIGS. 2A-B shows packing Cas9 mRNA into cKK-E12. (A) The structure of lipid nanoparticle carrying Cas9 mRNA. cKK-E12 is a house developed lipid. Cas9 mRNA is purchased from TriLink BioTechnologies. Cas9 mRNA expresses a version of the Streptococcus pyogenes SF370 Cas9 protein (CRISPR Associated Protein 9) that has been codon optimized for expression in mammalian systems and contains a C-terminal nuclear localization signal followed by a human influenza hemagglutinin (HA) tag. This capped and polyadenylation mRNA is optimized for mammalian systems and modified to reduce immune stimulation. It mimics a fully processed mature mRNA. (B) The lipid nanoparticle was injected to FVB/N mice at 1 mg/kg, and liver harvested 24 hours later. Western blot was performed to detect HA tag in Cas9. The Cas9 protein is about 140-150 kd in protein gels, and was detected by HA antibody at 1:1000 dilution.

FIGS. 3A-B shows analysis of FAH mutant mice that received the AAV 2/8 delivery vehicle on Day 0, and at Day 7 and Day 14, received 1 mg/kg of the lipid nanoparticle encapsulated Cas9 mRNA (or PBS as a control). At Day 21, mice were sacrificed and liver taken for immunohistochemistry staining using FAH antibody. (A) Low resolution picture to show a large area of liver. (B) High resolution.

In conclusion, efficient in vivo gene editing by combination of viral and non-viral vector to deliver CRISPR-Cas system and a template for editing.

Example 2

In Vitro Testing System

An in vitro testing system for the gene editing system described in Example 1 was established. An sgRNA targeting EGFP was expressed in HEK293T cells, which overexpress EGFP. Cas9 mRNA-LNP was added to the cells in vitro and EGFP expression was assessed by flow cytometry. The results of the study are provided in FIG. 4. Untreated HEK293T cells expressing the EGFP-targeting sgRNA expressed high levels of EGFP (left panel). When MD-1-Cas9mRNA or C12-200-Cas9mRNA were added to the HEK293T cells (center panel or right panel, respectively), EGFP expression was knocked down in over 45% of the cells.

Thus, the study indicated that in vitro delivery of Cas9 via a non-viral vector such as a lipid nanoparticle to cells expressing a sgRNA results in robust reduction of expression of the nucleic acid targeted by the sgRNA.

Example 3

Studies were conducted to optimize the sgRNAs in the FAH mouse model system. Mutations were detected using a Surveyor assay, and the results of the studies are provided in FIGS. 5-7. The surveyor assay is a robust method to detect mutations and polymorphisms in DNA. Suveryor nuclease recognizes and cleaves all types of mismatches arising from the presence of single nucleotide polymorphisms or from small insertions or deletions. Surveyor assay is based on the generation of PCR products that are subsequently hybridized to generate mismatches in heteroduplexed DNA, which is then treated and cleaved by Surveyor nuclease. Size based fragmentation analysis is performed to detect cleaved DNA.

Figure 5:
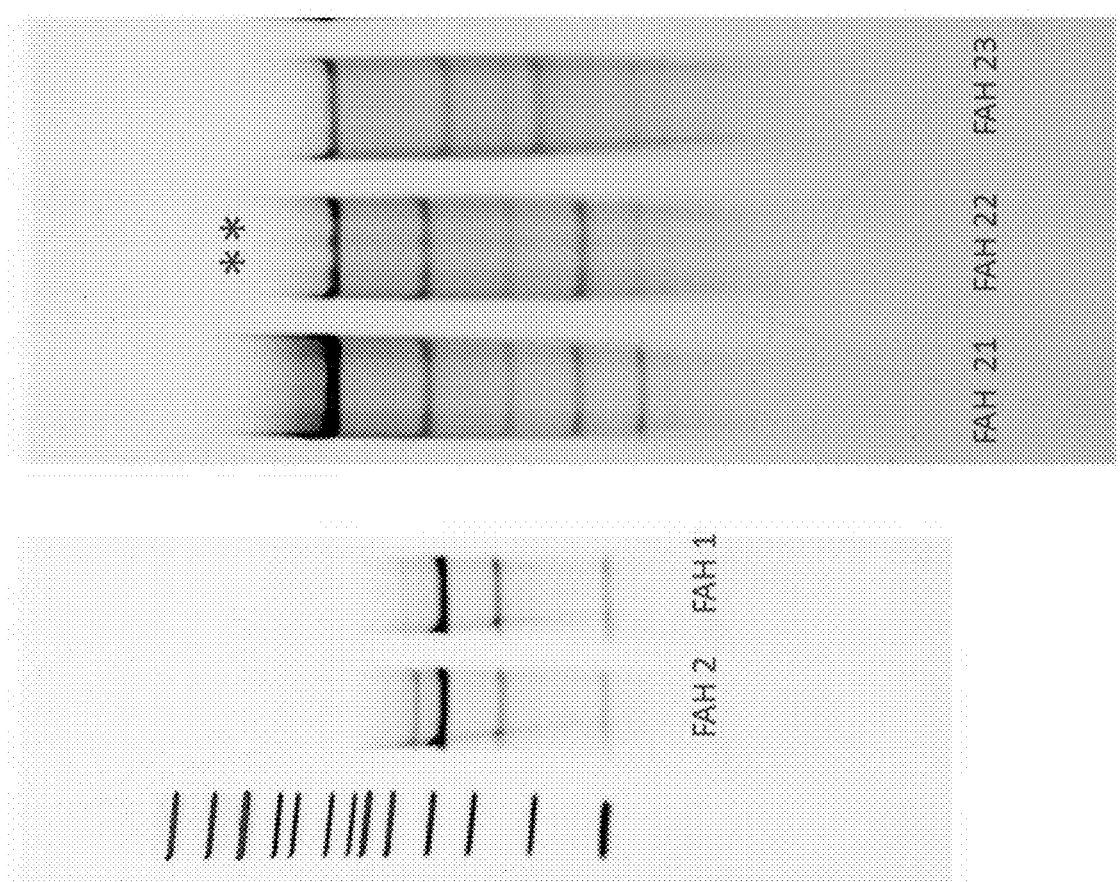
FIG. 5 provides the selection of the most potent sgRNA in vitro. sgRNAs were screened in a cell line established from an FAH mouse. A surveyor assay was performed to determine the efficiency of indels formation.
Figure 6:
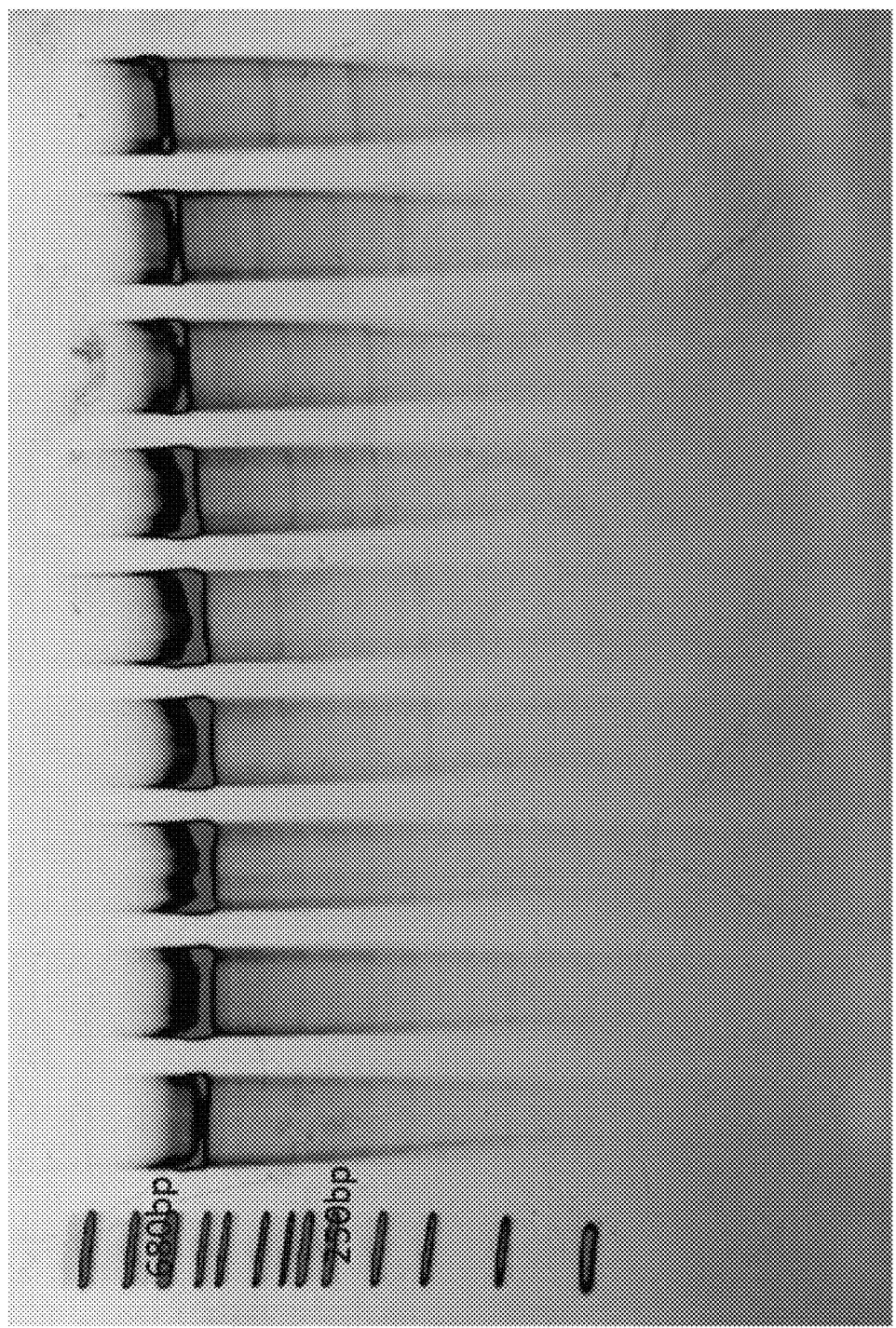
FIG. 6 provides selection of the most potent sgRNA in vivo. sgRNA were screened in the liver through hydrodynamic injection, and a surveyor assay was performed to determine the efficiency of indels formation.
Figure 7:
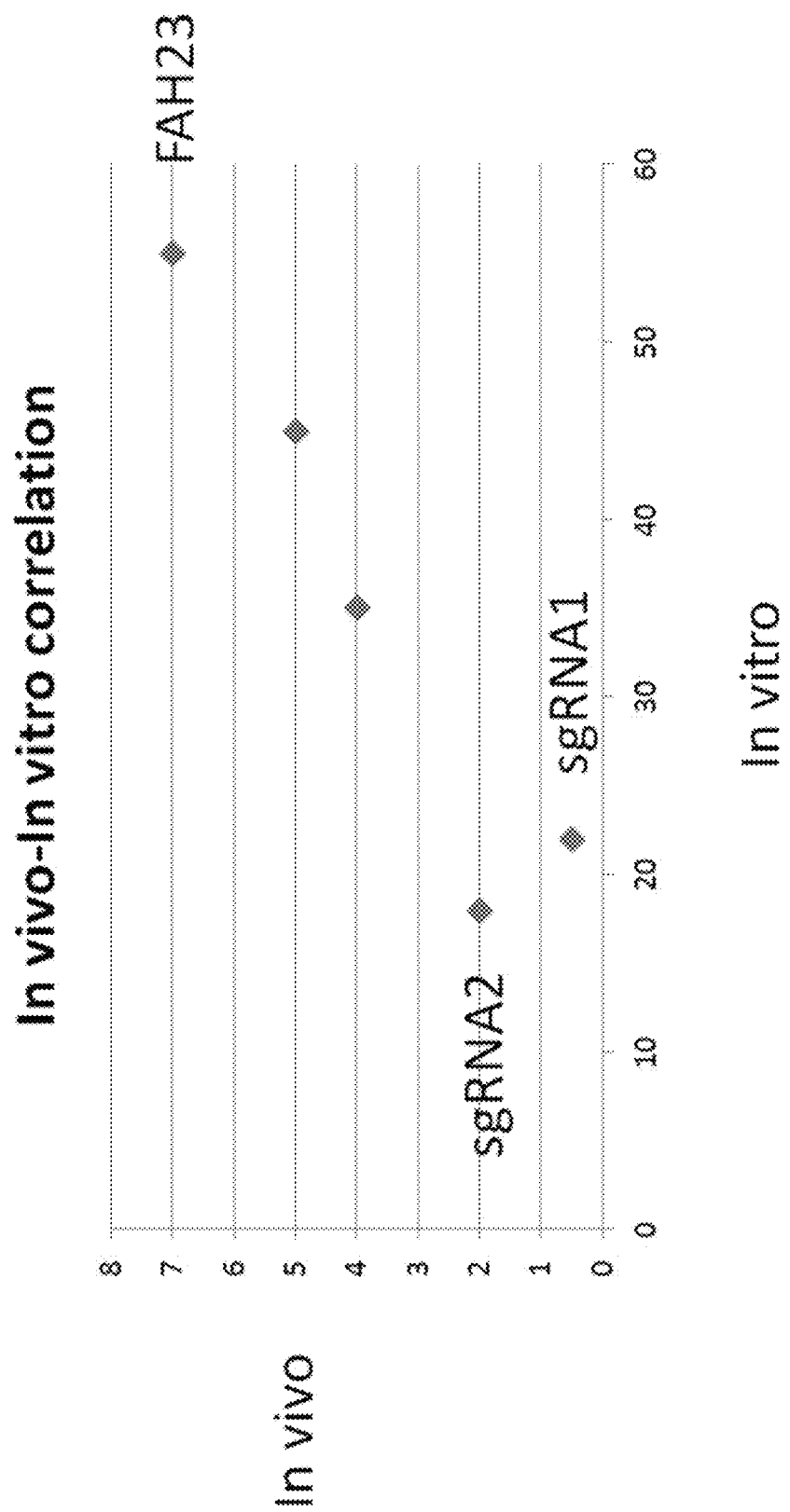
FIG. 7 provides the in vivo and in vitro correlations of indels formation by deep sequencing.

FIG. 5 provides the selection of the most potent sgRNA in an in vitro system. In this system, mouse embryonic fibroblasts were isolated from FAH mice and immobilized by shRNA P53; transfection efficiency was increased by overexpression of mutated Ras gene. The system reached more than 90% transfection efficiency. FIG. 6 provides the selection of the most potent sgRNA in vivo. For the in vivo assay, FAH mice were administered sgRNA via hydrodynamic injection, and a surveyor assay was performed to determine the efficiency of indels formation. The in vitro and in vivo correlations of indels formation obtained from these experiments are provided in FIG. 7. The results of the study showed that FAH23 provided the best efficiency both in vitro and in vivo.

Example 4

Lipid Nanoparticle-Mediated Delivery of Cas9 mRNA in Liver Disease Therapy

A non-viral delivery of Cas9 mRNA allows for a shorter tem expression and eventual removal of the nuclease from the body. A systemic delivery of Cas9 mRNA by lipid nanoparticles and sgRNA/HDR template by AAV was performed through a method of treating $Fah^{mut/mut}$ mice.

Cas9 mRNA was formulated with C12-200, which is a lipid-like material utilized in facilitating siRNA delivery in rodents and primates. Cas9 mRNA was also formulated with associated helper lipids. Nanoparticles were formulated with Cas9 mRNA, which was chemically modified to reduce TLR responses, Mice Study All animal experiments were performed under the guideline of the MIT Animal Care and Use Committee. $Fah^{mut/mut}$ mice were kept on 10 mg/L NTBC water. Mice with more than 20% weight loss were humanely euthanized according to MIT protocol. 1 or 2 mg/kg nano.Cas9 mRNA and 6e11 genome copy AAV8 were injected into 9-11 weeks old $Fah^{mut/mut}$ mice through tail vein. To measure initial repair rate, $Fah^{mut/mut}$ mice were kept on NTBC water.

Cas9 mRNA Nanoparticle Formulation

Cas9 mRNA encodes the Cas9 protein with chemical modification of pseudouridine and 5-methylcytidine to decrease immune stimulation (Trilinkbiotech). Nano.Cas9 was formulated with C12-200, cholesterol, C14-PEG 2000, DSPC and Cas9 mRNA in a weight ratio of 50:20:10:10 using microfluidic method.

Construction of AAV Vectors and Virus Production

AAV vector was constructed using Gibson assembling. AAV2/8 virus were prepared and purified by vector cores at Boston Children's Hospital Viral Core.

Liver Histology, Serum Markers, and Cytokines

Mice were humanely sacrificed by CO2. Livers were freshly fixed with 4% PFA (paraformaldehyde) and embedded in paraffin. 4 μm sections were stained with hematoxylin and eosin (H&E) for pathology and with anti-Fah (Abcam, 1:400) antibody for immunohistochemistry, as described in, for example, Xue et al. *Response and resistance to NF-kappaB inhibitors in mouse models of lung adenocarcinoma. Cancer Discov.* 1:236-247 (2011). The percentage of positive cells was measured at low magnification lens from >3 regions per liver in at least 3 mice per group. Blood was collected using retro-orbital puncture at terminal time point. ALT, AST and bilirubin levels in serum were measured as described in, for example, Yin et al. *Genome editing with Cas9 in adult mice corrects a disease mutation and phenotype. Nat. Biotechnol.* 32:551-553 (2014). Cytokine levels in plasma were determined by Multi-Analyte ELISArray (Qiagen).

Gene Expression Analysis and qRT-PCR

RNA was purified using Trizol (Invitrogen) and reverse-transcribed using a High-Capacity cDNA Reverse Transcription Kit (Applied Biosystems). Real-time PCR (qPCR) reactions were performed using gene specific primers (Roche 480). Data were normalized to Actin.

Cell Culture, Off-Target Analysis, Illumina Sequencing, and Statistics 293T cells were infected with lentivirus to stably express EF1a-GFP (addgene 26777) and U6-sgGFP, as described in, for example, Gilbert et al. *CRISPR-mediated modular RNA-guided regulation of transcription in eukaryotes. Cell.* 154: 442-451 (2013). Cells were incubated with nano.Cas9 mRNA. GFP+ cells were counted by FACS. Off-target sites prediction was using http://crispr.mit.edu/. Deep sequencing libraries were prepared from ~1 ng purified PCR products using Nextera XT kits (Illumina). Libraries at equal molar ratio were sequenced on Illumina NextSeq500 (75 bp, paired-end) or MiSeq machines (150 bp, paired-end) or Single molecule labelled. Reads were mapped to reference sequences using bwa with custom scripts. P-values were determined by Student's t-tests and One-Way ANOVA with Tukey post-test using Prism 5 (GraphPad).

Results

Figure 8A:
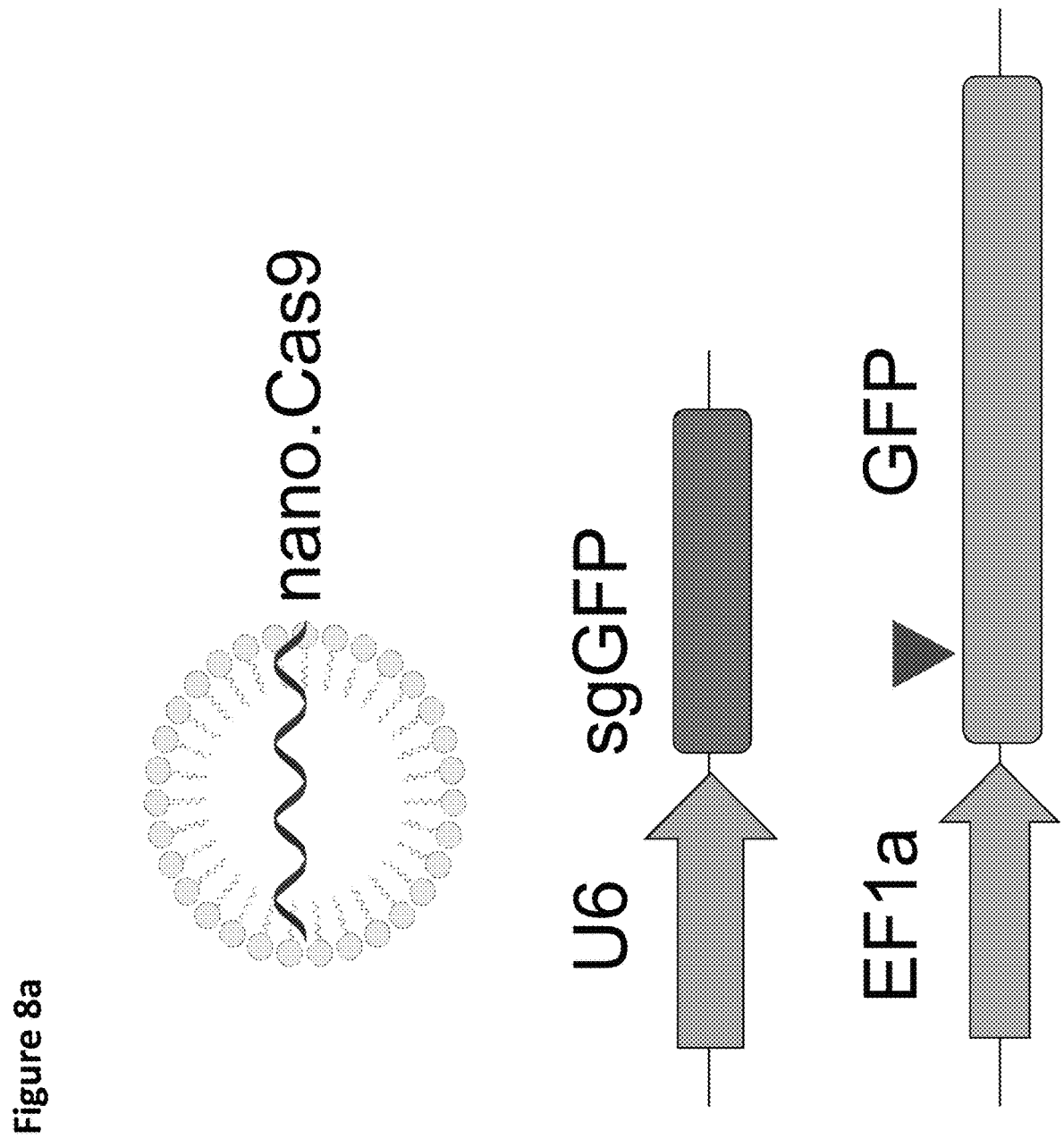
Figure 8B:
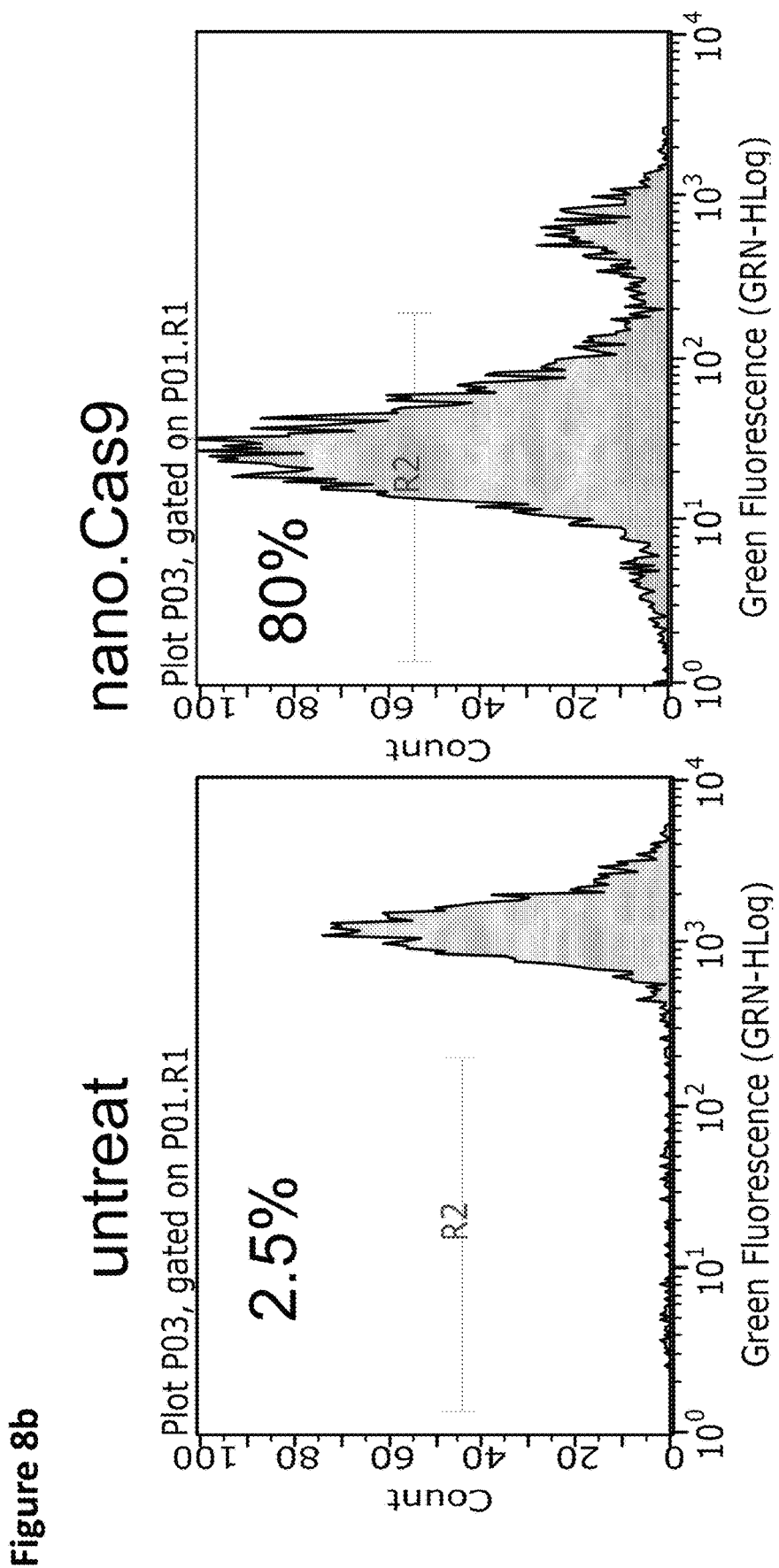
Figure 8D:
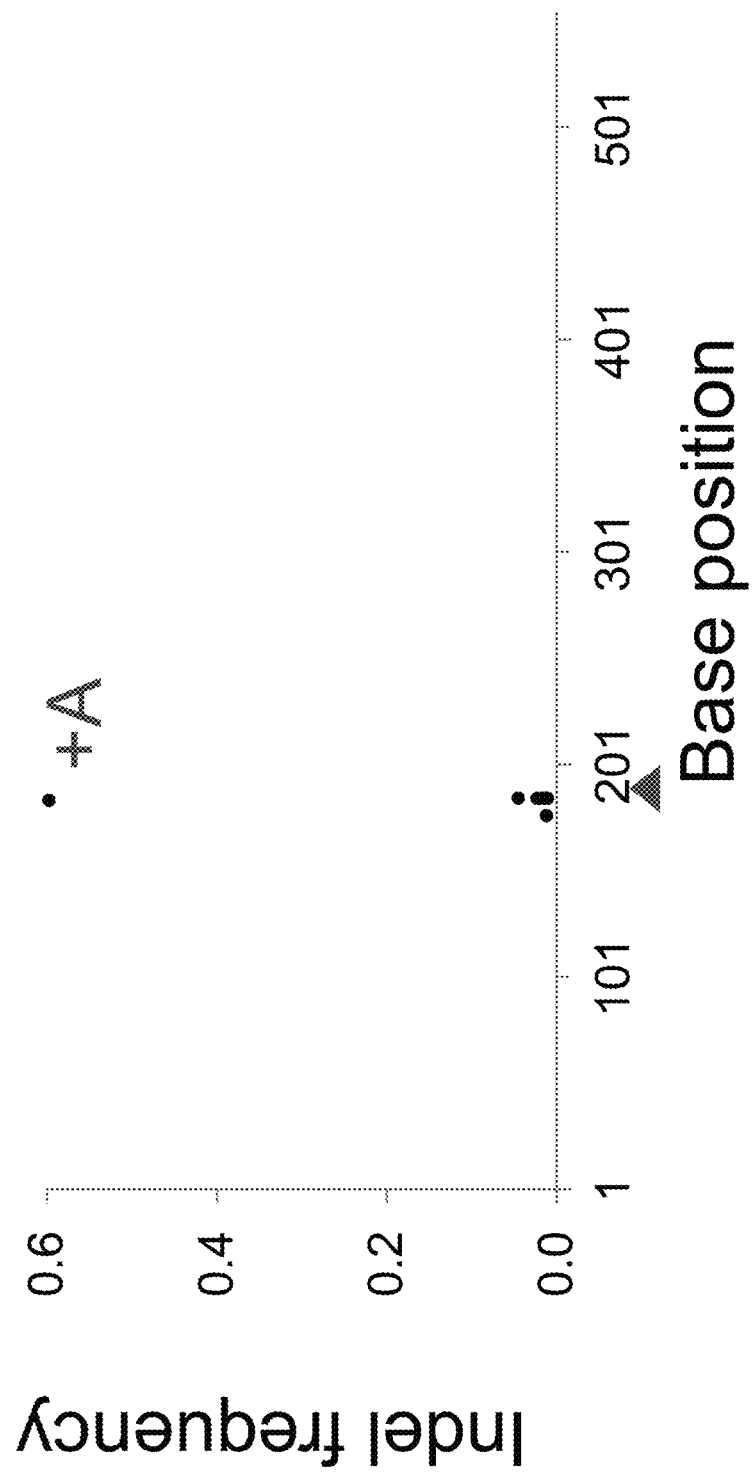
Figure 8E:
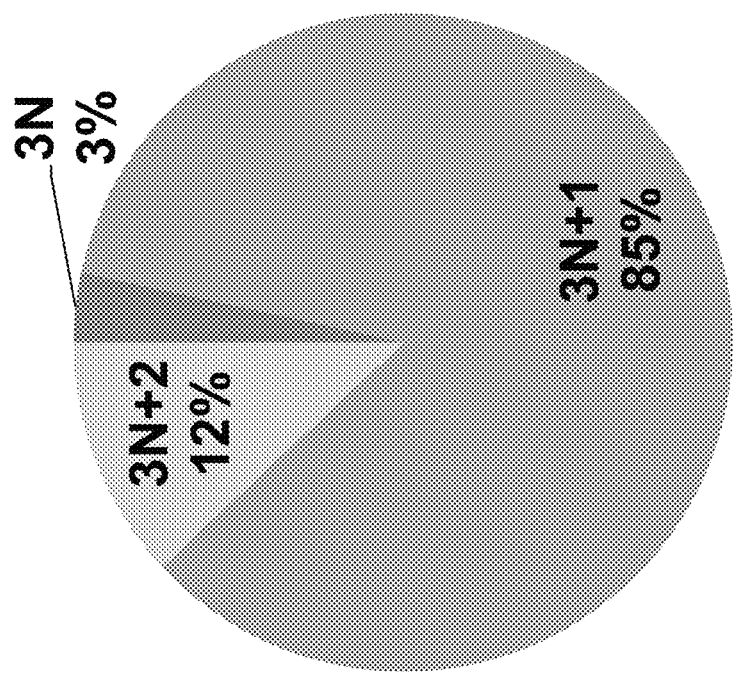
Figure 11A:
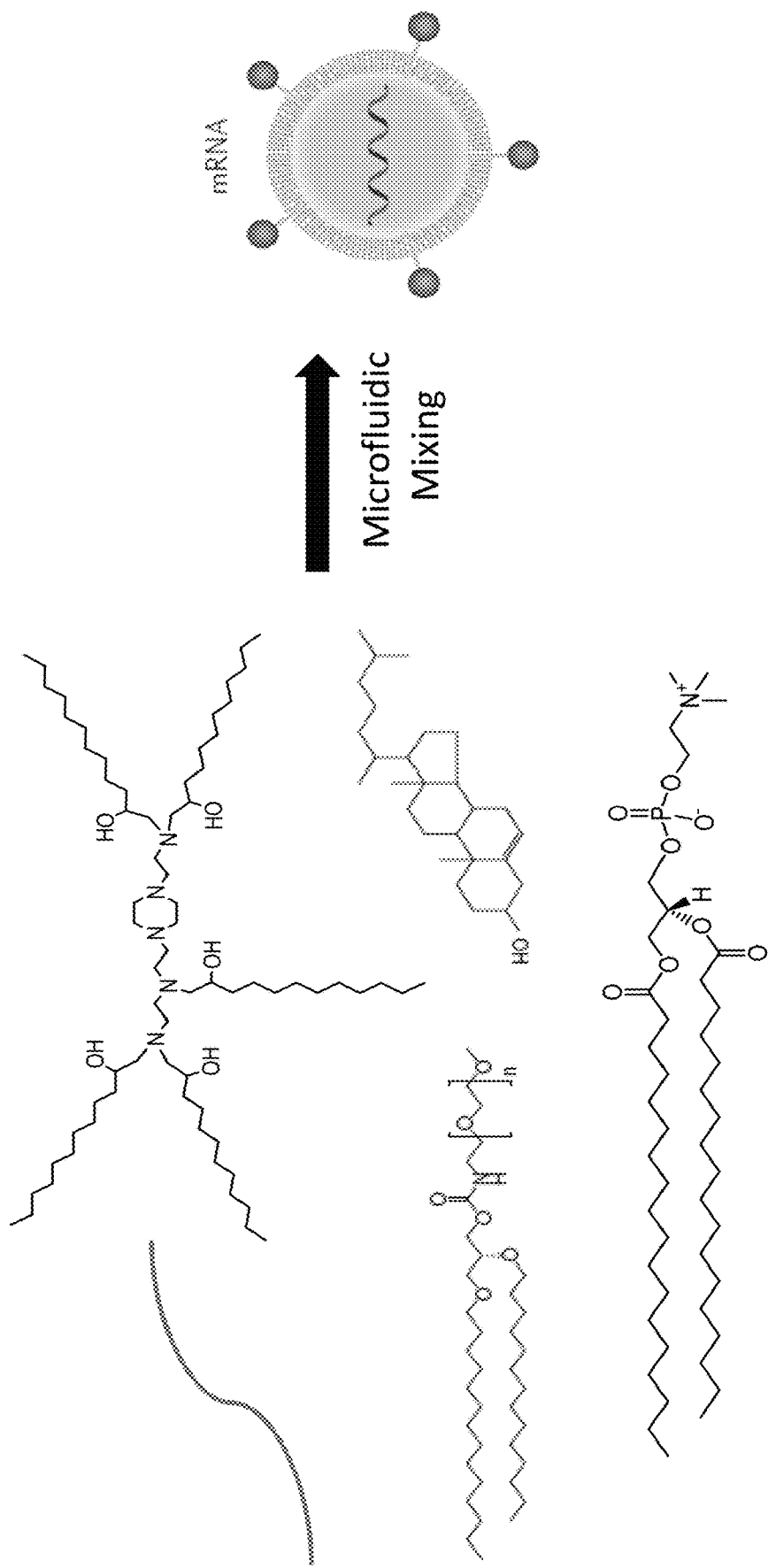
FIGS. 11A-11E provide Cas9 mRNA nanoparticles characterization.
Figure 11B:
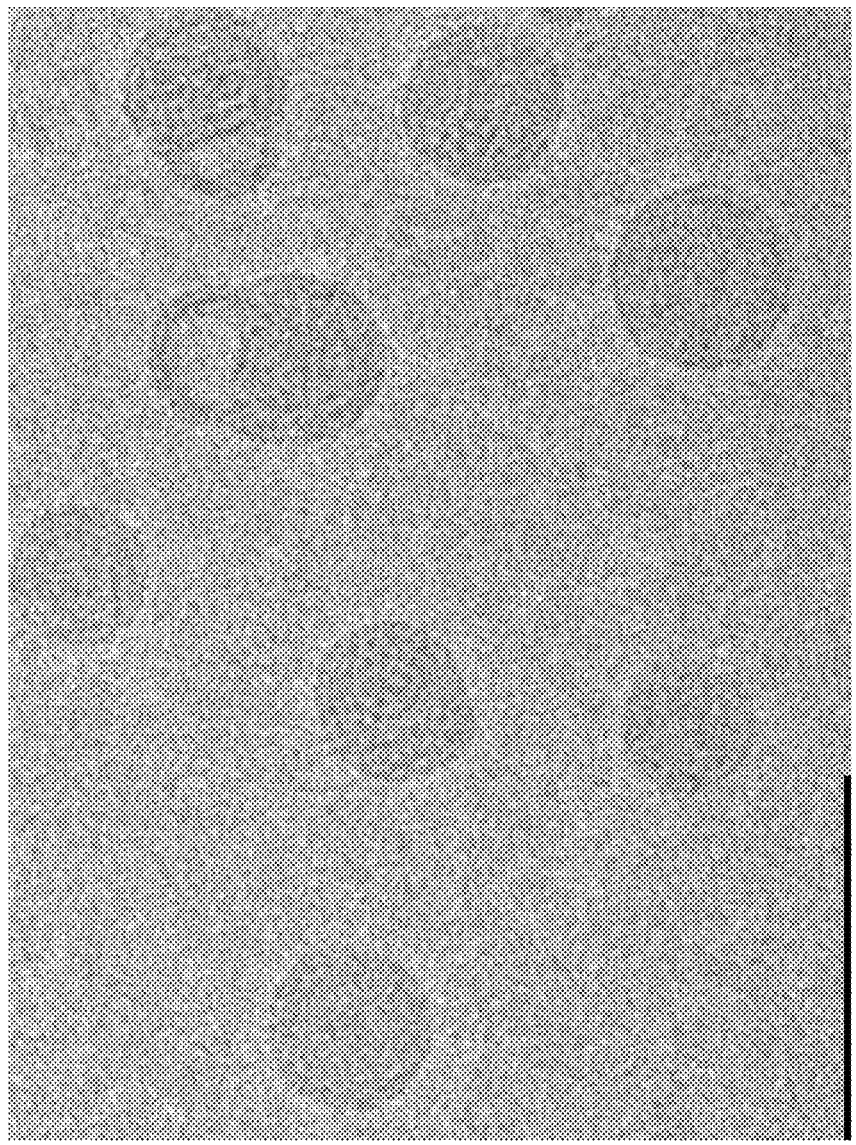
Figure 11C:
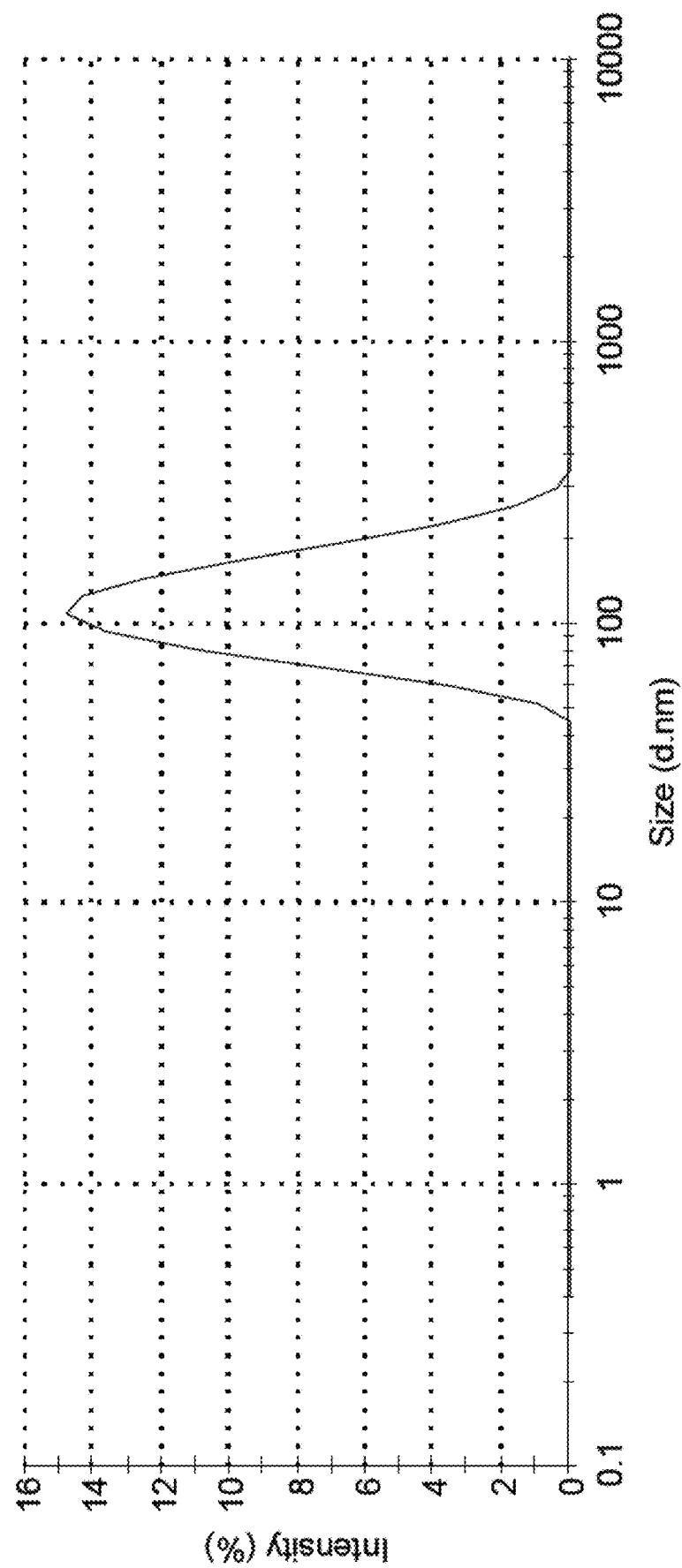
Figure 11D:
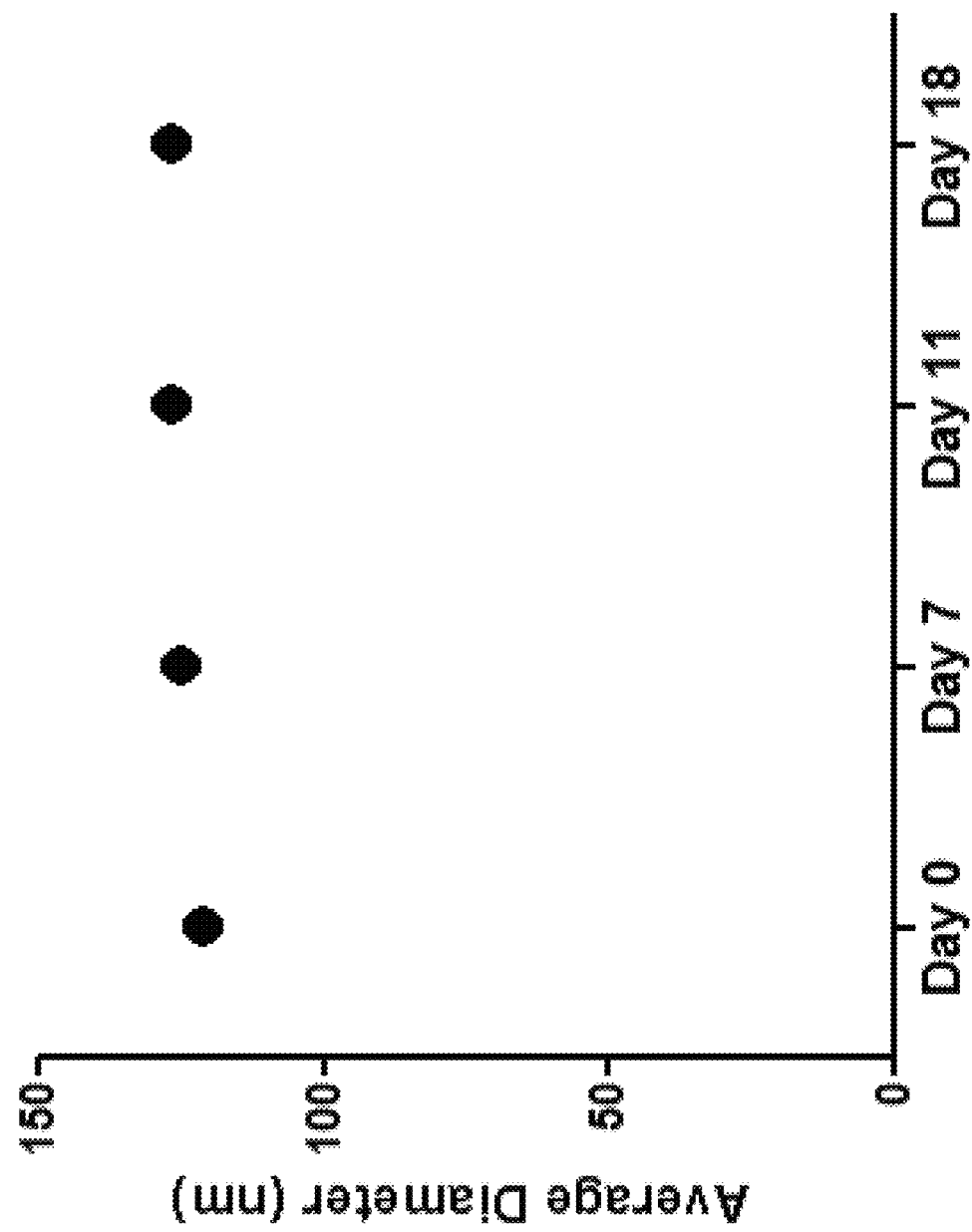
Figure 11E:
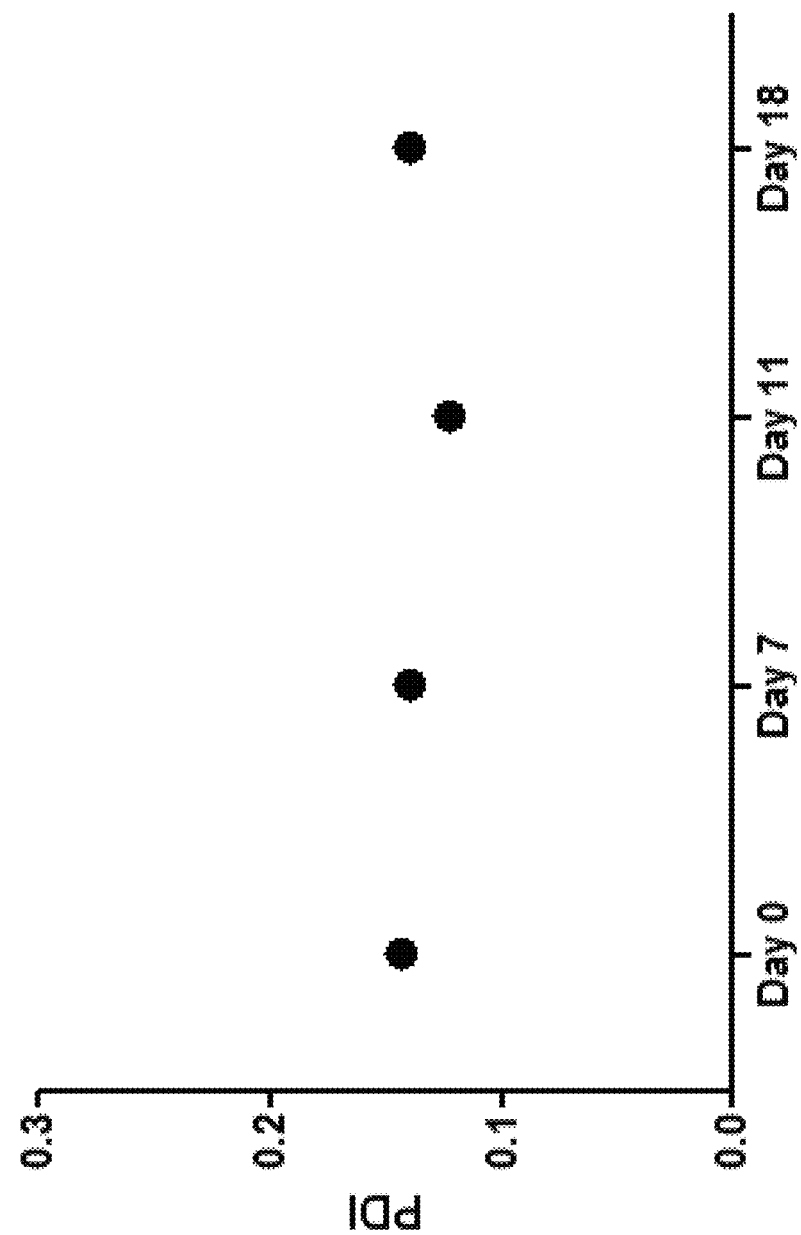

To explore whether lipid nanoparticles can deliver Cas9 (Streptococcus pyogenes Cas9) mRNA, we examined the potential of formulated mRNA to deliver Cas9 mRNA formulated with C12-200. Nanoparticles were formulated with Cas9 mRNA chemically modified to reduce TLR responses using controlled microfluidic mixing systems (FIG. 11A). These particles (termed nano.Cas9 hereafter) appear in spherical in morphology with a textured interior under Cryo-TEM (FIG. 11B). The mean particle diameter of nano.Cas9 is about 120 nm as determined by dynamic light scattering (FIG. 11C). The particle size of nano.Cas9 was the same on day 0, 7, 11 and 18 (FIGS. 11D and 11E), indicating these particles are stable for at least 18 days in PBS solution. To test whether nano.Cas9 was functional, we used a 293T reporter cell line stably expressing a GFP reporter and a GFP targeting sgRNA (sgGFP) (FIG. 8A). Cas9-mediated frameshift nonhomologous end-joining (NHEJ) events will result in GFP-negative cells. 293T cells were incubated with 0.4 μg/ml nano.Cas9 and GFP signal was measured by FACS at 5 days. As shown in FIG. 8B, 77.1±2.6% of cells (n=3) became GFP negative after nano_Cas9 treatment, suggesting that nanoparticle delivery of Cas9 mRNA can mediate genome editing in cells. To confirm that the GFP negative cells were caused by Cas9 editing, we performed deep sequencing of the GFP provirus region from genomic DNA (n=2). We observed insertional or deletional mutations (indels) surrounding the Cas9 cleavage site (FIGS. 8D-E). Most indels are frameshift (eg, 1nt and 2nt) mutations which cause loss-of-function of the GFP reporter. These data suggest that lipid nanoparticles can effectively deliver Cas9 mRNA in cultured cells.

Figure 12A:
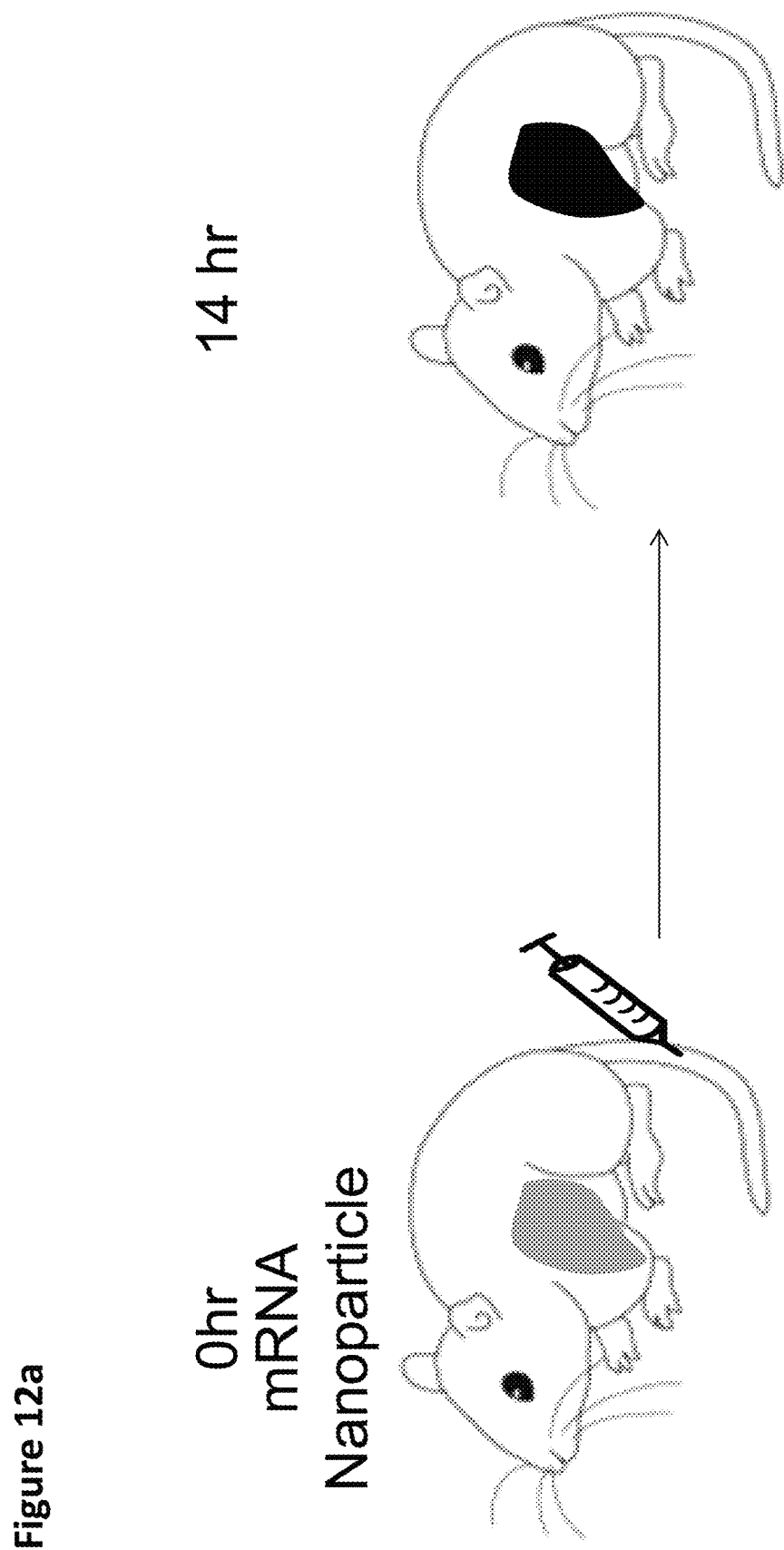
FIGS. 12A-12E provide data on expression of proteins in mouse liver after mRNA nanoparticles treatment.
Figure 12B:
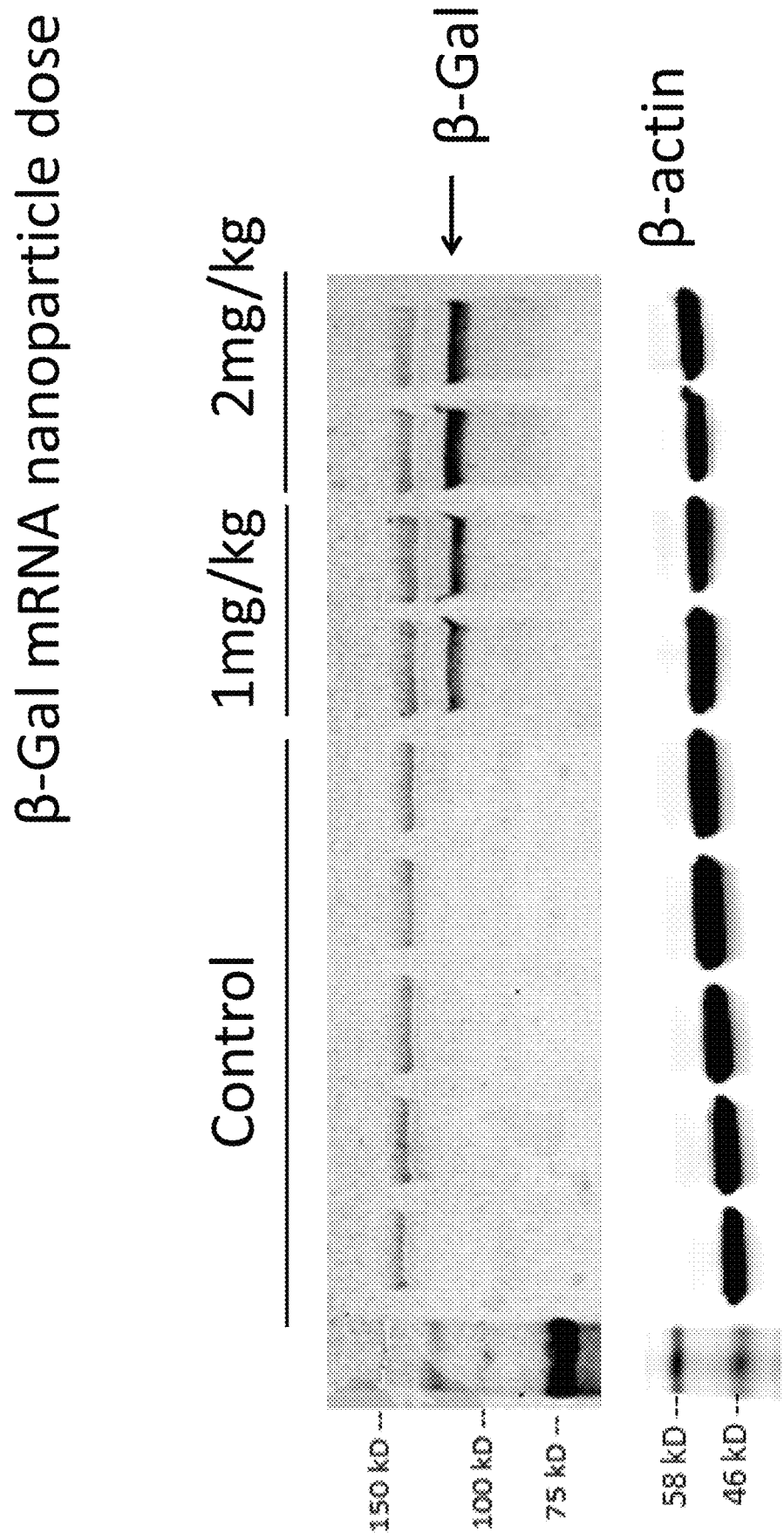
Figure 12C:
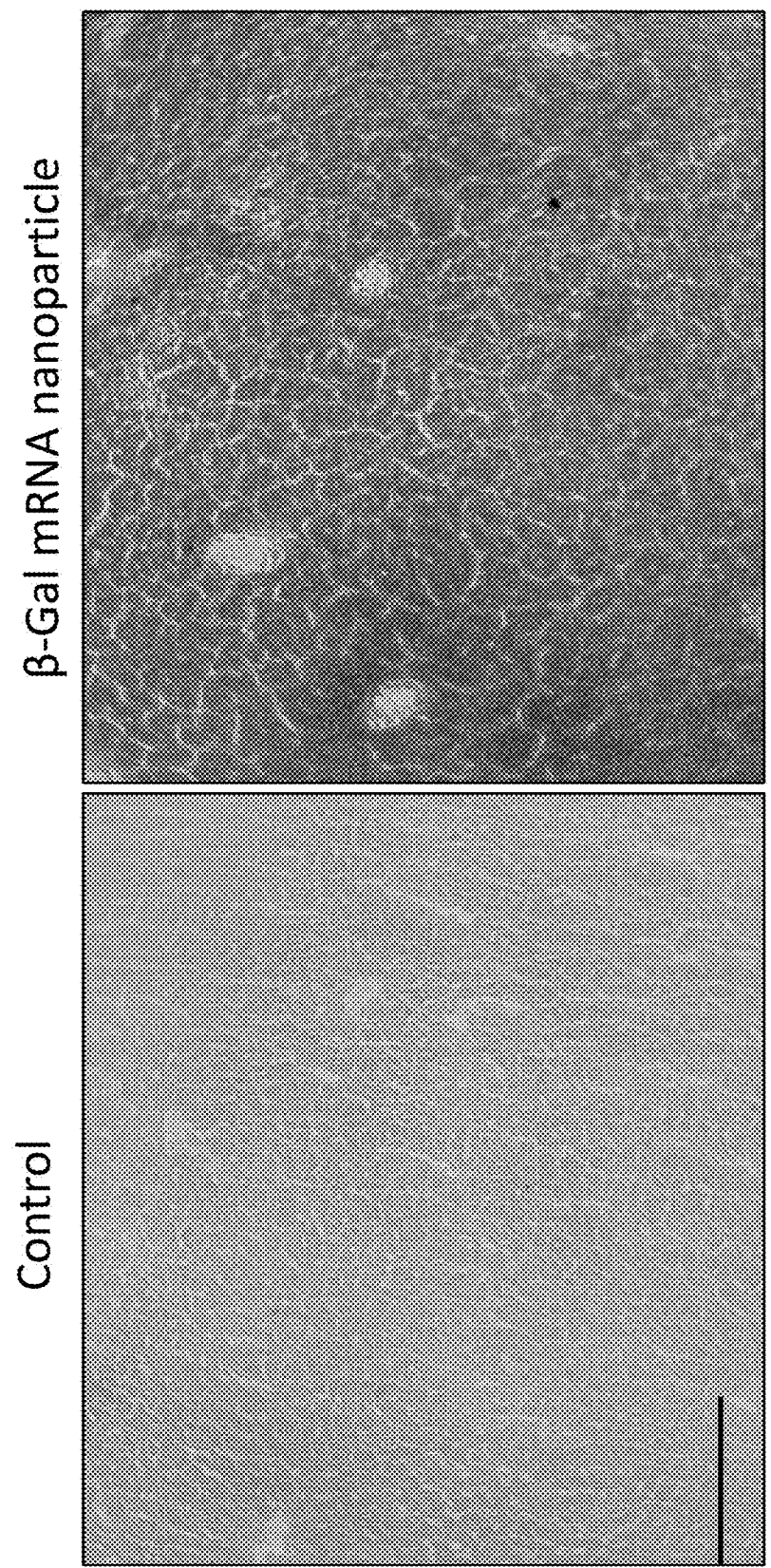
Figure 12D:
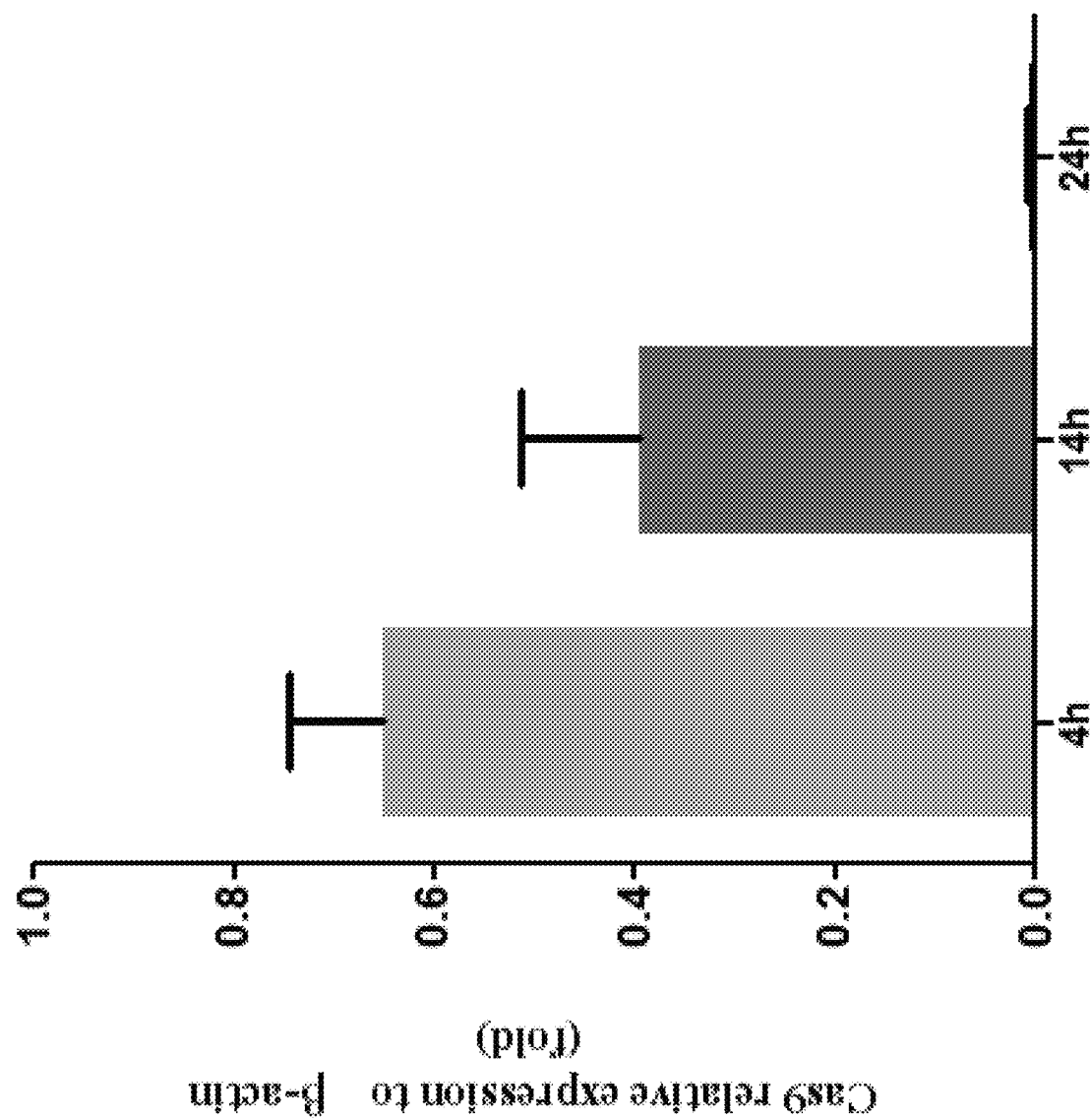
Figure 12E:
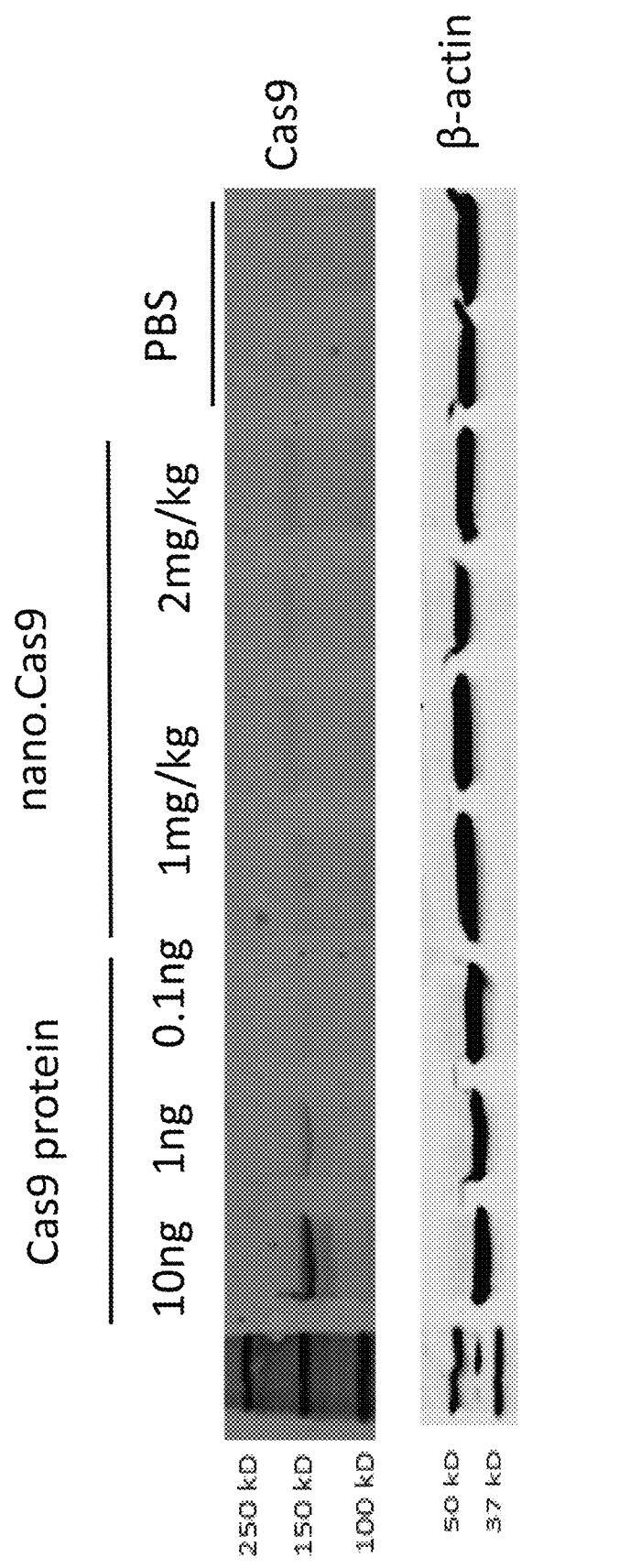

While lipid-nanoparticle delivery of siRNA to liver in vivo has been reported, the systemic delivery of mRNA has only recently been developed. To determine whether C12-200 lipid nanoparticles can systemically deliver Cas9 mRNA to adult animals, we intravenous (i.v.) injected C12-200 lipid nanoparticles encapsulated β-galactosidase (β-gal) mRNA or Cas9 mRNA (FIG. 12A). The size of β-gal mRNA (3.3 kb) is close to Cas9 mRNA (4.5 kb), and the activity of β-gal protein can be detected by enzyme reaction. β-gal protein is detected in mouse liver using immunoblot at 14 hrs after a single dose administration (1 mg/kg or 2 mg/kg), and the amount of protein expressed correlated with the dose of mRNA (FIG. 12B). To investigate whether β-gal is functional in vivo, we detected its enzyme activity in mouse liver. Majority of the cells in liver sections stained positive in β-gal activity assay (FIG. 12C), suggesting systemic delivery of long mRNA can produce functional protein within most of the cells in mouse liver. To determine whether lipid nanoparticles can deliver Cas9 mRNA, nano.Cas9 (1 mg/kg or 2 mg/kg) was injected i.v, and Cas9 protein in total liver lysates was detected by immunoblot (FIG. 12D). To measure the half-life of Cas9 mRNA in vivo, total RNA of liver is extracted and qPCR performed. The Cas9 mRNA presented in liver at 4 hrs and 14 hrs but was significantly diminished at 24 hrs, consistent with transient expression.

Figure 13A:
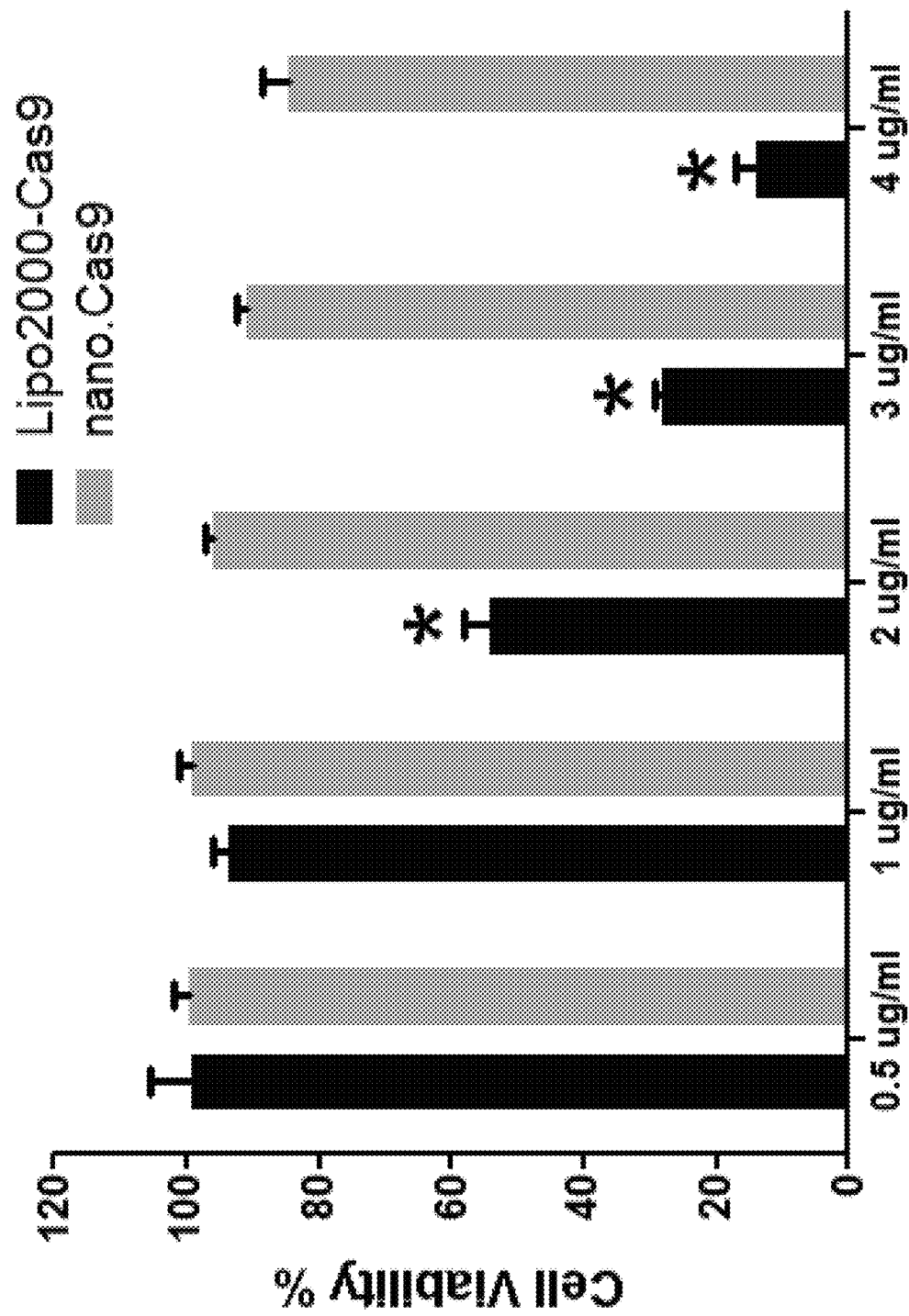
FIGS. 13A-13D provide results demonstrating that Cas9 mRNA nanoparticles are well tolerated.
Figure 13B:
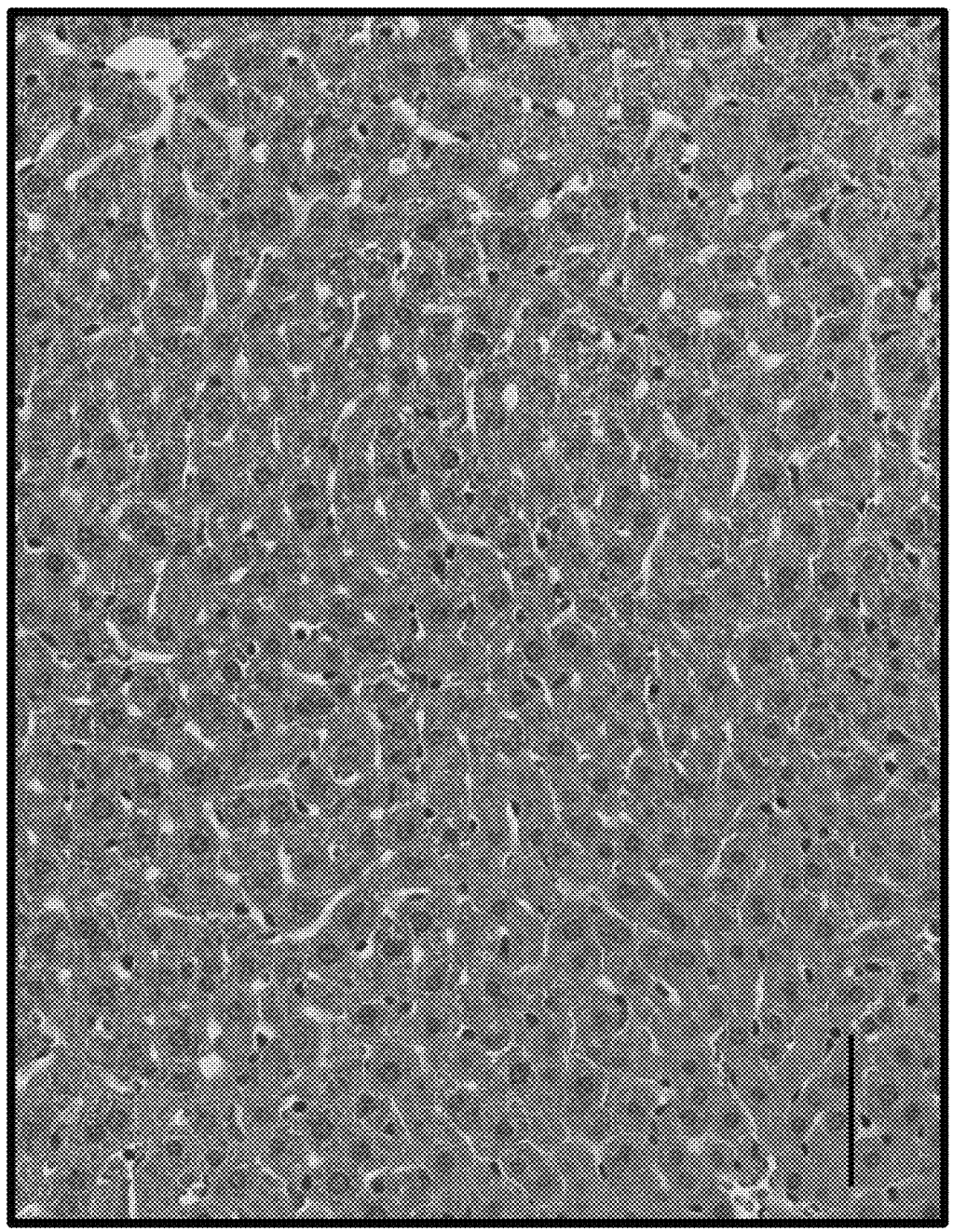
Figure 13C:
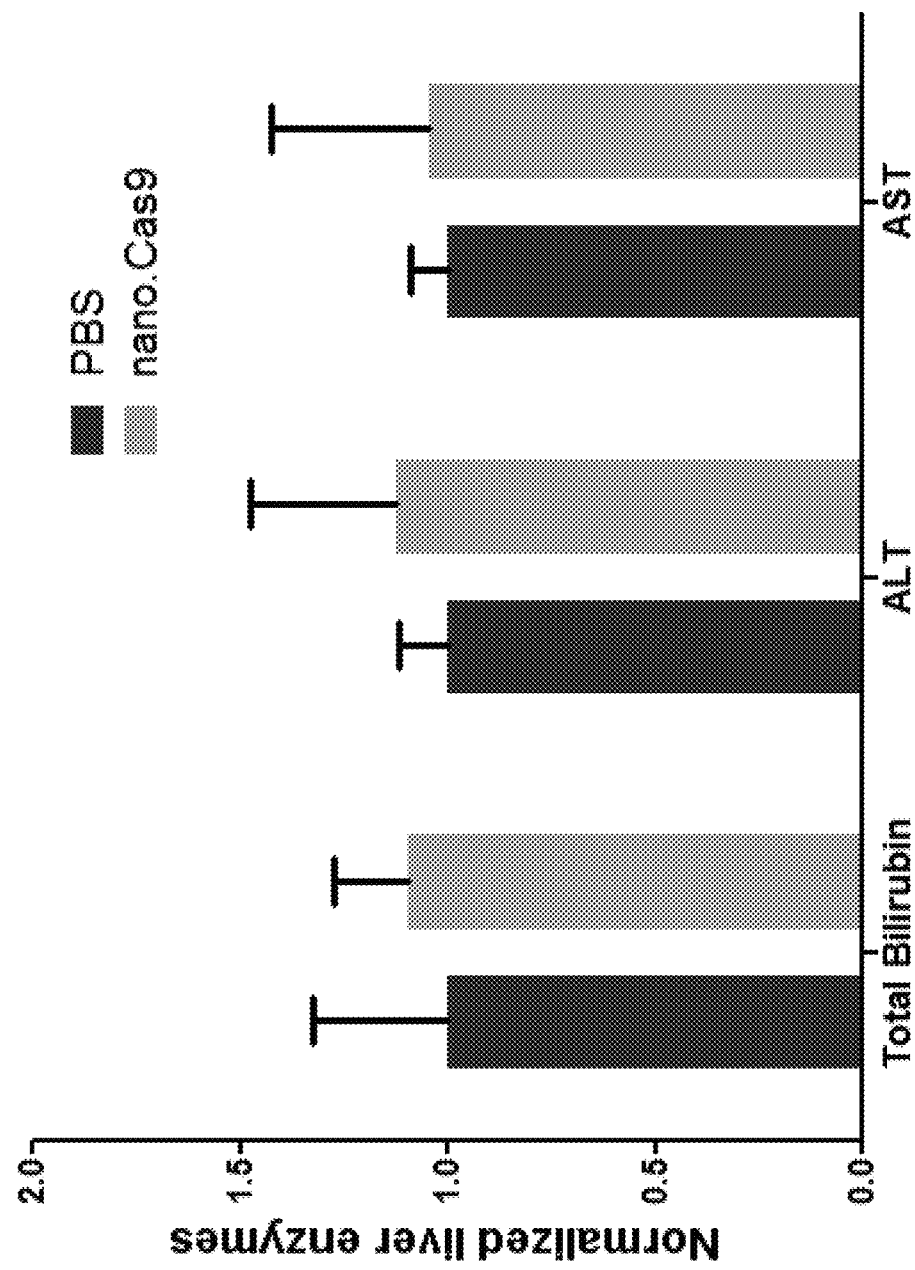
Figure 13D:
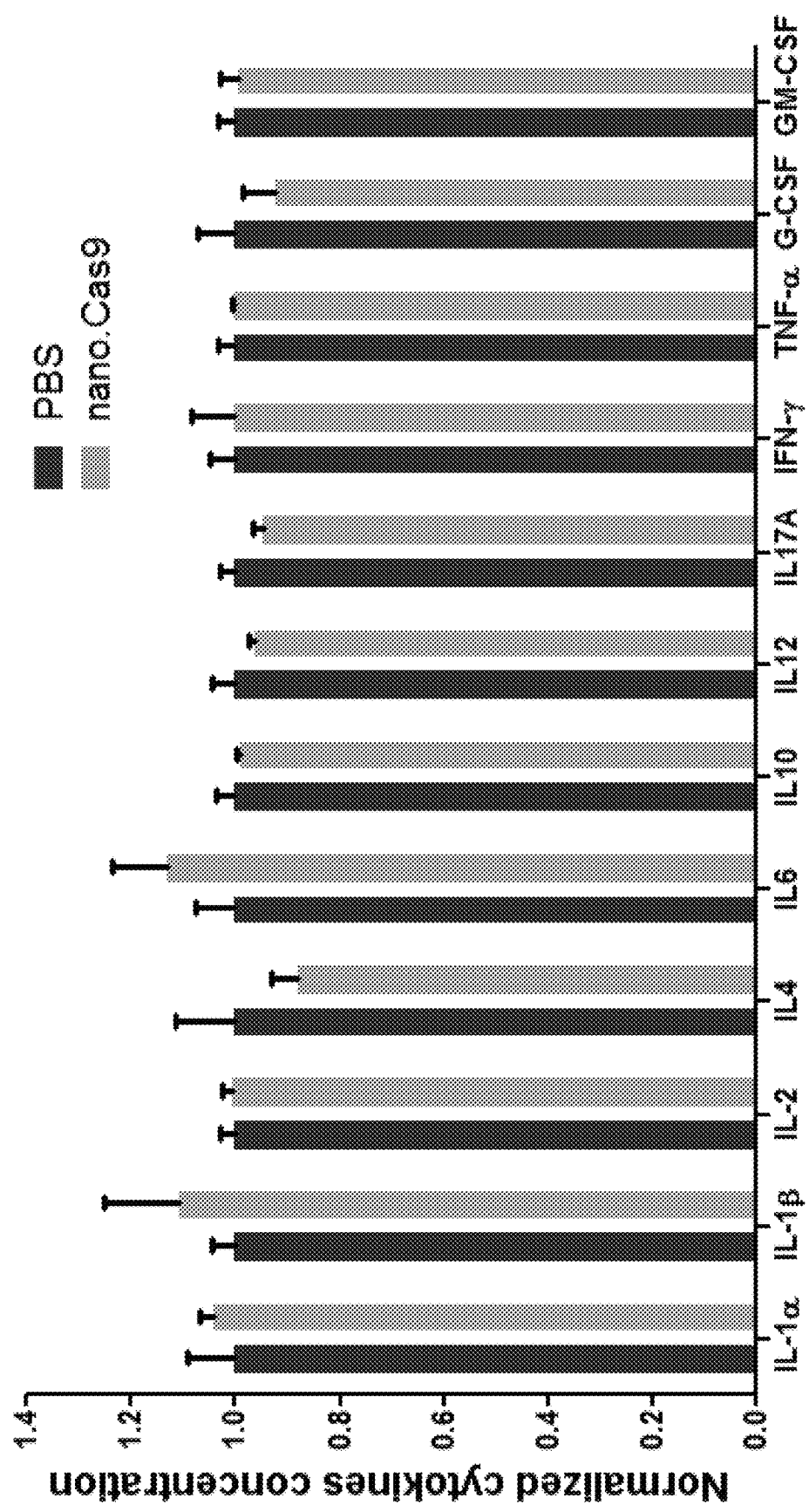

To determine the safety of nano.Cas9, we first compared the cytotoxicity of nano.Cas9 with Lipofectamine 2000 in 293T cells. Significant toxicity was observed at the dose of more than 1 μg/ml mRNA-Lipofectamine 2000 complex, in contrast, nano.Cas9 was well tolerated at 4 μg/ml (FIG. 13A). In contrast, high efficient gene editing (77.1±2.6%) can be reached at the dose of 400 ng/ml nano.Cas9 at 293T cells (FIG. 8), suggesting its favorable safety margin. The nano.Cas9 (2 mg/kg) is well tolerated in animals, as indicated by intact liver histology, normal serum biochemistry and cytokine levels in plasma (FIGS. 13B-D).

Figure 9A:
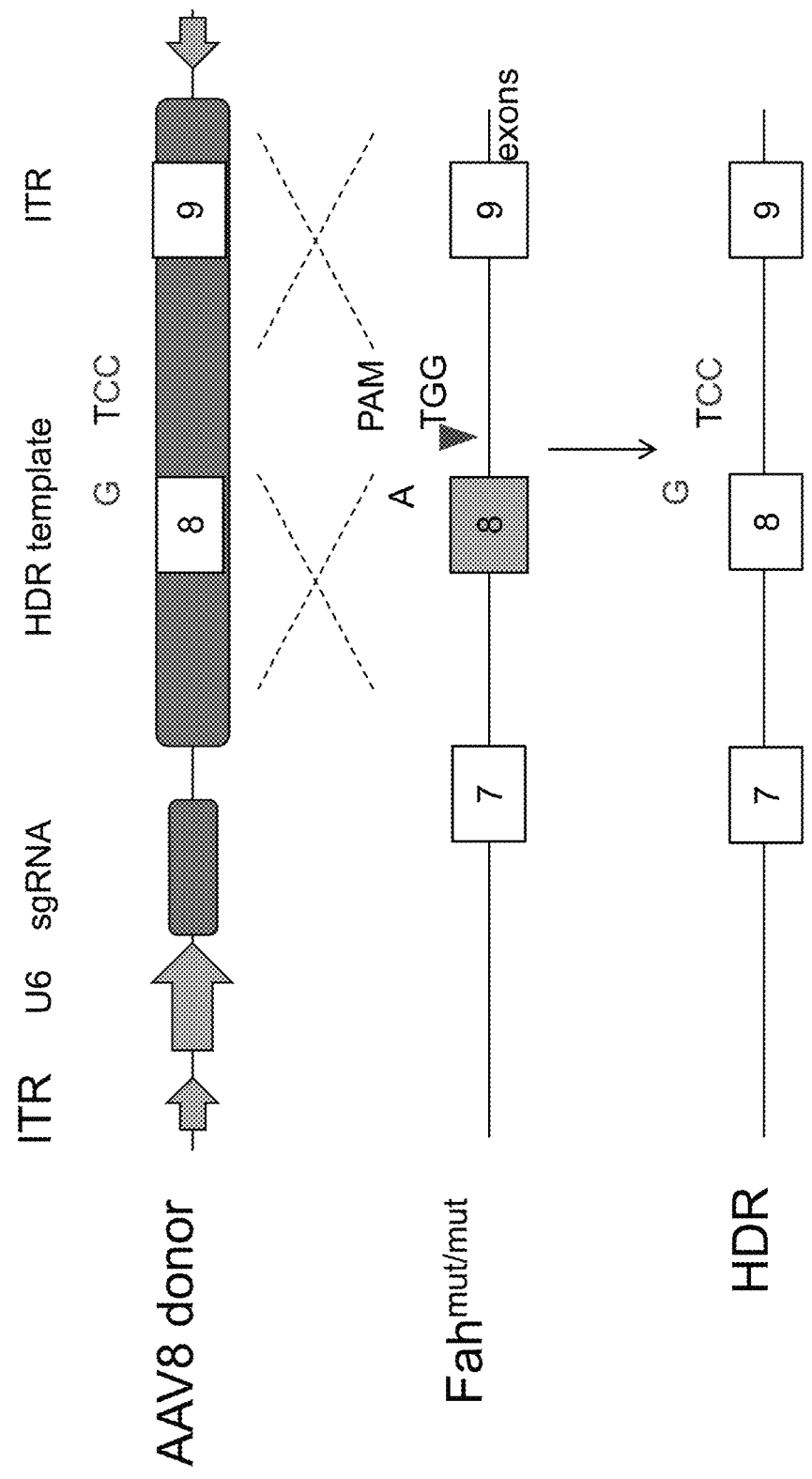
FIGS. 9A-9E provide in vivo delivery of Cas9 mRNA and AAV-sgRNA-HDR template cures type I tyrosinemia mice.
Figure 9B:
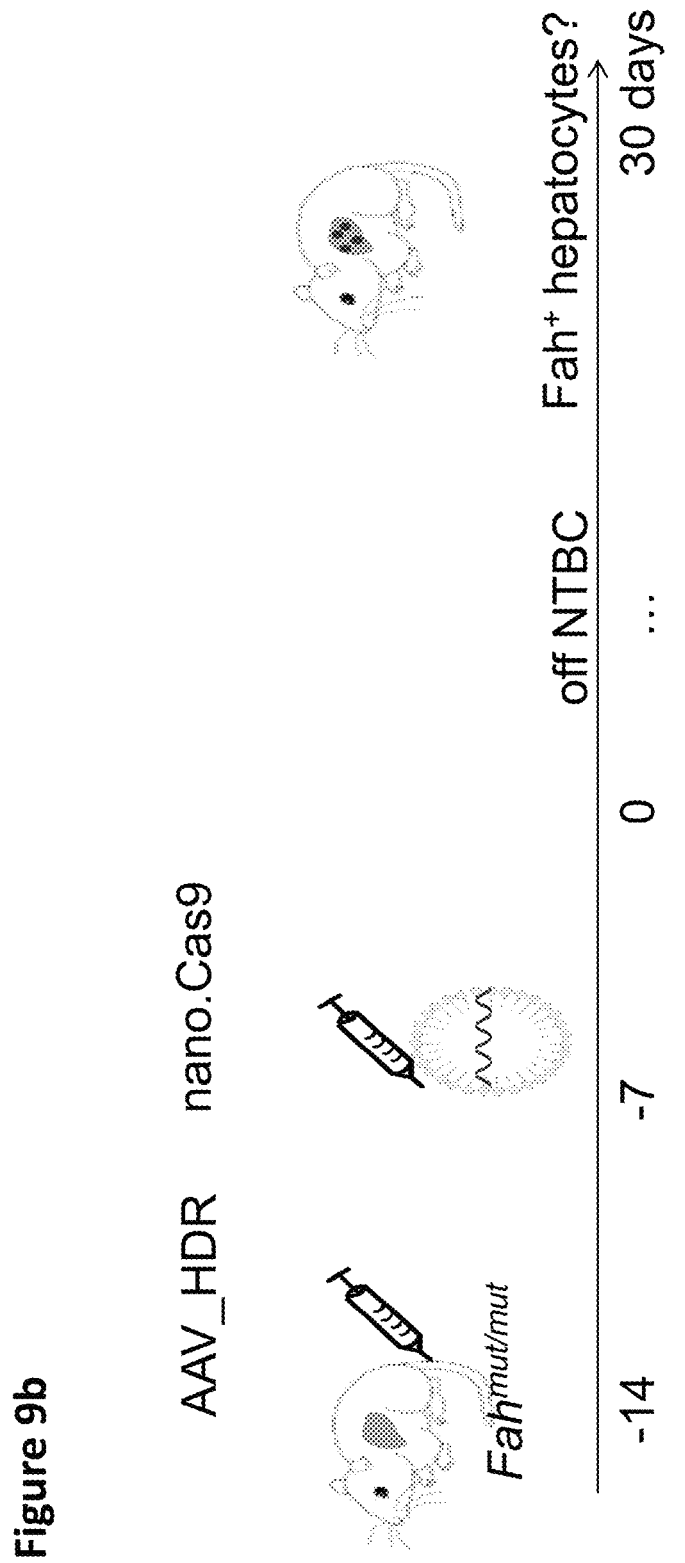
Figure 9C:
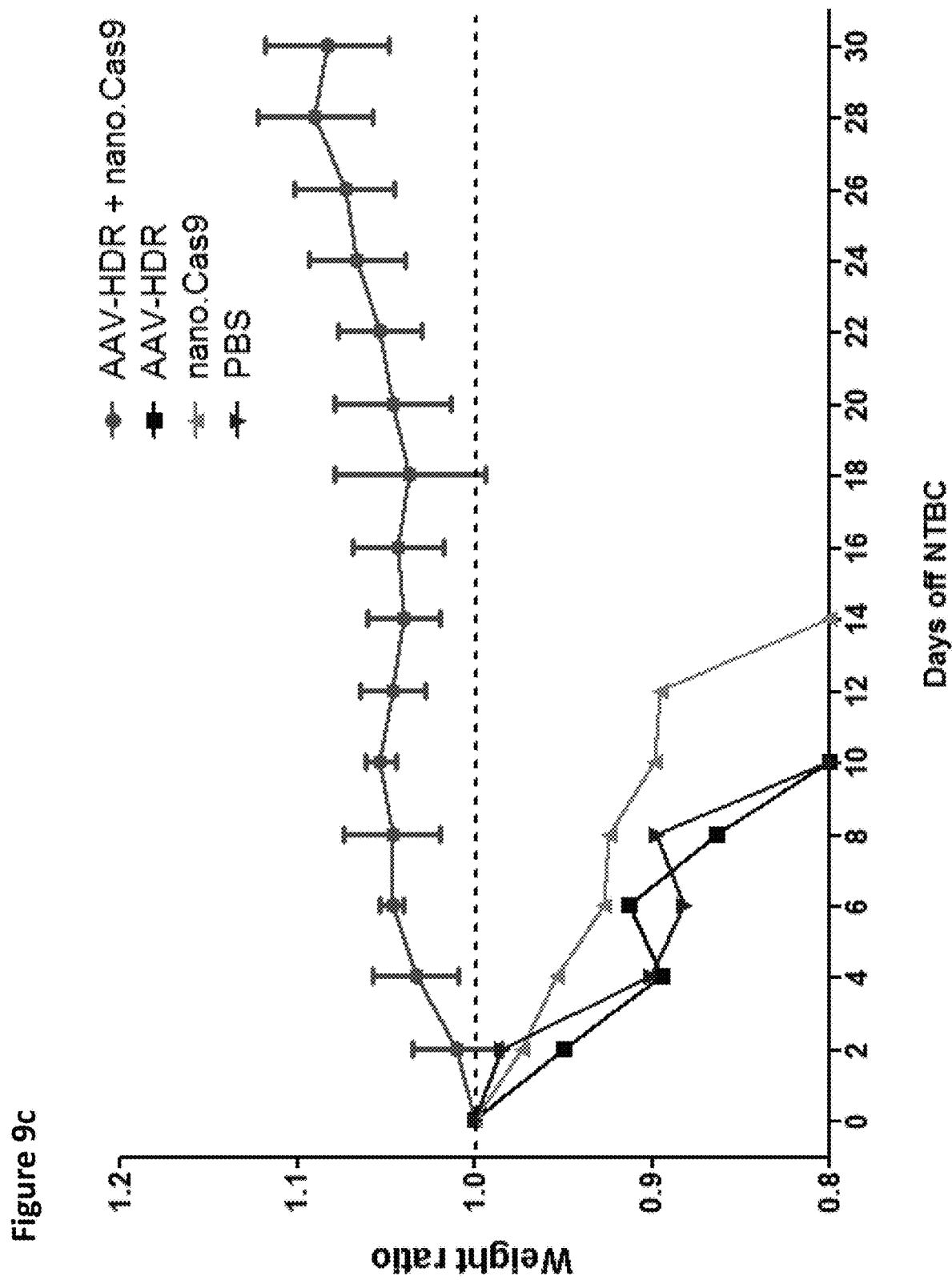
Figure 9D:
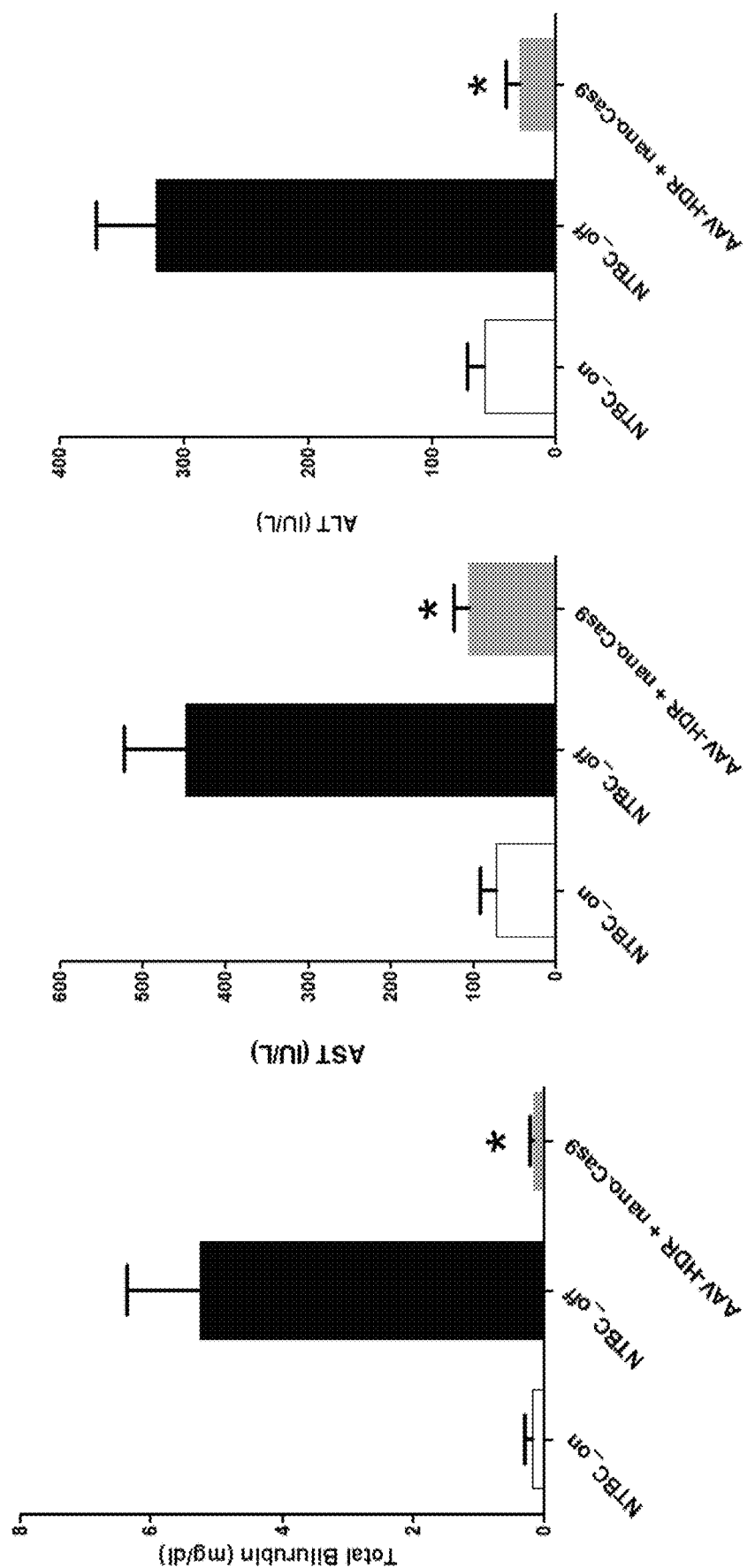
Figure 9E:
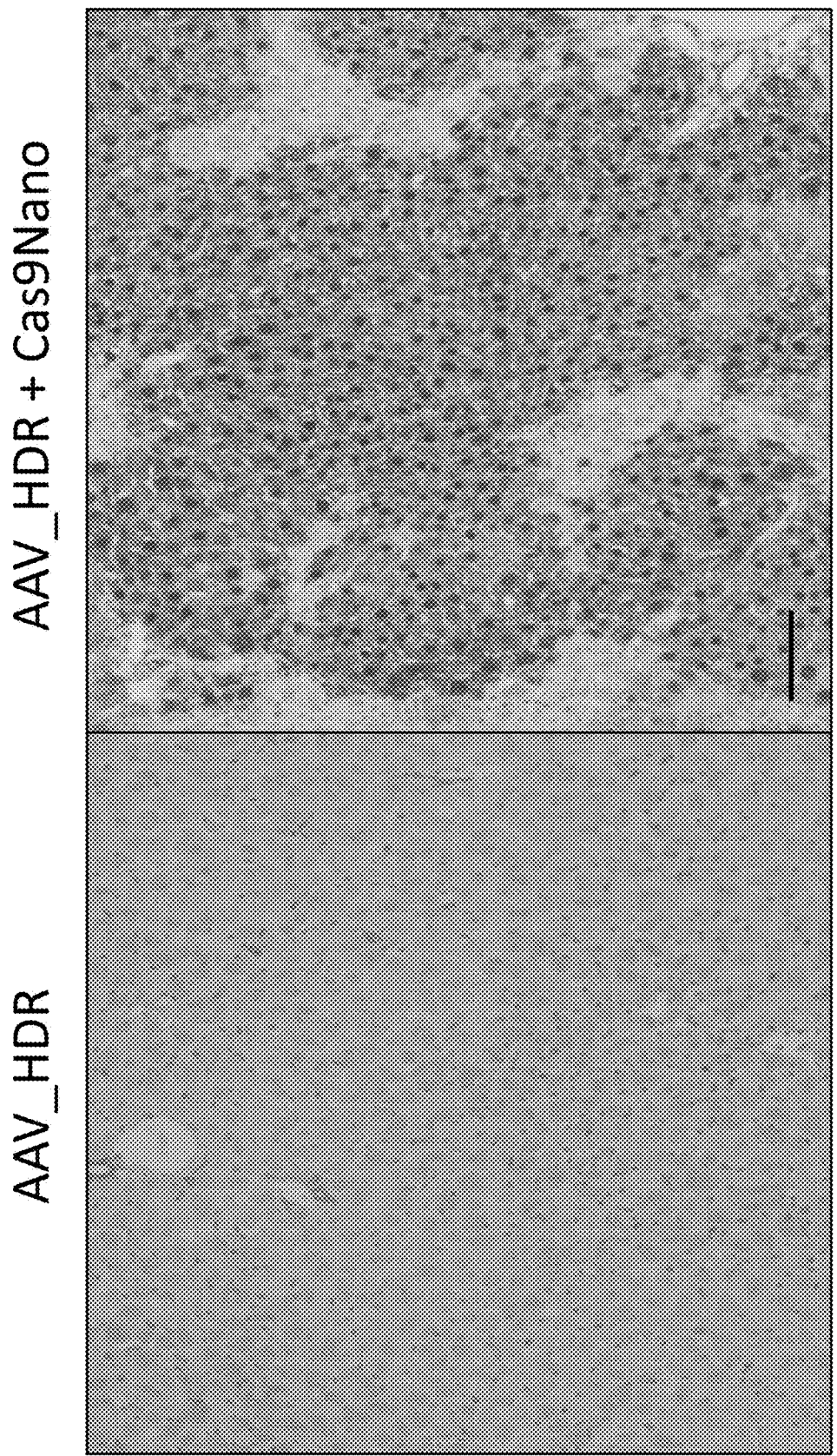

To investigate whether nano.Cas9 can be applied for genome editing in vivo, we used the Fah$^{mut/mut}$ mouse model of HTI. These mice possess the same G→A mutation in exon 8 as the common form of this human disease. To enable repair of the Fah gene, we designed an AAV vector with a U6-sgRNA expression cassette and an HDR template (termed AAV-HDR thereafter), which consists of 1.7kb homologous sequence to the Fah genomic region (FIG. 9A). We designed the HDR template to perform two tasks (1) "G" to repair the mutant "A" (2) "CC" to mutate the PAM sequence to prevent self-cleavage (FIG. 9A). These were packaged using an AAV2/8 serotype, which has shown the ability to target the liver. To explore whether the nano.Cas9 and AAV-HDR combination treatment can repair the Fah mutation in vivo, a cohort of Fah$^{mut/mut}$ mice (n=3) were i.v. injected with 6e11 genome copies of AAV-HDR (FIG. 9B) at Day −14, 2 mg/kg nano.Cas9 at Day −7 and taken off NTBC water at Day 0 (FIG. 9B). Mice treated with PBS, AAV-HDR alone or nano.Cas9 alone serve as controls. As shown in FIG. 9C, nano.Cas9+AAV-HDR completely prevented body weight loss upon NTBC water withdrawal, whereas control mice rapidly lost 20% body weight and had to be sacrificed. All the mice in nano.Cas9+AAV-HDR group survived after 30 days post NTBC withdrawal. At 30 days after NTBC water withdrawal, liver histology and serum biomarkers (AST, ALT) indicated that liver damage was rescued in nano_Cas9+AAV-HDR treated mice compared to control mice (FIGS. 9D, 9E). Immunohistochemistry staining also detected patches of Fah positive hepatocytes (FIG. 9F), representing a fraction of total hepatocytes.

Figure 4:
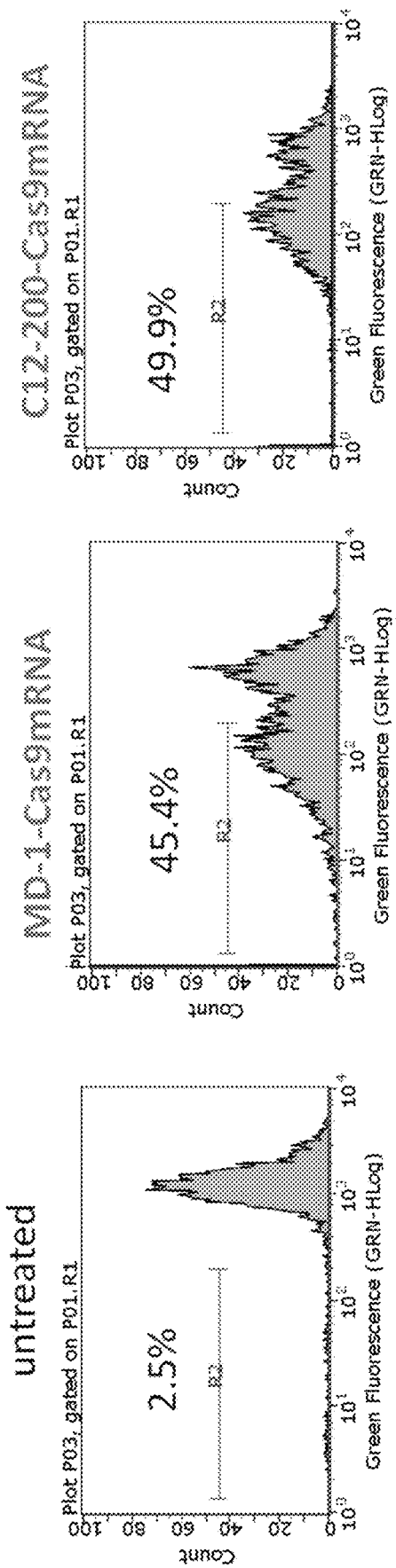
FIG. 4 is a set of histographs showing EGFP expression in untreated HEK293T cells (left panel), HEK293T cells treated with MD-1 expressing Cas9 mRNA (center panel), or C112-200 expressing Cas9 mRNA (right panel).
Figure 10A:
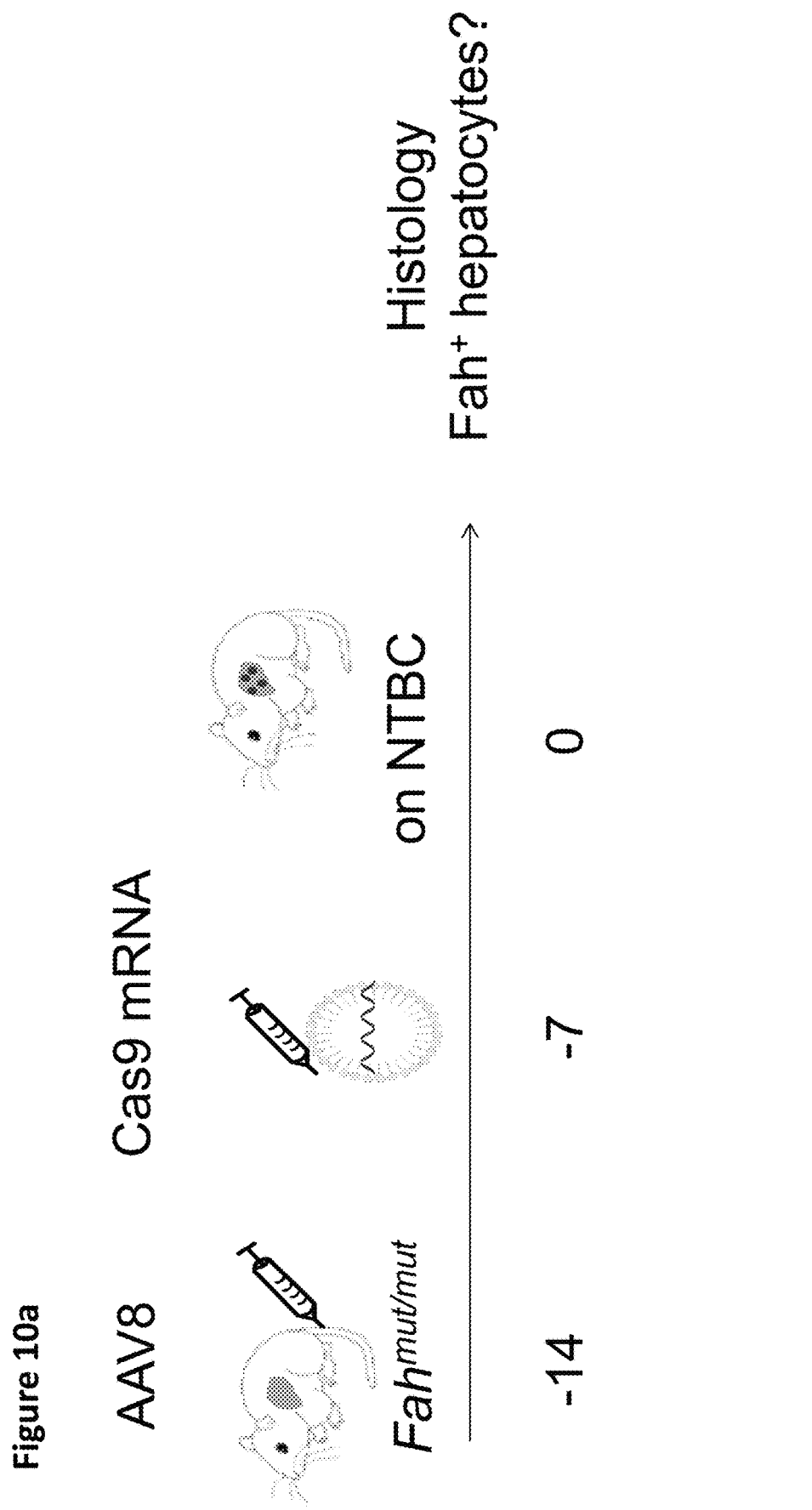
FIG. 10A: Fah$^{mut/mut}$ mice were kept on NTBC water and euthanized 7 days after nano.Cas9 treatment to estimate initial repair rate.
Figure 10B:
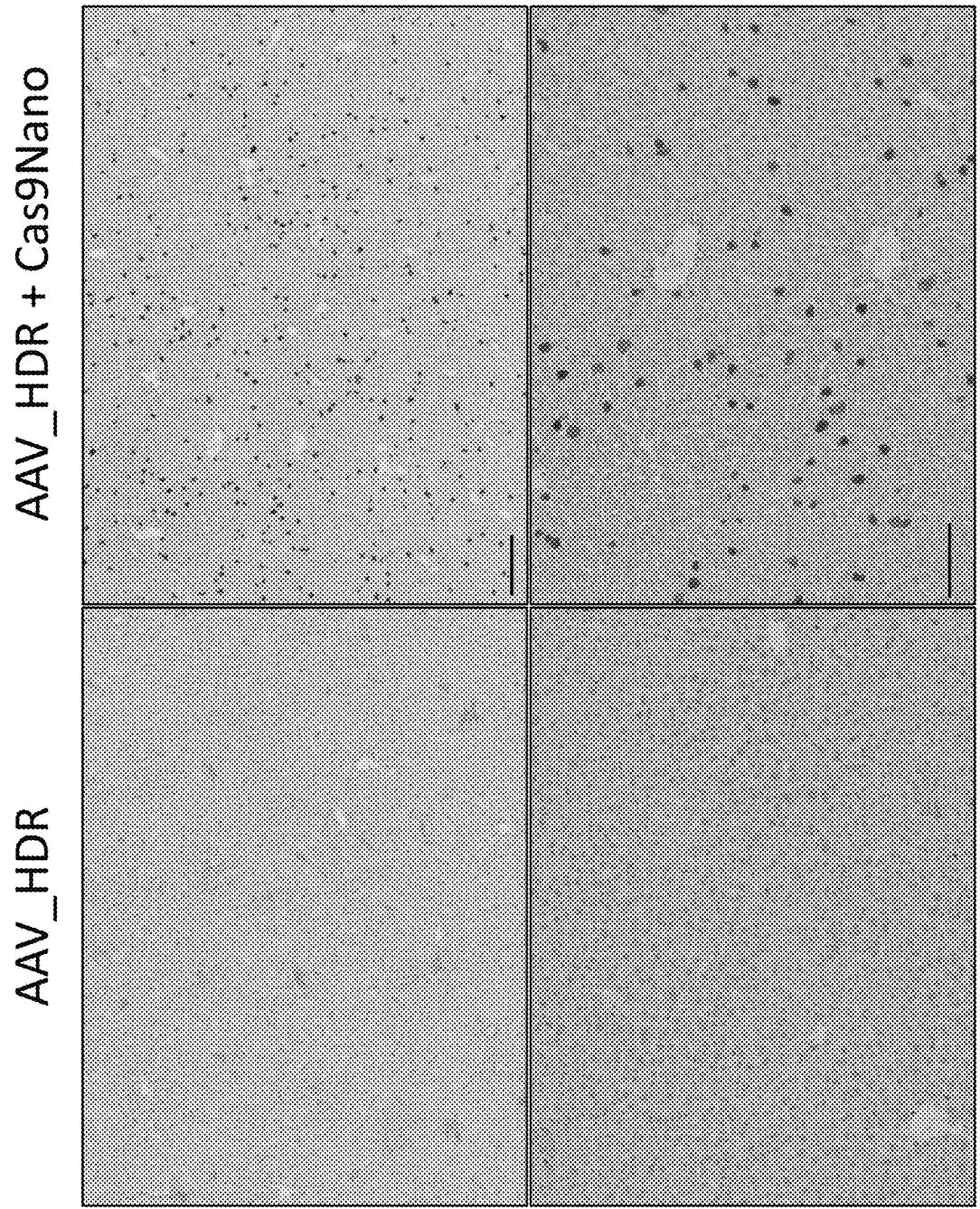
FIG. 10B: Fah immunohistochemistry (IHC).
Figure 10C:
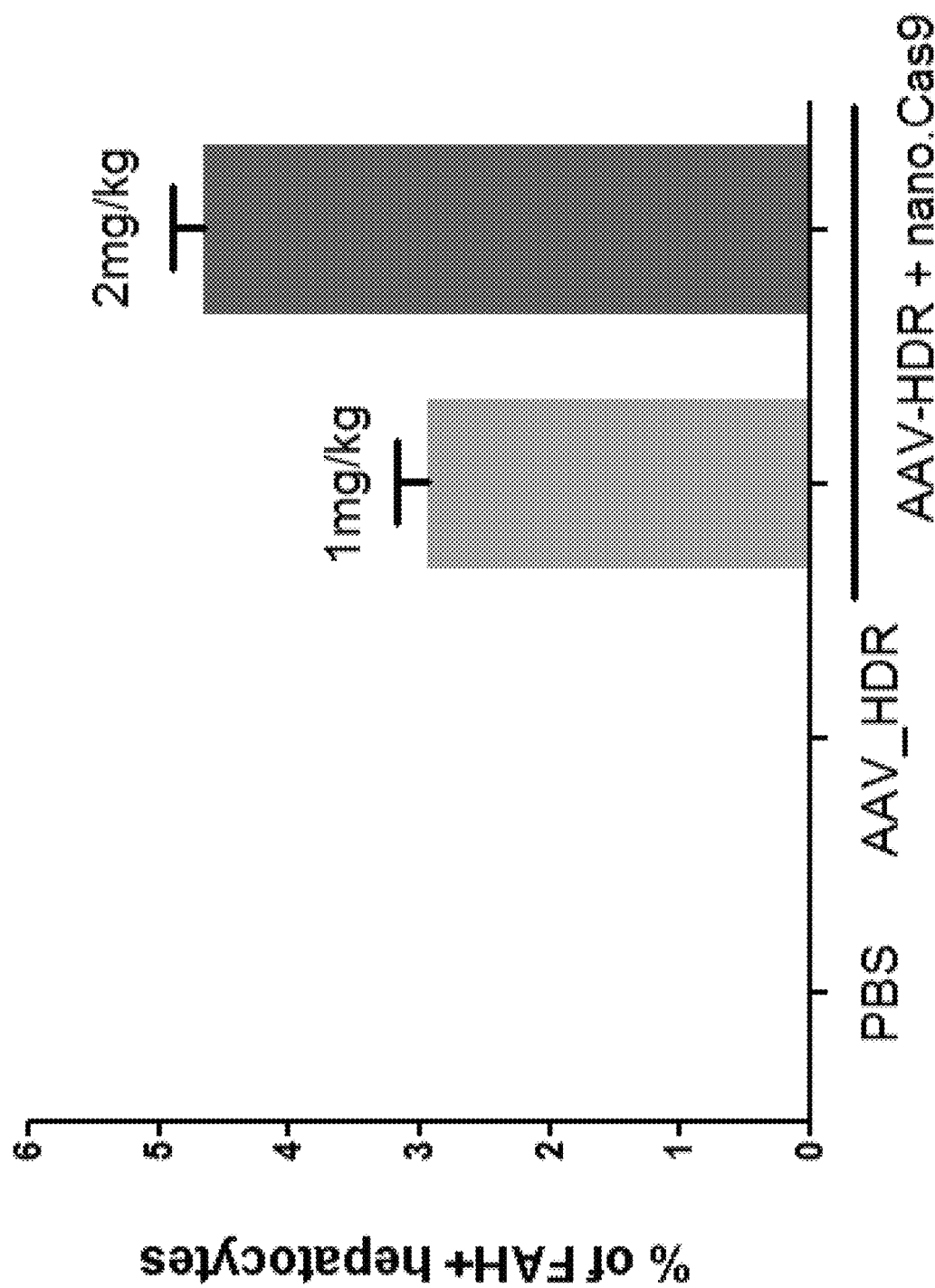
FIG. 10C: The percentage of FAH+ positive cells were counted.
Figure 10D:
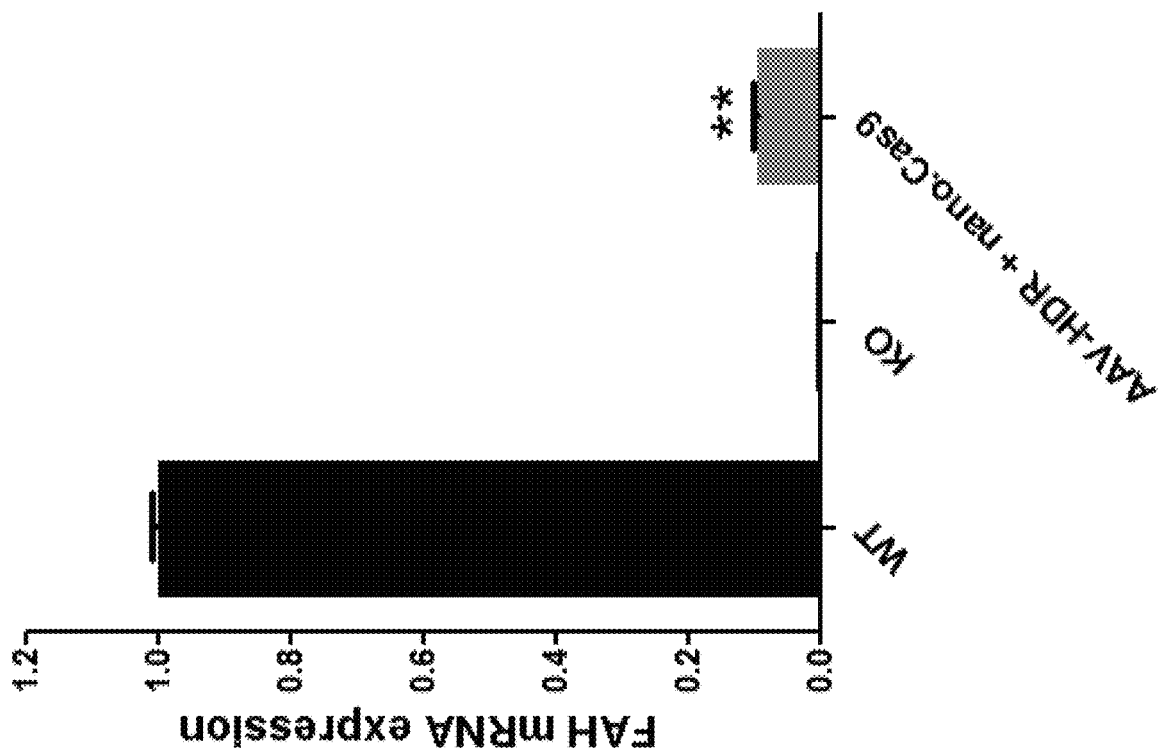
FIG. 10D: Quantitative RT-PCR measurement of wild-type the expression of Fah mRNA.
Figure 10E:
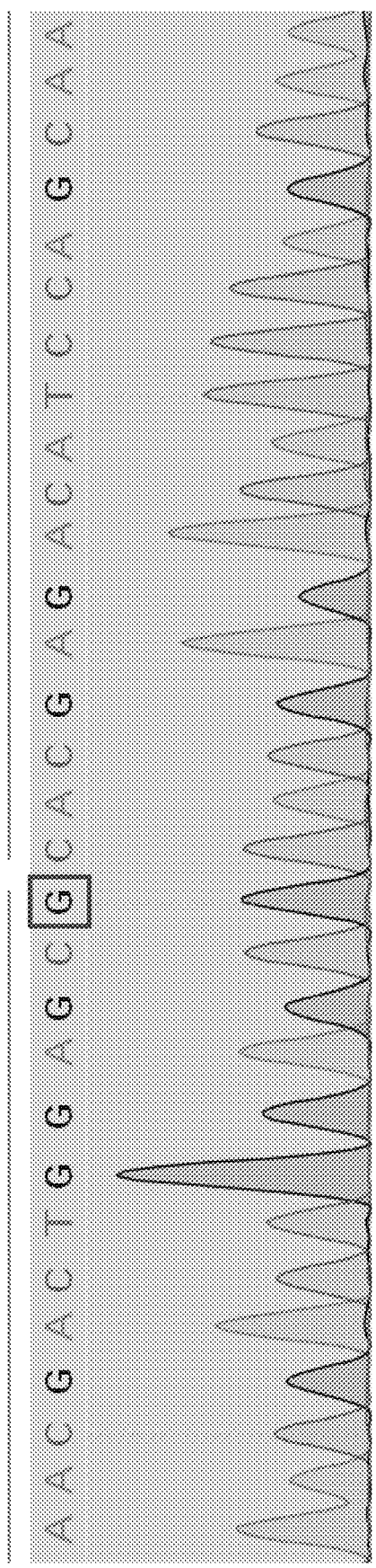
FIG. 10E: Sequence of repaired Fah mRNA in treated mice. The corrected G nucleotide is circled.
Figure 10F:
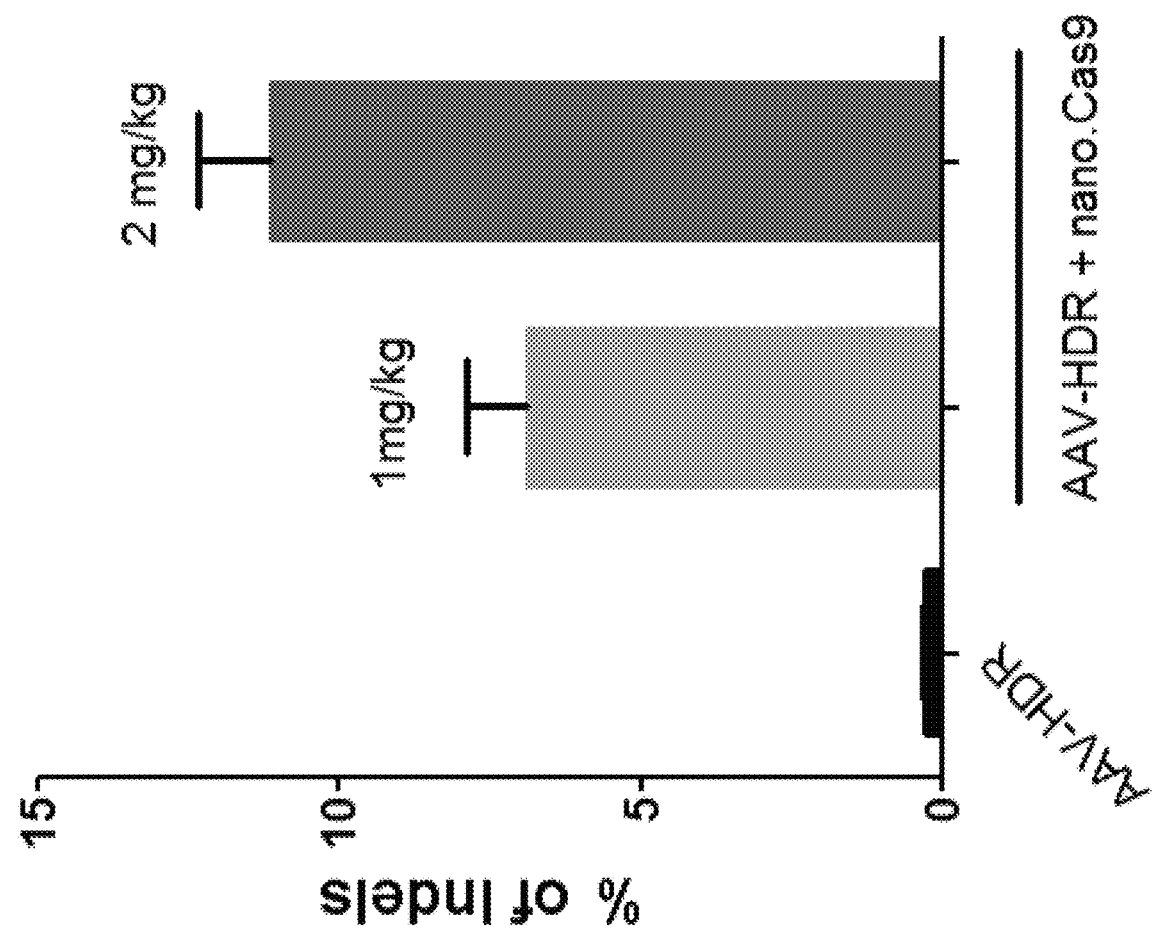
FIG. 10F: indels of total DNA from liver.

To determine the initial Fah gene repair rate in vivo, we injected Fah$^{mut/mut}$ mice with nano.Cas9 and AAV-HDR and kept the mice on NTBC water to prevent expansion of Fah corrected cells (FIG. 10A). As shown in FIGS. 10B and 10C, 4.6% hepatocytes stained positive of Fah protein by immunohistochemistry in nano.Cas9 plus AAV-HDR treated animals. The number of Fah positive hepatocytes is correlated with the dose of nano.Cas9 (FIG. 10C). To investigate whether Fah splicing is restored in the liver, we performed qRT-PCR using primers spanning Fah exons 8 and 9 and observed 9.5% FAH mRNA expression was restored without selection (FIG. 10D). Sanger sequencing of the RT-PCR bands in nano.Cas9+AAV-HDR treated mice confirmed that the corrected G nucleotide is presented at the end of exon 8. To examine genome editing in the liver, we performed deep sequencing of the Fah locus in liver genomic DNA. We observed an average of 11.1% indels at predict sgRNA target region within nano.Cas9 (2 mg·kg)+AAV-HDR group (n=3 mice).

CRISPR/Cas9 may cause indels at off-target genomic sites, and in order to determine potential off-target effects after Cas9 mRNA delivery in vivo, we performed deep sequencing at three of the top ranking predicted off-target sites. Compared to indels at the on-target Fah site, indels were detected at the assayed off-target sites in nano_Cas9+ AAV-HDR treated mouse and these numbers are comparable with AAV alone treated mouse, suggesting that Cas9 mRNA delivery has low off-target effects at assayed sites.

Therapeutic editing has broad potential to treat a range of diseases through the permanent correction of genetic defects. Through combining viral and nonviral nucleic acid delivery we report the first therapeutically relevant formulations capable of inducing repair of a disease gene in an adult animal, and further advancing the technology of gene editing. Herein we reported that therapeutic delivery of CRISPR/Cas9 using mRNA and AAV combination can effectively correct the Fah mutation and cure a mouse model of tyrosinemia. Systemic delivery of Cas9 mRNA by lipid nanoparticle and sgRNA/HDR template by AAV corrected Fah mutation and restored Fah splicing in more than 1/25 hepatocytes in adult mouse liver. This treatment is well-tolerated in mice and fully rescued body weight loss and liver damage in tyrosinemia mice.

We showed that systemic delivery of Cas9 mRNA by lipid nanoparticle can effectively mediate genome editing in vivo. This transient Cas9 mRNA delivery method provides a platform for non-viral CRISPR/Cas9 delivery. Administration of Cas9 mRNA using non-viral and transient expression vehicles can allow repeated dosing to increase efficiency and can potentially prevent long-term side-effects, such as potential immune-response against Cas9 and off-target editing. Our mRNA delivery method is amenable to deliver Cas9 nickase to reduce off-targeting effects or therapeutic mRNA such as Fah or Erythropoietin.

We applied AAV, a well-studied clinical viral vehicle, to deliver sgRNA and HDR template to the liver. Because AAV serotypes target a wide range of tissue in vivo, our method can target organs other than liver through engineering of mRNA delivery tools. This study has demonstrated that therapeutic delivery of Cas9 mRNA and AAV can correct genetic mutation in mice.

INCORPORATION BY REFERENCE

All references, articles, publications, patents, patent publications, and patent applications cited herein are incorporated by reference in their entireties for all purposes.

The invention claimed is:

1. A method for inducing repair of a gene in a subject in need thereof, the method comprising administering to the subject:
(i) one or more guide RNA (gRNA);
(ii) a repair template; and
(iii) a CRISPR-Cas system comprising a Cas mRNA, wherein (i) and (ii) are provided in a same or different viral vector, and (iii) is provided in a lipid nanoparticle.

2. The method of claim 1, wherein the viral vector is selected from the group consisting of adeno-associated virus (AAV), adenovirus, retrovirus, and lentivirus vectors.

3. The method of claim 1, wherein the repair template is selected from the group consisting of a DNA repair template, an mRNA repair template, a sRNA repair template, an miRNA repair template, and an antisense oligonucleotide repair template.

4. The method of claim 1, wherein the gRNA hybridizes to a target sequence associated with a genetic disease or disorder or a cancer in a cell in the subject.

5. The method of claim 4, wherein the genetic disease or disorder is an inborn error of metabolism selected from disorders of amino acid transport and metabolism, lipid or fatty acid transport and metabolism, carbohydrate transport and metabolism, and metal transport and metabolism.

6. The method of claim 4, wherein the genetic disease or disorder is hemophilia, cystic fibrosis, or sickle cell disease.

7. The method of claim 1, wherein the subject is an animal.

8. The method of claim 1, wherein the gRNA is administered prior to the CRISPR-Cas system.

9. The method of claim 7, wherein the method achieves a modification rate of about 1% to about 10% of a population of cells in a target tissue of the subject.

10. The method of claim 1, wherein the lipid nanoparticle comprises cKK-E12.

11. The method of claim 10, wherein the lipid nanoparticle further comprises 1,2-dioleoyl-sn-glycero-3-phosphoethanolamine (DOPE) and cholesterol C14-PEG2000.

12. A method for modifying a target nucleotide sequence in a target tissue of a subject in need thereof, comprising administering to the subject:

(i) a viral vector comprising a guide RNA (gRNA); and
(ii) a lipid nanoparticle comprising a CRISPR-Cas system comprising a Cas mRNA.

13. The method of claim 12, wherein the viral vector is selected from the group consisting of adeno-associated virus (AAV), adenovirus, retrovirus, and lentivirus vectors.

14. The method of claim 12, wherein the lipid nanoparticle comprises one or more of a phospholipid, cholesterol, polyethylene glycol (PEG)-lipid, and a lipophilic compound.

15. The method of claim 12, wherein the lipid nanoparticle comprises cKK-E12.

16. The method of claim 15, wherein the lipid nanoparticle further comprises 1,2-dioleoyl-sn-glycero-3-phosphoethanolamine (DOPE) and cholesterol C14-PEG2000.

17. The method of claim 12, further comprising administering to the subject a repair template selected from the group consisting of a DNA repair template, an mRNA repair template, a siRNA repair template, an miRNA repair template, and an antisense oligonucleotide repair template.

18. The method of claim 12, wherein the gRNA is administered prior to the CRISPR-Cas system.

19. The method of claim 12, wherein the CRISPR-Cas system is expressed in the target tissue for no more than about two months per administration.

20. The method of claim 19, wherein the gRNA is expressed in the target tissue for at least 2 weeks.

21. The method of claim 20, wherein about 1% to about 10% of cells within the target tissue are modified.

22. The method of claim 1, wherein the lipid nanoparticle comprises one or more of a phospholipid, cholesterol, and polyethylene glycol (PEG)-lipid.

23. The method of claim 1, wherein the gRNA and the repair template are provided in an adeno-associated virus (AAV) vector.

24. The method of claim 23, wherein the CRISPR-Cas system is a CRISPR-Cas9 system.

25. The method of claim 1, wherein the gRNA and the repair template are provided in adeno-associated virus 2/8 (AAV 2/8) vector.

26. The method of claim 12, wherein the viral vector is an adeno-associated virus (AAV).

27. The method of claim 26, wherein the CRISPR-Cas system is a CRISPR-Cas9 system.

28. The method of claim 12, wherein the viral vector is an adeno-associated virus 2/8 (AAV 2/8).

* * * * *

UNITED STATES PATENT AND TRADEMARK OFFICE
CERTIFICATE OF CORRECTION

PATENT NO. : 10,941,395 B2
APPLICATION NO. : 16/029273
DATED : March 9, 2021
INVENTOR(S) : Hao Yin et al.

Page 1 of 1

It is certified that error appears in the above-identified patent and that said Letters Patent is hereby corrected as shown below:

In the Claims

In Claim 3, Column 33, Line 60, delete "sRNA" and insert -- siRNA --;

In Claim 12, Column 35, Line 2, delete "CRISP R-Cas" and insert -- CRISPR-Cas --.

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*